(12) United States Patent
Divakar et al.

(10) Patent No.: US 11,952,617 B2
(45) Date of Patent: Apr. 9, 2024

(54) METHODS FOR MULTIPLEX DETECTION OF POLYNUCLEOTIDES USING UNBOUND FLUORESCENT PROBES AND QUENCHER OLIGONUCLEOTIDES

(71) Applicant: KASA BIO, L.L.C., Peachtree Corners, GA (US)

(72) Inventors: Kiran Madanahally Divakar, Alpharetta, GA (US); Shashi Bala, Alpharetta, GA (US)

(73) Assignee: KASA BIO, L.L.C., Peachtree Corners, GA (US)

( * ) Notice: Subject to any disclaimer, the term of this patent is extended or adjusted under 35 U.S.C. 154(b) by 0 days.

(21) Appl. No.: 18/186,015

(22) Filed: Mar. 17, 2023

(65) Prior Publication Data
US 2023/0265490 A1    Aug. 24, 2023

Related U.S. Application Data

(63) Continuation-in-part of application No. PCT/US2022/075261, filed on Aug. 22, 2022.
(Continued)

(51) Int. Cl.
C12P 19/34    (2006.01)
C12Q 1/6818    (2018.01)
C12Q 1/6851    (2018.01)

(52) U.S. Cl.
CPC ......... *C12Q 1/6818* (2013.01); *C12Q 1/6851* (2013.01); *C12Q 2600/16* (2013.01); *C12Q 2600/178* (2013.01)

(58) Field of Classification Search
CPC .................................................. C12Q 1/6851
See application file for complete search history.

(56) References Cited

U.S. PATENT DOCUMENTS 7,799,522 B2    9/2010    Li
8,192,937 B2    6/2012    Jacobsen
(Continued)

FOREIGN PATENT DOCUMENTS

EP    0232967    8/1987
EP    2700719    2/2014
(Continued)

OTHER PUBLICATIONS

Androvic, et al., "Two-tailed RT-qPCR: a novel method for highly accurate miRNA quantification", Nucleic Acids Res., 45(15):e144 (2017).
(Continued)

*Primary Examiner* — Kenneth R Horlick
(74) *Attorney, Agent, or Firm* — PABST PATENT GROUP LLP

(57) ABSTRACT

Compositions and methods for quantitative detection of target nucleic acids, such as miRNAs are disclosed. The methods are especially advantageous for single-color multiplex detection of two or more targets simultaneously (e.g., in the same reaction). The methods can involve optional reverse transcription followed by amplification performed with universal primers, fluorophore-labeled detection probes, and quencher oligonucleotides for quenching fluorescence of any detection probe not bound to a target molecule. The methods employ differential stability of detection probe-quencher oligonucleotide complexes, and by extension, differential fluorescence at various temperatures to distinguish between different target molecules.

30 Claims, 25 Drawing Sheets

Specification includes a Sequence Listing.

Related U.S. Application Data

(60) Provisional application No. 63/235,522, filed on Aug. 20, 2021.

(56) References Cited

U.S. PATENT DOCUMENTS

| | | | |
|---|---|---|---|
| 8,586,718 | B2 | 11/2013 | Benson |
| 8,822,673 | B2 | 9/2014 | Chou |
| 10,017,761 | B2 | 7/2018 | Weissman |
| 10,590,469 | B2 | 3/2020 | Gupta |
| 10,876,160 | B2 * | 12/2020 | Hosaka ............... C12Q 1/6816 |
| 2004/0253593 | A1 * | 12/2004 | Cai ..................... C12Q 1/6823 435/6.11 |
| 2011/0151459 | A1 | 6/2011 | Rothmann |
| 2014/0080726 | A1 * | 3/2014 | Prakash ............... C12Q 1/6837 506/9 |
| 2014/0194611 | A1 | 7/2014 | Cook |
| 2014/0349295 | A1 | 11/2014 | Hosaka |
| 2014/0378330 | A1 | 12/2014 | Petrauskene |
| 2016/0177376 | A1 | 6/2016 | Tan |
| 2016/0265031 | A1 * | 9/2016 | Liu ..................... C12Q 1/6806 |
| 2020/0149091 | A1 | 5/2020 | Liu |

FOREIGN PATENT DOCUMENTS

| | | |
|---|---|---|
| WO | 2001042505 | 6/2001 |
| WO | 2001086001 | 11/2001 |
| WO | 2008040355 | 4/2008 |
| WO | 2011159256 | 12/2011 |

OTHER PUBLICATIONS

Armand-Labit, et al., "Circulating cell-free microRNAs as clinical cancer biomarkers", Biomol. Concepts, 8(2):61-81 (2017).
Bala, et al., "Circulating microRNAs in exosomes indicate hepatocyte injury and inflammation in alcoholic, drug-induced, and inflammatory liver diseases", Hepatol. Baltim. Md., 56(5):1946-57 (2012).
Botes, et al., "Application of quantitative PCR for the detection of microorganisms in water", Analytical and Bioanalytical Chemistry, 405(1):91-108 (2012).
Cao, et al., "Xpert MTB/XDR: a 10-Color Reflex Assay Suitable for Point-of-Care Settings To Detect Isoniazid, Fluoroquinolone, and Second-Line-Injectable-Drug Resistance Directly from *Mycobacterium tuberculosis*-Positive Sputum", J Clin Microbiol., 59(3) (2021).
Chen, et al., "Real-time quantification of microRNAs by stem-loop RT-PCR", Nucleic Acids Research, 33(20):e179 (2005).
Diaz-Sanchez, et al., "Development and application of a multiplex TaqMan real-time qPCR assay for the simultaneous detection of Anaplasma marginale and Theileria annulata and molecular characterization of Anaplasma marginale from cattle in Western Cuba", Ticks and Tick-Borne Diseases, 11(2) (2019).
Ellwood, et al., "Strand displacement applied to assays with nucleic acid probes", Clin. Chem., 32(9):1631-6 (1986).
Forero, et al., "qPCR-based methods for expression analysis of miRNAs", Bio Techniques, 67(4):192-199 (2019).
Ginzinger, et al., "Gene Quantification using real-time quantitative PCR: An emerging technology hits the mainstream", Experimental Hematology, 30:503-513 (2002).
Gubala, et al., "Molecular-Beacon Multiplex Real-Time PCR Assay for Detection of Vibrio cholerae", Applied and Environmental Microbiology, 72(9):6424-6428 (2006).
Huang, et al., "Quantification of Mature MicroRNAs Using Pincer Probes and Real-Time PCR Amplification", PLos One, 10(3):e0120160 (2015).
Huang, et al., "Thermodynamically modulated paritally double-stranded kinear DNA probe design for homogeneous real-time PCR", Nucelic Acids Research, 35(16):e101 (2007).
Iftikhar, et al., "Evidence and potential in vivo functions for biofluid miRNAs: From expression profiling to functional testing: Potential roles of extracellular miRNAs as indicators of physiological change and as agents of intercellular information exchange", Bioessays, 38(4):367-78 (2016).
Iwobi, et al., "A multiplex real-time PCR method for the quantitative determination of equine (horse) fractions in meat products", Food Control, 74:89-97 (2016).
Jacky, et al., "Robust Multichannel Encoding for Highly Multiplexed Quantitative PCR", Anal. Chem., 93(9):4208-4216 (2021).
Jin, et al., "Circulating microRNAs as Potential Diagnostic and Prognostic Biomarkers in Hepatocellular Carcinoma", Sci. Rep., 9(1):10464 (2019).
Kaczmarek, et al., "Profiling circulating microRNAs in the serum of pregnant and non-pregnant pigs reveals a plethora of reproductive status-dependent microRNAs", Animal, 15(4):100182 (2021).
Kolpashchikov, et al., "An Elegant Biosensor Molecular Beacon Probe: Challenges and Recent Solutions", Hindawi Publishing Corporation, 2012(928783):1-73 (2012).
Lee, et al., "Single-channel multiplexing without melting curve analysis in real-time PCR", Sci. Rep., 11(4):7439 (2014).
Li, et al., "A new class of homogeneous nucleic acid probes based on specific displacement hybridization", Nucleic Acids Res., 30(2):E5 (2002).
Lin, et al., "A serum microRNA classifier for early detection of hepatocellular carcinoma: a multicentre, retrospective, longitudinal biomarker identification study with a nested case-control study", Lancet Oncol., 16(7):804-15 (2015).
Mao, et al., "Principles of digital PCR and its applications in current obstetrical and gynecological diseases", Am. J. Transl. Res., 11(12):7209-7222 (2019).
Marras, et al., "Efficiencies of fluorescence resonance energy transfer and contact-mediated quenching in oligonucleotide probes", Nucleic Acids Res., 30(21):e122 (2002).
Mitchell, et al., "Circulating microRNAs as stable blood-based markers for cancer detection", PNAS, 105(30):10513-8 (2008).
Morrison, et al., "Solution-phase detection of polynucleotides using interacting fluorescent labels and competitive hybridization", Anal Biochem., 183(2):231-44 (1989).
Obande, "Current and Future Perspectives on Isothermal Nucleic Acid Amplification Technologies for Diagnosing Infections", Infect Drug Resist., 13:455-483 (2020).
Partial International Search report and Written Opinion for PCT/US2022/075261 dated Dec. 12, 2022.
Peleg, et al., "Multiplex real-time qPCR for the detection of Ehrlichia canis and Babesia canis vogeli", Veterinary Parasitology, 173(3-4):292-299 (2010).
Raymond, et al., "Simple, quantitative primer-extension PCR assay for direct monitoring of microRNAs and short-interfering RNAs", RNA, 11:1737-1744 (2005).
Reid, et al., "Circulating microRNAs: Association with disease and potential use as biomarkers", Crit. Rev. Oncol. Hematol., 80(2):193-208 (2011).
Remainder of International Search Report and Written Opinion for corresponding PCT/US2022/075261 dated Mar. 24, 2023.
Saidac, et al., "Detection and quantification of Lyme spirochetes using sensitive and specific molecular beacon probes", BMC Microbiology, Biomed Central Ltd, 9(1):43 (2009).
Shajari, et al., "Ribonucleic-acid-biomarker candidates for early-phase group detection of common cancers", Genomics, 112(1):163-168 (2020).
Starlinger, et al., "Predicting Postoperative Liver Dysfunction Based on Blood-Derived MicroRNA Signatures", Hepatol. Baltim. Md., 69(6):2636-51 (2019).
Takacs, et al., "Molecular beacon-based real-time PCR method for detection of 15 high-risk and 5 low-risk HPV types", Journal of Virological Methods, 149(1):153-162 (2008).
Tyagi, et al., "Molecular beacons in diagnostics", F1000 Med. Rep., 4:10 (2012).
Tyagi, et al., "Molecular beacons: probes that fluoresce upon hybridization", Nat. Biotechnol., 14(3):303-8 (1996).
Weiland, et al., "Small RNAs have a large impact: circulating microRNAs as biomarkers for human diseases", RNA Biol., 9(6):850-9 (2012).
Whale, et al., "Fundamentals of multiplexing with digital PCR", Biomol. Detect. Quantif., 10:15-23 (2016).

(56) References Cited

OTHER PUBLICATIONS

Yanez-Mo, et al., "Biological properties of extracellular vesicles and their physiological functions", J. Extracell. Vesicles., 4: 27066 (2015).

Yang, et al., "Development of a TaqMan MGB RT-PCR assay for the detection of type A and subtype H10 avian influenza viruses", Archives of Virology, 163(9):2497-2501 (2018).

Yang, et al., "Universal Stem-Loop Primer Method for Screening and Quantification of MicroRNA", PLOS One, 9(12):e115293 (2014).

Yang, et al., "Application of Molecular Beacons in Real-Time PCR," Molecular Beacons, :45-59 (2013).

Zhao, et al., "Isothermal Amplification of Nucleic Acids", Chem Rev., 115(22):12491-545 (2015).

\* cited by examiner

SEQUENCE LISTING

```
Sequence total quantity: 24
SEQ ID NO: 1              moltype = RNA  length = 22
FEATURE                   Location/Qualifiers
source                    1..22
                          mol_type = other RNA
                          organism = synthetic construct
SEQUENCE: 1
tgtcagtttg tcaaataccc ca                                              22

SEQ ID NO: 2              moltype = RNA  length = 22
FEATURE                   Location/Qualifiers
source                    1..22
                          mol_type = other RNA
                          organism = synthetic construct
SEQUENCE: 2
tagcagcacg taaatattgg cg                                              22

SEQ ID NO: 3              moltype = RNA  length = 22
FEATURE                   Location/Qualifiers
source                    1..22
                          mol_type = other RNA
                          organism = synthetic construct
SEQUENCE: 3
tcaccgggtg taaatcagct tg                                              22

SEQ ID NO: 4              moltype = DNA  length = 43
FEATURE                   Location/Qualifiers
source                    1..43
                          mol_type = other DNA
                          organism = synthetic construct
SEQUENCE: 4
tgcaataaat cccgcatgct cgacgcagtc cctcacatgg ggt                       43

SEQ ID NO: 5              moltype = DNA  length = 43
FEATURE                   Location/Qualifiers
source                    1..43
                          mol_type = other DNA
                          organism = synthetic construct
SEQUENCE: 5
tgcaataaat cccgcatgct cgacgcagtc cctcacacgc caa                       43

SEQ ID NO: 6              moltype = DNA  length = 43
FEATURE                   Location/Qualifiers
source                    1..43
                          mol_type = other DNA
                          organism = synthetic construct
SEQUENCE: 6
tgcaataaat cccgcatgct cgacgcagtc cctcacacaa gct                       43

SEQ ID NO: 7              moltype = DNA  length = 12
FEATURE                   Location/Qualifiers
source                    1..12
                          mol_type = other DNA
                          organism = synthetic construct
misc_feature              12
                          note = 3' phosphorylation
SEQUENCE: 7
tgtgagggac tg                                                         12

SEQ ID NO: 8              moltype = DNA  length = 27
FEATURE                   Location/Qualifiers
source                    1..27
                          mol_type = other DNA
                          organism = synthetic construct
misc_feature              1
                          note = conjugated to fluorescein (FAM) fluorescent dye
misc_feature              27
                          note = 3' Phosphorylation
SEQUENCE: 8
aggcacgcag gctgtcagtt tgtcaaa                                         27

SEQ ID NO: 9              moltype = DNA  length = 25
FEATURE                   Location/Qualifiers
source                    1..25
                          mol_type = other DNA
                          organism = synthetic construct
misc_feature              1
                          note = conjugated to fluorescein (FAM) fluorescent dye
```

```
misc_feature        25
                    note = 3' Phosphorylation
SEQUENCE: 9
aggcacgcat agcagcacgt aaata                                          25

SEQ ID NO: 10       moltype = DNA  length = 22
FEATURE             Location/Qualifiers
source              1..22
                    mol_type = other DNA
                    organism = synthetic construct
misc_feature        1
                    note = conjugated to fluorescein (FAM) fluorescent dye
misc_feature        22
                    note = 3' Phosphorylation
SEQUENCE: 10
aggcacgtca ccgggtgtaa at                                             22

SEQ ID NO: 11       moltype = DNA  length = 12
FEATURE             Location/Qualifiers
source              1..12
                    mol_type = other DNA
                    organism = synthetic construct
misc_feature        12
                    note = conjugated to BHQ1 quencher
SEQUENCE: 11
gcctgcgtgc ct                                                        12

SEQ ID NO: 12       moltype = DNA  length = 20
FEATURE             Location/Qualifiers
source              1..20
                    mol_type = other DNA
                    organism = synthetic construct
SEQUENCE: 12
gcgctatccg acaatttcca                                                20

SEQ ID NO: 13       moltype = DNA  length = 20
FEATURE             Location/Qualifiers
source              1..20
                    mol_type = other DNA
                    organism = synthetic construct
SEQUENCE: 13
taaatcccgc atgctcgacg                                                20

SEQ ID NO: 14       moltype = DNA  length = 52
FEATURE             Location/Qualifiers
source              1..52
                    mol_type = other DNA
                    organism = synthetic construct
SEQUENCE: 14
agtcgcgcta tccgacaatt tccaatatca ggcacgcagg ctgtcagttt gt            52

SEQ ID NO: 15       moltype = DNA  length = 48
FEATURE             Location/Qualifiers
source              1..48
                    mol_type = other DNA
                    organism = synthetic construct
SEQUENCE: 15
agtcgcgcta tccgacaatt tccaatatca ggcacgcata gcagcacg                 48

SEQ ID NO: 16       moltype = DNA  length = 45
FEATURE             Location/Qualifiers
source              1..45
                    mol_type = other DNA
                    organism = synthetic construct
SEQUENCE: 16
agtcgcgcta tccgacaatt tccaatatca ggcacgtcac cgggt                    45

SEQ ID NO: 17       moltype = DNA  length = 29
FEATURE             Location/Qualifiers
source              1..29
                    mol_type = other DNA
                    organism = synthetic construct
misc_feature        1
                    note = conjugated to fluorescein (FAM) fluorescent dye
misc_feature        29
                    note = 3' Phosphorylation
SEQUENCE: 17
aggcacgtca ccgggtgtaa atcagcttg                                      29
```

```
SEQ ID NO: 18            moltype = DNA  length = 31
FEATURE                  Location/Qualifiers
source                   1..31
                         mol_type = other DNA
                         organism = synthetic construct
misc_feature             1
                         note = conjugated to fluorescein (FAM) fluorescent dye
misc_feature             31
                         note = 3' Phosphorylation
SEQUENCE: 18
aggcacgcat agcagcacgt aaatattggc g                                   31

SEQ ID NO: 19            moltype = DNA  length = 34
FEATURE                  Location/Qualifiers
source                   1..34
                         mol_type = other DNA
                         organism = synthetic construct
misc_feature             1
                         note = conjugated to fluorescein (FAM) fluorescent dye
misc_feature             34
                         note = 3' Phosphorylation
SEQUENCE: 19
aggcacgcag gctgtcagtt tgtcaaatac ccca                                34

SEQ ID NO: 20            moltype = DNA  length = 91
FEATURE                  Location/Qualifiers
source                   1..91
                         mol_type = other DNA
                         organism = synthetic construct
SEQUENCE: 20
tagtcgcgct atccgacaat ttccaaatta tcaggcacgt caccgggtgt aaatcagctt    60
ggtagcgtcg agcatgcggg atttattgca t                                   91

SEQ ID NO: 21            moltype = DNA  length = 93
FEATURE                  Location/Qualifiers
source                   1..93
                         mol_type = other DNA
                         organism = synthetic construct
SEQUENCE: 21
tagtcgcgct atccgacaat ttccaaatta tcaggcacgc atagcagcac gtaaatattg    60
gcggtagcgt cgagcatgcg ggatttattg cat                                 93

SEQ ID NO: 22            moltype = DNA  length = 96
FEATURE                  Location/Qualifiers
source                   1..96
                         mol_type = other DNA
                         organism = synthetic construct
SEQUENCE: 22
tagtcgcgct atccgacaat ttccaaatta tcaggcacgc aggctgtcag tttgtcaaat    60
accccagtag cgtcgagcat gcgggattta ttgcat                              96

SEQ ID NO: 23            moltype = DNA  length = 91
FEATURE                  Location/Qualifiers
source                   1..91
                         mol_type = other DNA
                         organism = synthetic construct
SEQUENCE: 23
tagtcgcgct atccgacaat ttccaaatta tcacggcagt caccgggtgt aaatcagctt    60
ggtagcgtcg agcatgcggg atttattgca t                                   91

SEQ ID NO: 24            moltype = DNA  length = 93
FEATURE                  Location/Qualifiers
source                   1..93
                         mol_type = other DNA
                         organism = synthetic construct
SEQUENCE: 24
tagtcgcgct atccgacaat ttccaaatta tcagcgagcc atagcagcac gtaaatattg    60
gcggtagcgt cgagcatgcg ggatttattg cat                                 93
```

METHODS FOR MULTIPLEX DETECTION OF POLYNUCLEOTIDES USING UNBOUND FLUORESCENT PROBES AND QUENCHER OLIGONUCLEOTIDES

CROSS-REFERENCE TO RELATED APPLICATIONS

This application is a continuation-in-part of PCT/US2022/075261 filed Aug. 22, 2022, which claims the benefit of and priority to U.S. Ser. No. 63/235,522 filed Aug. 20, 2021, and each which is specifically incorporated by reference in its entirety.

REFERENCE TO SEQUENCE LISTING

The Sequence Listing submitted as an xml file named "KASA100PCT_ST25.xml," created on Aug. 22, 2022, and having a size of 28,119 bytes, is hereby incorporated by reference pursuant to 37 C.F.R § 1.834(c)(1).

FIELD OF THE INVENTION

The field of the invention generally relates to compositions and methods for quantitative detection of miRNAs and other polynucleotides, and uses related thereto.

BACKGROUND OF THE INVENTION

MicroRNAs (miRNAs) are non-coding single-stranded RNAs of ~22-nucleotides in length that regulate gene expression and play regulatory roles in various biological processes, including embryo development, cell differentiation, proliferation, apoptosis, cellular stress response, and immunoregulation. Dysregulation of miRNAs is implicated in pathologies of many human diseases such as cancer, muscle disorders and neurodegeneration. In recent years, circulating cell-free microRNAs (miRNAs) have emerged as promising biomarkers for the development of blood-based assays for early detection, prognosis and monitoring of diseases (Mitchell P S, et al. Proc Natl Acad Sci USA., 105(30):10513-8 (2008); Iftikhar H, Carney G E., Bioessays, 38(4):367-78 (2016)). Based on their extraordinary stability, less complex chemical structure and their lack of post-processing modifications, circulating miRNAs are suggested as "optima liquid biopsy" biomarkers (Armand-Labit V, et al., Biomol Concepts, 8(2):61-81 (2017); Reid G., et al., Crit Rev Oncol Hematol., 80(2):193-208 (2011). Accumulating evidence supports the use of circulating miRNAs as non-invasive biomarkers (Reid G., et al.; Shajari E, Mollasalehi H., Genomics, 112(1):163-168 (2020); Weiland M, et al., RNA Biol., 9:850-9 (2012)), including that of the liver diseases (Starlinger P, et al., Hepatol Baltim Md., 69:2636-51 (2019); Jin Y, et al., Sci Rep, 9:10464 (2019); Bala S, et al., Hepatol Baltim Md., 56:1946-57 (2012); Lin X-J, et al., Lancet Oncol., 16:804-15 (2015);). There are three most commonly used techniques to measure miRNA expression: hybridization-based approaches such as microarrays, next generation sequencing (RNA-seq), and reverse transcription quantitative PCR (RT-qPCR). RT-qPCR is the gold standard molecular method because it is easy to use, shows higher sensitivity and provides a well-established workflow (Androvic P, et al., Nucleic Acids Res., 45(15):e144 (2017)). Current commercial methods on reverse transcription of miRNA use either an miRNA specific stem-loop RT primer (ThermoFisher Scientific), polyadenylation followed by RT using oligo(dT) primer with a tag (QIAGEN, and Takara Bio) or poly A tailing and 5' adapter ligation followed by RT using universal primer (TaqMan Advanced miRNA Assays by ThermoFisher Scientific).

Though these methods are widely used in research and clinical labs, they can detect only one miRNA per qPCR reaction thus requiring multiple qPCR reactions to quantify multiple miRNAs. In addition, the stem-loop method may have different PCR efficiencies depending on the miRNA target leading to quantification bias and also a lack of specificity. The poly(A) tailing and/or adapter ligation modifications methods are not 100% efficient and require higher input miRNA, which is a challenge in the clinical setting, especially when using plasma or serum. The NGS-based method is costly, involves many steps (library preparation, sequencing by synthesis, and analysis pipeline) leading to longer turn-around time, and requires skilled personnel for analyses and interpretation, thus making it difficult for clinical adoption.

Furthermore, currently, the most advanced qPCR systems can detect only up to 4-6 targets (one target per fluorescent channel) in total in a single PCR reaction due to the limited availability of fluorescent channels with minimal spectral crosstalk. Many research and clinical applications require detection or measurement of multiple DNA or RNA targets (>6) in a single reaction to reduce the cost, turnaround time, and bias and increase the accuracy. Applications like syndromic testing (respiratory infections, gastrointestinal infections, sepsis, etc.) and gene signature analysis require detection of multiple DNA or RNA targets in single PCR reaction. However, as with qPCR, multiplexed detection in digital PCR (dPCR) and isothermal amplification are also limited by the availability of fluorescent channels.

Current quantitative detection approaches using TaqMan Probes or Molecular Beacons or Double-stranded probes measure the quantity of amplified product formed at each qPCR cycle.

There remains a need for alternative methods for detection of multiple polynucleotides (e.g., miRNAs) that are specific, sensitive, and cost-effective preferably while increasing the capacity of widely adapted qPCR technology and emerging dPCR or isothermal technologies.

Thus, it is an object of the invention to provide alternative methods for quantitative detection of multiple polynucleotides (e.g., DNA or RNA).

It is a further object of the invention to provide methods with improved sensitivity, specificity, and/or efficiency in miRNA quantification.

It is another object of the invention to provide high-throughput methods for concurrent detection of multiple target polynucleotides, including miRNAs.

It is another object of the invention to provide methods for detection of biomarkers for the diagnosis and/or prognosis of diseases.

SUMMARY OF THE INVENTION

Compositions and methods for detection and/or quantification of targets, such as polynucleotides are disclosed. The methods are especially advantageous for quantitative multiplex detection of two or more targets simultaneously (e.g., in the same color or fluorescent channel; detection of e.g., 10-15 targets on a qPCR or other amplification system with 5 fluorescent channels). The compositions and methods utilize a fluorescent probe/quencher oligo relationship, whereby a fluorescent probe or primer in close proximity to (e.g., hybridized or otherwise bound to) the quencher oligo is dark (i.e., quenched), and when free from the quencher oligo, e.g., free in solution or bound to a target nucleic acid is fluorescent (i.e., unquenched).

Fluorescence of free (unbound or unutilized) probes is affected by the melting temperature of quencher oligo and fluorescent probe sequence complex, and amplicons of the same color can be differentiated based on the melt difference among the quencher and fluorescent oligo complexes. The length and extent of complementarity between quencher oligo and fluorescent probe oligo affect the melting temperature and thus the amount of fluorescence. Amount of plurality of free fluorescent probes (e.g., not bound to the complementary template) is measured at different pre-designed melting temperatures followed by use of fluorescent data to determine and quantify multiple targets. For example, after denaturation step e.g., at 95° C. in a qPCR system, the reaction is cooled down, e.g., to 24° C. This allows hybridization of probe specifically to its respective target, first during the cooling step, followed by quencher binding to any free probes. Then the reaction is heated to one or more predetermined temperatures, e.g., 44° C., 58° C., and 72° C. which destabilizes quencher and free probe binding, depending on the length/extent of complementarity. When the temperature increases to 44° C., unbound probe to a third target fully dissociates from quencher whereas unbound probe to a first and second target are still quenched. When the temperature increases to 58° C., unbound probes to the second and third targets fully dissociate from the quencher whereas unbound probe to the first target is still quenched. When the temperature increases to 72° C., unbound probes first, second, and third target fully dissociates from the quencher. The difference in fluorescence intensity at these temperatures are used to differentiate targets amplified in the same color. As discussed in more detail below, these temperatures are illustrative and non-limiting.

At every cycle, the amount of unbound probe or primer binding to specific target is measured by a temperature protocol that facilitates unbound probe and quencher complex association and dissociation. After the run is completed, the fluorescence data is deconvoluted, and an amplification curve is generated for each target.

By using multiple different colored fluorophores in combination with probes or primers having varied melting temperatures (unbound primer or probe and quencher oligo complex), the number of targets measured in a single reaction can be further increased.

The compositions and methods stemming from this strategy provide improved, sensitive, specific, and cost-effective PCR-based assays with reduced bias for target detection and/or quantification.

Thus, compositions and methods for the multiplex detection of any polynucleotide by measuring the quantity of unbound fluorescent-labelled primers or fluorescent-labelled probes are provided. In some embodiments, a method for qualitative or quantitative detection of two or more distinct target polynucleotides in a sample involves performing real-time qPCR or other method of amplification on the sample (e.g., using universal or target-specific forward and reverse primers) to generate amplified products corresponding to the target polynucleotides, and detecting and/or quantifying each amplified product by measuring the plurality of distinct detection probes that are unbound to the amplified DNA (free or unused probes) and a plurality of quencher oligonucleotides at each cycle (e.g., qPCR, digital PCR cycle).

In some embodiments, each detection probe in the plurality of detection probes includes an identical fluorophore, a tag different in sequence and/or size from that of other distinct probes in the plurality of detection probes, and a target-specific sequence that is complementary to and can hybridize to a target amplified product.

In some embodiments, the detection probe is a primer wherein the plurality of primers includes the same or different fluorophore, a tag different in sequence and/or size from that of other distinct primers in the plurality of primers, and a target-specific sequence that is complementary to and can hybridize to a specific target to prime the amplification (e.g., PCR reaction, digital PCR, or isothermal amplification).

In some embodiments, each detection probe in the plurality of detection probes includes an identical fluorophore with a target-specific sequence that is fully complementary to and can hybridize to a target amplified product.

In some embodiments, the plurality of quencher oligonucleotides includes an identical fluorescence quencher and an identical tag-binding sequence (that is partially or fully complementary to the tag of each detection probe). In such embodiments, it is contemplated that multiple distinct target amplicons can be differentiated by the length/extent of complementarity to the tag-binding sequence of the quencher oligonucleotides, which can influence the melting temperature of the respective detection probe-quencher oligonucleotide complexes.

In some embodiments, for each distinct detection probe, the plurality of quencher oligonucleotides includes a quencher oligonucleotide that is fully complementary to distinct detection probe, wherein each quencher oligonucleotide in the plurality of quencher oligonucleotides contains an identical fluorescence quencher.

In some embodiments, for each distinct detection probe, the plurality of quencher oligonucleotides includes a quencher oligonucleotide that is fully complementary to the distinct detection probe, wherein each quencher oligonucleotide in the plurality of quencher oligonucleotides contains an identical fluorescence quencher. In such embodiments, it is contemplated that multiple distinct target amplicons can be differentiated by the length/extent of complementarity of the quencher oligonucleotides, which can influence the melting temperature of the respective detection probe-quencher oligonucleotide complexes.

In some embodiments, the plurality of detection probes includes two or more groups of detection probes. In some embodiments, each group of detection probes includes an identical fluorophore across all the probes in the group. Preferably, each distinct detection probe in a group contains a tag different in sequence and/or size from that of other probes in the group, and a target-specific sequence that is complementary to and hybridizes to a distinct target amplified product. In some embodiments, each group of detection probes includes 3-4 distinct detection probes (e.g., the ability to detect 3-4 distinct target polynucleotides such as miRNAs within the same color).

In some embodiments, for each group of detection probes, the plurality of quencher oligonucleotides includes an identical fluorescence quencher and an identical tag-binding sequence that is partially or fully complementary to the tags of the detection probes in the group.

In some embodiments, for each distinct detection probe, the plurality of quencher oligonucleotides includes a quencher oligonucleotide containing a tag-binding sequence that is fully complementary to the tag of the distinct detection probe, and for each group of detection probes, each quencher oligonucleotide in the plurality of quencher oligonucleotides includes an identical fluorescence quencher.

In preferred embodiments, the quencher oligonucleotides are capable of hybridizing to each distinct detection probe to form a plurality of unique detection probe-quencher oligonucleotide complexes. Preferably, each detection probe-quencher oligonucleotide complex exhibits a unique melting temperature (e.g., depending on the base composition and/or amount of hybridization or complementarity between the tag of the detection probe and the tag-binding sequence of the quencher oligonucleotide for each complex). In some embodiments, formation of the detection probe-quencher oligonucleotide complex results in quenching of fluorescence from the fluorophore by the fluorescence quencher, and fluorescence can be unquenched at a temperature above the unique melting temperature for each detection probe-quencher oligonucleotide complex.

For each amplification (e.g., qPCR, dPCR) cycle, fluorescence can be measured at each unique melting temperature and optionally, during the annealing step (e.g., when the universal forward and reverse primers anneal to the denatured DNA template). Fluorescence deconvolution data analysis can be used to differentiate between each amplified product. For example, in some embodiments, the amplified product corresponding to each target polynucleotide can be distinguished and/or quantified by the amount of fluorescence measured at each temperature, e.g., using the signal deconvolution approach described herein.

In the case of dPCR, at the end of PCR cycle, fluorescence can be measured at each unique melting temperature(s) followed by fluorescence data deconvolution to differentiate between amplified products. For example, in some embodiments, the amplified product corresponding to each target polynucleotide can be distinguished and/or quantified by the amount of fluorescence measured at each temperature, e.g., using the signal deconvolution approach described herein.

In case of isothermal amplification, at the end of the reaction, fluorescence can be measured at each unique melting temperature followed by fluorescence data deconvolution to differentiate between amplified products. For example, in some embodiments, the amplified product corresponding to each target polynucleotide can be distinguished and/or quantified by the amount of fluorescence measured at each temperature, e.g., using the signal deconvolution approach described herein. This is the same as in qualitative PCR with a first and last cycle being the performance of a temperature incubation step to determine co-amplified targets using fluorescence deconvolution. It is not at every cycle but only at the beginning and at the end of the amplification reaction. The process can nonetheless be used to determine co-amplification of multiple targets in the same color.

Also provided are methods for the multiplex detection of polynucleotides using molecular beacons. In some embodiments, a method for detection of two or more distinct target polynucleotides in a sample involves performing real-time qPCR (or digital PCR, or isothermal amplification)) on the sample (e.g., using universal or target-specific forward and reverse primers) to generate amplified products corresponding to the target polynucleotides, and detecting and/or quantifying each amplified product using a plurality of distinct molecular beacons.

In some embodiments, for each distinct target polynucleotide, the plurality of distinct molecular beacons includes a molecular beacon containing a target-specific sequence that is complementary to and/or hybridizes to the amplified product corresponding to the target polynucleotide. Each molecular beacon in the plurality of molecular beacons can include the identical fluorophore and the identical fluorescence quencher.

Typically, in the absence of (or when not bound to) the target polynucleotide or the corresponding amplified product, each molecular beacon self-hybridizes to form a hairpin (stem-loop) structure. In preferred embodiments, each hairpin structure exhibits a unique melting temperature. Formation of the hairpin structure can result in quenching of fluorescence from the fluorophore by the fluorescence quencher, and as such, fluorescence can be unquenched at a temperature above the unique melting temperature for each hairpin structure. In some embodiments, fluorescence is measured at each unique melting temperature for each amplification (e.g., qPCR, digital PCR, or isothermal amplification) cycle. Resultantly, the amplified products corresponding to the two or more target polynucleotides can be detected and/or distinguished by the amount of fluorescence measured at each temperature, e.g., using the signal deconvolution approach described herein.

In any of the foregoing methods, the fluorophore can be selected from fluorescein (FAM™), hexachloro-fluorescein (HEX™), 2-chloro-7'-phenyl-1,4-dichloro-6-carboxy-fluorescein (VIC®), 5'-Dichloro-Dimethoxy-Fluorescein (JOE™), tetrachlorofluorescein (TET™), SUN™ tetramethylrhodamine (TAMRA™), QUASAR®670, CAL Fluor® Orange (CF560), CAL Fluor® Red 610 (CF610), Texas Red® (Sulforhodamine 101 acid chloride) and/or the fluorescence quencher can be selected from Black Hole Quencher®-1 (BHQ®-1), Black Hole Quencher®-2 (BHQ®-2), and Black Hole Quencher®-3 (BHQ®-3).

The method can also be used to increase the capacity of digital PCR or isothermal amplification systems.

Exemplary target polynucleotides that can be detected and/or quantified by the foregoing methods include DNA (e.g., genomic or mitochondrial DNA) and RNA. In some embodiments, when the target polynucleotide is RNA, the real-time qPCR or other amplification can be preceded by reverse transcription of the RNA. In some embodiments, the RNA can be small nucleolar RNA, messenger RNA (mRNA), small interfering RNA (siRNA), microRNA, or antisense RNA.

Exemplary miRNAs that can be detected by any of the disclosed methods include, without limitation, miR-122, miR-192, miR-21, miR-223, miR-375, miR-30a, miR-33a, miR-34a, miR-16, miR-155, miR-132, miR-27a, miR-150, miR-199, miR-200, miR-17, miR-214, miR-9, miR-29a, miR-212, miR-214, miR-497, miR-378, miR-320, miR-222, miR-106a, miR-92, miR-20, miR-23, miR-18, miR-126, and Cel-miR-39.

Also, disclosed separately and in combination with the disclosed detection compositions and methods, are methods for quantitative detection of target miRNA, involving: (a) bringing into contact a sample containing RNA with a single-stranded reverse transcription (RT) primer and optionally a blocker oligonucleotide under conditions suitable for the RT primer to hybridize to a target mature miRNA and (b) performing reverse transcription to obtain cDNA. Typically, the RT primer includes in the 5' to 3' direction, (i) a tag collectively containing a universal reverse primer sequence and a binding site for the blocker oligonucleotide, and (ii) a sequence (e.g., 4-8 bps) complementary to the 3'-end of the target miRNA. The method can further involve (c) amplifying the cDNA by PCR using a first PCR primer and the RT primer to generate double-stranded DNA template, wherein the first PCR primer contains in the 5' to 3' direction, a universal forward primer sequence, a tag, and a sequence corresponding to the 5'-end of the target miRNA, and (d) performing real-time quantitative PCR (qPCR) or digital PCR, or isothermal amplification on the DNA template to generate an amplified product corresponding to the target miRNA, and detecting and/or quantifying the amplified product optionally by measuring amount of unbound or unutilized probe at each amplification cycle.

In some embodiments (specifically for detection of mature miRNAs), the blocker oligonucleotide hybridizes to the RT primer at the binding site for the blocker oligonucleotide. In some embodiments, the blocker oligonucleotide hybridizes to the RT primer adjacent to the 3'-end of the target miRNA before the target miRNA is hybridized to the RT primer. In some embodiments, the blocker oligonucleotide contains about 12-16 nucleotides.

In some embodiments, amplification of the cDNA in step (c) involves about 1-10 PCR cycles. The sequence in the RT primer complementary to the 3'-end of the target miRNA can include about 4-8 nucleotides. In some embodiments, the sequence in the first PCR primer corresponding to the 5'-end of the target miRNA can include about 10-16 nucleotides.

The real-time qPCR or other amplification strategy can be performed using a universal forward primer and a universal reverse primer. In some embodiments, the universal forward primer contains the universal forward primer sequence of the first PCR primer and the universal reverse primer contains the universal reverse primer sequence of the RT primer.

Preferably, the real-time qPCR or other amplification strategy such digital PCR or isothermal amplification is performed in the presence of a detection probe and a quencher oligonucleotide. In all embodiments discussed herein, detection probe and quencher oligonucleotides can be unlinked or linked. Thus, in some embodiments, the detection probe and quencher oligonucleotide are separate oligonucleotide molecules. In other embodiments, the detection probe and quencher oligonucleotide are a single oligonucleotide molecule. As discussed in more detail elsewhere herein, in some embodiments, the detection probe and quencher oligonucleotide can form a hairpin by self-hybridization. In particular embodiments, linked detection probe and quencher oligonucleotide that form a hairpin are referred to as a molecular beacon, which may also include additional sequence considerations as discussed herein to modulate binding to, and detection of, multiple targets with a single fluorophore (i.e., multiplex detection). Thus, in molecular beacons, the fluorophore and fluorescence quencher are on the same oligonucleotide.

In preferred embodiments, the detection probe includes a fluorophore, a first region containing the tag sequence (or a portion thereof) of the first PCR primer, and a second region containing a (miRNA-specific) sequence that is complementary to the amplified product. In preferred embodiments, the quencher oligonucleotide includes a fluorescence quencher (e.g., at the 3' end) and a sequence that is complementary to the first region of the detection probe. In some embodiments, the 3' end of the quencher oligonucleotide and/or the detection probe is blocked from being extendable by a polymerase. In some embodiments, the fluorophore is attached to the 5' or 3' end of the detection probe, preferably the 5' end, and/or the fluorescence quencher is attached to the 5' or 3' end of the quencher oligonucleotide, preferably the 3' end. Typically, the quencher oligonucleotide and the detection probe, whether linked (single oligonucleotide) or unlinked (two oligonucleotides), are capable of hybridizing to each other, and the hybridization can result in quenching of fluorescence from the fluorophore by the fluorescence quencher.

Preferably, the detection probe is capable of hybridizing to the DNA template or the amplified product corresponding to the target miRNA. The detection probe can be designed to hybridize to the DNA template or the amplified product at a higher temperature than the temperature at which the universal forward and universal reverse primers anneal to the DNA template or the amplified product. For example, the detection probe can be designed to have a Tm of greater than or equal to 72° C.

In some embodiments, the amplified product is detected and/or quantified by measuring fluorescence during the annealing step of each cycle (e.g., when the universal forward and reverse primers anneal to the denatured DNA template).

The disclosed method can also be used for quantitative or qualitative detection of two or more target miRNAs. For example, the method can permit multicolor multiplexing such that one distinct target is detected per fluorescent channel. In some embodiments, the method can involve using a plurality of RT primers, a plurality of first PCR primers, and a plurality of detection probes. Typically, for each target miRNA, (i) the plurality of RT primers includes an RT primer containing a sequence complementary to the 3'-end of the target miRNA, (ii) the plurality of first PCR primers includes a first PCR primer containing a sequence corresponding to the 5'-end of the target miRNA, (iii) the plurality of detection probes includes a detection probe containing a distinct fluorophore and a distinct second region containing a sequence complementary to the amplified product of the target miRNA, and optionally, (iv) measuring the quantity of unbound probes at each amplification cycle (e.g., qPCR cycle).

In some embodiments, each RT primer in the plurality of RT primers contains the same tag (e.g., collectively containing the same universal reverse primer sequence and blocker oligonucleotide binding site). In some embodiments, each first PCR primer in the plurality of first PCR primers contains the same universal forward primer sequence and the same tag (e.g., which can be the first region of the detection probe (complementary to quencher oligonucleotide)). In some embodiments, each detection probe in the plurality of detection probes contains the same first region that is complementary to the tag of the first PCR primer. In some embodiments, each detection probe can be quenched by the quencher oligonucleotide. For example, the quencher oligonucleotide can be a universal or common quencher oligonucleotide containing a common sequence that is complementary to the first region of the detection probe. Typically, the site at which the quencher binds to the probe is a non-target sequence that is incorporated through the First PCR primer as tagged sequence. In some embodiments, different fluorescence quenchers (e.g., BHQ®-1, BHQ®-2, or BHQ®-3) can be attached to the same common sequence contained in the universal or common quencher.

In some embodiments, a method for quantitative or qualitative detection of two or more target miRNAs involves using a plurality of RT primers, a plurality of first PCR primers, and a plurality of detection probes, wherein each detection probe in the plurality of detection probes contains the identical fluorophore. In preferred embodiments, for each target miRNA, (i) the plurality of RT primers includes an RT primer containing a sequence complementary to the 3'-end of the target miRNA; (ii) the plurality of first PCR primers includes a first PCR primer containing a sequence corresponding to the 5'-end of said target miRNA; and (iii) the plurality of detection probes includes a detection probe containing a first region that is distinct in sequence and/or size from other probes in the plurality of detection probes and a distinct second region comprising a sequence that is complementary to the amplified product of the target miRNA.

In some embodiments, the quencher oligonucleotide is capable of hybridizing to each distinct detection probe in the plurality of detection probes to form a plurality of unique detection probe-quencher oligonucleotide complexes. Preferably, the extent of complementarity/hybridization is different for each unique detection probe-quencher oligonucleotide complex. Each unique detection probe-quencher oligonucleotide complex can exhibit a unique melting temperature. In some embodiments, formation of the detection probe-quencher oligonucleotide complex results in quenching of fluorescence from the fluorophore by the fluorescence quencher, and fluorescence can be unquenched at a temperature above the unique melting temperature for each detection probe-quencher oligonucleotide complex. A similar strategy can be applied to molecular beacon technology, by adjusting the length/extent of complementarity of the stem region in the hairpin loop.

In some embodiments, fluorescence is measured at each unique melting temperature for each amplification (e.g., qPCR, digital PCR) cycle. In some embodiments, fluorescence is also measured during the annealing step of each cycle (e.g., when the universal forward and reverse primers anneal to the denatured DNA template). Fluorescence thus measured at different melting or annealing temperatures can be used to deconvolute the signal to determine the signal coming from specific detection probe and quencher oligonucleotide complexes. Also, the fluorescence measurements at different melting and annealing temperatures can be used to determine the detection probes that are not bound to the amplified product.

In some embodiments, fluorescence is measured at each melting temperature at the end of one or more, preferably all, amplification cycles to qualitatively determine the co-amplified targets by measuring the amount of unbound probes. Fluorescence is measured at each unique melting temperature for each amplification (e.g., quantitative PCR,) cycle or at the beginning and end of amplification step (e.g., qualitative PCR or digital PCR or isothermal amplification) as introduced above.

In some embodiments, a method for quantitative detection of two or more target miRNAs involves using a plurality of RT primers, a plurality of first PCR primers, a plurality of detection probes and a plurality of quencher oligonucleotides. In preferred embodiments, each detection probe in the plurality of detection probes contains the identical fluorophore. In preferred embodiments, for each target miRNA, (i) the plurality of RT primers includes an RT primer containing a sequence complementary to the 3'-end of the target miRNA, (ii) the plurality of first PCR primers includes a first PCR primer containing a sequence corresponding to the 5'-end of the target miRNA; and (iii) the plurality of detection probes includes a detection probe containing a first region that is distinct in sequence and/or size from other probes in the plurality of detection probes and a distinct second region containing a sequence that is complementary to the amplified product of the target miRNA.

In some embodiments, for each detection probe, the plurality of quencher oligonucleotides includes a quencher oligonucleotide containing a sequence that is complementary to the first region of the detection probe. In some embodiments, the quencher oligonucleotide is capable of hybridizing to the unbound detection probe (free detection probe not bound to a target, also referred to here as free probe and/or unutilized probe) to form a unique detection probe-quencher oligonucleotide complex. In some embodiments, for each detection probe, the corresponding detection probe-quencher oligonucleotide complex exhibits a unique melting temperature (e.g., that is distinct from the melting temperatures for other detection probe-quencher oligonucleotide complexes). Typically, formation of the detection probe-quencher oligonucleotide complex can result in quenching of fluorescence from the fluorophore by the fluorescence quencher, wherein fluorescence is unquenched at a temperature above the unique melting temperature for each detection probe-quencher oligonucleotide complex (e.g., due to full dissociation of the detection probe-quencher oligonucleotide complex at above the melting temperature).

In some embodiments, fluorescence is measured at each unique melting temperature for each cycle (e.g., qPCR digital PCR cycle) and optionally, during the annealing step of each cycle (e.g., when the universal forward and reverse primers anneal to the denatured DNA template). In some embodiments, the unique melting temperature(s) is predetermined by in silico analysis/experimental melting temperature between detection probe and quencher oligonucleotide.

In the foregoing methods for quantitative detection of two or more target miRNAs, fluorescence data analysis can be used to differentiate between each amplified product. For example, in some embodiments, the amplified product corresponding to each target miRNA can be distinguished and/or quantified by using the amount of fluorescence measured at each temperature. In some embodiments, differentiation of quantification is achieved by obtaining the difference in fluorescence at two temperatures.

In some embodiments, the sample contains size selected RNA (e.g., the sample can be enriched for short/small RNAs). In some embodiments, the target miRNA(s) can be associated with a disease or disorder. Exemplary diseases or disorders include cancer, cardiovascular diseases, liver diseases, sepsis, infectious diseases, genetic disorders, metabolic disorders, and neurodegenerative diseases. In some embodiments, the sample contains cell-free DNA or RNA, such as RNA derived from exosomes or other extracellular vehicle. In some embodiments, the DNA or RNA is from pathogenic bacteria, fungi or viruses, or circulating tumor cells.

Additional advantages of the disclosed methods will be set forth in part in the description which follows, and in part will be understood from the description, or can be learned by practice of the disclosed methods and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed methods and compositions and together with the description, serve to explain the principles of the disclosed method and compositions.

FIG. 1A shows the principle using an illustration and FIG. 1B is plot illustrating how the measured data is transformed to report the increase in amplified product over time. Unbound primer or probes are quenched (Tm<60) by contact quenching, and unused primer or probe are measure at each qPCR cycle (1A). Fluorescence values decrease with increasing cycle number (1B, left plot), which can be transformed into increasing values by subtracting fluorescent values from a reference number (1B, right plot). Double-strand or molecular beacons probe and primer designs can be utilized. In contrast, conventional methods directly measure an increase in the amplified products with increase in the qPCR cycle. Bound probes (molecular beacons or strand displacement probes) are fully fluorescent or get hydrolyzed (TaqMan Probe) by the polymerase. FIG. 1C is a schematic depicting single color PCR multiplexing strategies for detection of multiple analytes (e.g., five targets (Targets A, B, C, D, and E)) by measuring fluorescence at different melting temperatures of unbound (free) probes/quencher oligo complexes (P: Probe; Q: Quencher) Amplicons detected by probes having the same color are differentiated based on the melt difference between different probes which depends on the extent of complementarity between the quencher oligonucleotide and detection probe sequences. The detection probes each can either possess a chimeric sequence that is complementary to a different extent to a quencher oligonucleotide sequence or specific sequence that is complementary to different extent to specific quencher oligonucleotide sequences. This allows fluorescence of different probes at different temperatures and the fluorescence at different temperatures is used to determine the amplification profile for each target.

FIG. 6D depicts detection of an analyte using a molecular beacon that is self-hybridized and therefore quenched at temperatures below its melting temperature and when not bound to the target amplicon. In FIG. 6E, four different molecular beacons are shown which are unhybridized (fully extended) when bound to template or at a temperature above their respective melting temperatures. Unbound molecular beacon probes are unquenched at temperatures below their respective melting temperatures.

DETAILED DESCRIPTION OF THE INVENTION

Figure 1A:
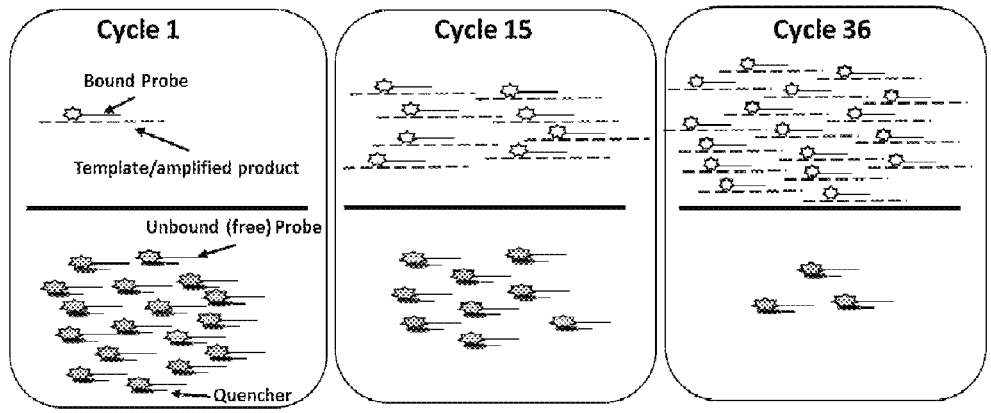
FIGS. 1A-1C are illustrations of disclosed qPCR detection principles. Labeled probe or primer specifically bound to amplified DNA is fully fluorescent. Unbound primer or probe is fully quenched and the quantity of unbound probe at each cycle is measured by a temperature protocol. The extent of complementarity between unbound probe and quencher oligo is designed to detect specific target of interest, and is used to achieve single color multiplexing. As the qPCR cycle progresses, the amount of free primers and probes decreases whereas the amount of amplified DNA product increases. The disclosed detection methodology measures the amount of unused or unutilized probes, which can be designed to detect single or multiple DNA or RNA targets of interest. Fluorescence data collected at each qPCR cycle is deconvoluted at the completion of qPCR run (i.e., post qPCR run data analysis). Unbound probe decreases with increasing qPCR cycle and can be transformed into an increasing product amplification curve.
Figure 1B:
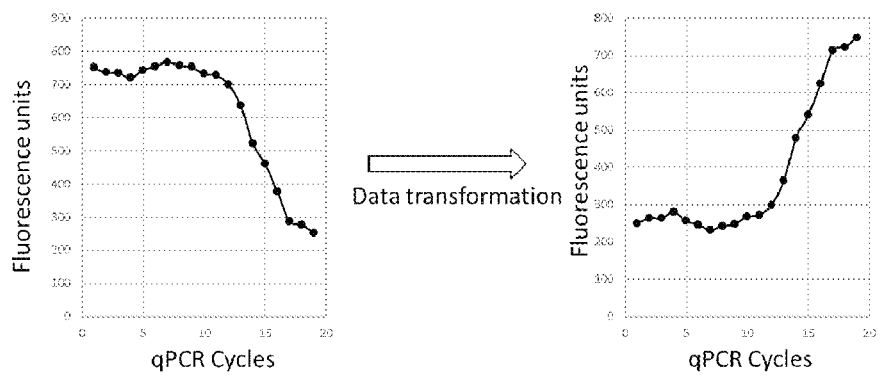
Figure 1C:
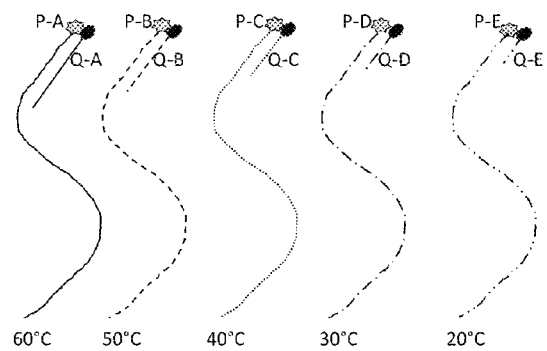

The disclosed methods and compositions can be understood more readily by reference to the following detailed description of particular embodiments and the Examples included therein and to the Figures and their previous and following description.

Quantitative assay of miRNAs has faced great difficulties and challenges for reasons including: (1) mature miRNAs are very small RNAs without poly(A) tail; (2) many miRNAs are highly conserved in sequence (in some cases there is only one-nucleotide difference); and (3) miRNAs generally express at relatively low levels. Nevertheless, several methods have been developed for assaying miRNAs, including hybridization-based and polymerase chain reaction (PCR) based-methods. However, current method face challenges such as requiring a relatively large amount of input RNA (e.g., Northern blot), having low specificity (e.g., microarray), being time-consuming and laborious in operation, and being unsuitable for high-throughput analysis.

Considering such limitations of current approaches, alternative approaches for multiplex detection and/or quantification of target DNA/RNA molecules have been developed.

In particular, an alternative and improved method for amplification (e.g., RT-qPCR) based detection of nucleic acids such DNA and RNA including, but not limited to, miRNAs has been developed. Furthermore, improved methods of detecting miRNAs, which can be used separately or in combination with the methods of detecting nucleic acids, are also provided.

In some embodiments, the disclosed methods facilitate reverse transcription (RT), multiplex qPCR or an alternative amplification strategy such as dPCR or isothermal amplification, and/or normalization approaches for detection of miRNA (e.g., from serum, plasma or other body fluids). The method uses a tagged RT primer and well understood DNA polymerase-based processes to incorporate tags that serve as primer binding sites during amplification (e.g., qPCR) step, and color multiplexing detection using strand displacement probes (double-stranded probes), optionally, but preferably employing a detection strategy that includes measuring unutilized fluorescent probes at each amplification (e.g., qPCR) cycle, The probes are easy to synthesize in a larger scale and are cost-effective (e.g., not requiring an enzyme with 5'-3' exonuclease activity) (Morrison L E, et al., Anal Biochem. 183(2):231-44 (1989); Ellwood M S, et al., Clin Chem., 32(9):1631-6 (1986); Li Q, et al., Nucleic Acids Res., 30(2):E5 (2002)). A common quencher (e.g., all probes in the assay can be quenched by the same quencher oligo) or distinct quenchers may be used.

More particularly, in some embodiments, the methods of detect miRNAs include reverse transcription of a miRNA using a specific RT primer with a universal tag sequence that contains blocker and reverse primer binding sites. The blocker allows for the RT primer to preferentially bind to mature miRNA (as compared to pri- or pre-miRNA). After the RT, a tagged First PCR ($1^{st}$ PCR) primer binds to reverse transcribed miRNA and extends it to create a template for amplification (e.g., qPCR). The tagged sequences in the RT and $1^{st}$ PCR primers are incorporated in amplifying cycles leading to multiple template copies for each miRNA that is reverse transcribed. The process also incorporates the tag sequences containing primer binding sites for amplification (e.g., qPCR). All miRNAs (e.g., miRNA of interest, endogenous control miRNA, and exogenous control miRNA) can be amplified by universal primer pairs that bind to the tag sequences, thus minimizing quantification bias associated with differences in PCR efficiency caused by use of different primers. A detection probe can be used bind to a miRNA-specific region and adjoining tag sequence, thus facilitating a highly specific detection assay. Any unbound detection probe can be quenched by a common or unique quencher.

Embodiments of the disclosed compositions and methods may have one or more of several differences and advantages over methods currently used in the art, including: i) incorporation of tag sequences in the detection probes and quencher oligonucleotide binding to the tag sequences; ii) measurement of the amount of fluorescence from unbound/unused/unutilized detection probes (especially in multiplexing); iii) multiplexing using unbound/unused probes at different melting temperatures and deconvolution of the fluorescence data; and/or iv) use of a common quencher oligonucleotide, in some embodiments.

It is to be understood that the disclosed method and compositions are not limited to specific synthetic methods, specific analytical techniques, or to particular reagents unless otherwise specified, and, as such, can vary. It is also to be understood that the terminology used herein is for the purpose of describing particular embodiments only and is not intended to be limiting.

I. Definitions

The term "conditions sufficient for" refers to any environment that permits the desired activity, for example, that permits specific binding or hybridization between two nucleic acid molecules or that permits reverse transcription and/or amplification of a nucleic acid. Such an environment may include, but is not limited to, particular incubation conditions (such as time and/or temperature) or presence and/or concentration of particular factors, for example in a solution (such as buffer(s), salt(s), metal ion(s), detergent(s), nucleotide(s), enzyme(s), etc.).

As used herein, the terms "nucleic acid", "polynucleotide" and "oligonucleotide" refer to primers, probes, oligomer fragments, and oligomer controls and are generic to polydeoxyribonucleotides (containing 2-deoxy-D-ribose), to polyribonucleotides (containing D-ribose), and to any other type of polynucleotide which is an N glycoside of a purine or pyrimidine base, or modified purine or pyrimidine bases. There is no intended distinction in length between the term "nucleic acid", "polynucleotide" and "oligonucleotide", and these terms will be used interchangeably. These terms refer only to the primary structure of the molecule. Thus, these terms include double- and single-stranded DNA, as well as double- and single stranded RNA.

The "melting temperature," or "T m" measures stability of a nucleic acid duplex. The Tm of a particular nucleic acid duplex under specified conditions is the temperature at which half of the duplexes have disassociated.

The "annealing temperature," or "$T_a$" is the temperature used in the annealing step of a PCR reaction. A formula that can be used for calculating $T_a$ is $$T_a = 0.3 \times T_m(\text{primer or probe}) + 0.7 T_m(\text{product}) - 14.9$$

where, $T_m$(primer or probe)=Melting temperature of the primers or probe $T_m$(product)=Melting temperature of the product Traditionally, with reference to primer design, too high $T_a$ can lead to insufficient primer- or probe-template hybridization. Too low $T_a$ may possibly lead to non-specific products, caused by a high number of base pair mismatches. Mismatch tolerance is found to have the strongest influence on PCR specificity.

Thus, in traditional primer design, generally, it is routine to use an annealing temperature ($T_a$) of 10 to 15° C. lower than the $T_m$. In preferred embodiments, the annealing temperature is within +/−5 degrees of $T_m$.

As used herein, the terms "detect" or "detecting generally refer to obtaining information. Detecting or determining can utilize any of a variety of techniques available to those skilled in the art, including for example specific techniques explicitly referred to herein. Detecting may involve manipulation of a physical sample, consideration and/or manipulation of data or information, for example utilizing a computer or other processing unit adapted to perform a relevant analysis, and/or receiving relevant information and/or materials from a source. Detecting may also mean comparing an obtained value to a known value, such as a known test value, a known control value, or a threshold value. Detecting may also mean forming a conclusion based on the difference between the obtained value and the known value.

The terms "contact", "contacting" or "bringing into contact" describe placement in physical association for example, in solid and/or liquid form. For example, contacting or combining can occur in vitro with one or more primers and/or probes and a biological sample (such as a sample including nucleic acids) in solution.

"Amplification" or "amplifying" refers to increasing the number of copies of a nucleic acid molecule, such as a gene, fragment of a gene, or other genomic region. The products of an amplification reaction are called amplification products or amplicons.

As used herein, the term "primer" refers to an oligonucleotide, which is capable of acting as a point of initiation of nucleic acid synthesis when placed under conditions in which synthesis of a primer extension product which is complementary to a target nucleic acid strand is induced, e.g., in the presence of different nucleotide triphosphates and a polymerase in an appropriate buffer ("buffer" includes pH, ionic strength, cofactors etc.) and at a suitable temperature. In some embodiments, the primer is preferably single-stranded. One or more of the nucleotides of the primer can be modified for instance by addition of a methyl group, a biotin or digoxigenin moiety, a fluorescent tag or by using radioactive nucleotides. A primer sequence need not reflect the exact sequence of the template. For example, a non-complementary nucleotide fragment may be attached to the 5' end of the primer, with the remainder of the primer sequence being substantially complementary to the template. Primer includes all forms of primers that may be synthesized including peptide nucleic acid primers, locked nucleic acid primers, phosphorothioate modified primers, labeled primers, and the like. The term "forward primer" as used herein means a primer that anneals to the anti-sense strand of a double-stranded DNA (dsDNA) fragment. A "reverse primer" anneals to the sense-strand of a dsDNA fragment.

The terms "complement", "complementary" or "complementarity" as used herein with reference to polynucleotides (i.e., a sequence of nucleotides such as an oligonucleotide or a target nucleic acid) refer to the Watson/Crick base-pairing rules. The complement of a nucleic acid sequence as used herein refers to an oligonucleotide which, when aligned with the nucleic acid sequence such that the 5' end of one sequence is paired with the 3' end of the other, is in "antiparallel association." For example, the sequence "5'-A-G-T-3'" is complementary to the sequence "3'-T-C-A-5'." Certain bases not commonly found in naturally occurring nucleic acids may be included in the nucleic acids described herein. These include, for example, inosine, 7-deazaguanine, Locked Nucleic Acids (LNA), and Peptide Nucleic Acids (PNA). Complementarity need not be perfect (e.g., it can be partial or complete); stable duplexes may contain mismatched base pairs, degenerative, or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs. A complement sequence can also be an RNA sequence complementary to the DNA sequence or its complement sequence, and can also be a cDNA.

The terms "target nucleic acid" or "target sequence" or "target segment" as used herein refer to a nucleic acid sequence of interest to be detected and/or quantified in the sample to be analyzed. Target nucleic acid may be composed of segments of a genome, a complete gene with or without intergenic sequence, segments or portions of a gene with or without intergenic sequence, or sequence of nucleic acids to which probes or primers are designed to hybridize. Target nucleic acids may include a wild-type sequence(s), a mutation, deletion, insertion or duplication, tandem repeat elements, a gene of interest, a region of a gene of interest or any upstream or downstream region thereof. Target nucleic acids may represent alternative sequences or alleles of a particular gene. Target nucleic acids may be derived from genomic DNA, cDNA, or RNA.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other forms the values may range in value either above or below the stated value in a range of approx. +/−5%; in other forms the values may range in value either above or below the stated value in a range of approx. +/−2%; in other forms the values may range in value either above or below the stated value in a range of approx. +/−1%. The preceding ranges are intended to be made clear by context, and no further limitation is implied.

II. Compositions

Reagents and compositions for detection and/or quantification of targets, such as polynucleotides are disclosed. The compositions can be useful for methods involving reverse transcription and PCR (e.g., qPCR).

A. Samples

The disclosed methods allow for quantitative detection of one or more target polynucleotides (e.g., miRNA) in a sample. The sample can include, without limitation, DNA, RNA, cDNA, dsDNA, ssDNA, high Molecular Weight (MW) DNA, chromosomal DNA, genomic DNA, mitochondrial DNA (mtDNA), and mRNA. In preferred embodiments, the target polynucleotide is selected from genomic DNA, mRNA, and miRNA.

In some embodiments, the sample can include RNA, such as total RNA or size selected RNA (e.g., small RNA). For example, the sample can be enriched for miRNAs. In some embodiments, the sample includes RNA selected from small nucleolar RNA, messenger RNA (mRNA), tRNA, small interfering RNA (siRNA), microRNA, and antisense RNA.

In preferred embodiments, the sample includes one or more miRNAs. In some embodiments, the miRNAs can be associated with a disease or disorder such as cancer, cardiovascular diseases, liver diseases, sepsis, infectious diseases (or causative agents thereof), genetic disorders, metabolic disorders, and neurodegenerative diseases.

Exemplary miRNAs include miR-122, miR-192, miR-21, miR-223, miR-375, miR-30a, miR-33a, miR-34a, miR-16, miR-155, miR-132, miR-27a, miR-150, miR-199, miR-200, miR-17, miR-214, miR-9, miR-29a, miR-212, miR-214, miR-497, miR-378, miR-320, miR-222, miR-106a, miR-92, miR-20, miR-23, miR-18, miR-126, and Cel-miR-39.

The sample can be isolated or derived from any suitable sample from the subject. Thus, in some embodiments, the methods can involve obtaining a nucleic acid sample from a subject. Exemplary samples include blood (such as peripheral blood), plasma, serum, urine, saliva, mucosal excretions, sputum, stool, spinal fluid, amniotic fluid, lymph fluid, vitreous, urine, tears, perspiration, semen and the like. Isolation and extraction of the nucleic acids may be performed through collection of cells, tissues or bodily fluids using a variety of techniques. In some embodiments, collection may involve aspiration of a bodily fluid from a subject using a syringe. In other embodiments, collection may involve pipetting or direct collection of fluid into a collecting vessel.

In some embodiments, the sample contains nucleic acids (e.g., RNA) isolated or derived from exosomes or other extracellular vehicle. Extracellular vesicles (EVs) are a heterogeneous collection of membrane-bound structures with complex cargoes including proteins, lipids, and nucleic acids. EV subtypes include ectosomes, microvesicles (MV), microparticles, exosomes, oncosomes, apoptotic bodies (AB), and tunneling nanotubes (TNT) (Yáñez-Mó, et al., *J Extracell Vesicles.* 4: 27066 (2015)).

The nucleic acid sample may be isolated and extracted using a variety of techniques known in the art. In some cases, cell free DNA/RNA may be isolated, extracted and prepared using commercially available kits such as Trizol®.

Generally, nucleic acids are extracted and isolated from samples through a partitioning step in which cell free DNAs, as found in solution, are separated from cells and other non-soluble components of the sample. Partitioning may include, but is not limited to, techniques such as centrifugation or filtration. In other cases, cells are not partitioned from cell free DNA first, but rather lysed. In this example, the genomic DNA of intact cells is partitioned through selective precipitation. DNA or other nucleic acids may remain soluble and may be separated from insoluble genomic DNA and extracted. Generally, after addition of buffers and other wash steps specific to different kits, DNA may be precipitated using isopropanol precipitation. Further clean up steps may be used such as silica-based columns to remove contaminants or salts. General steps may be optimized for specific applications. Isolation and purification of cell free DNA may be accomplished using any means, including, but not limited to, the use of commercial kits and protocols provided by companies such as Sigma Aldrich, Life Technologies, Promega, Affymetrix, IBI or the like. Kits and protocols may also be non-commercially available.

In some embodiments, particularly where cellular RNA is the desired nucleic acid for analysis, the RNA can be isolated from the cell lysate. In some embodiments, the genomic DNA is removed from the cell lysate, and the cell lysate, including total cellular RNA is utilized as the starting material for reverse transcription. In some embodiments, isolation of total RNA and removal of genomic DNA are combined.

Methods and kits for facilitating RNA isolation, and/or removal of genomic DNA are known in the art and can be used or modified as known in the field of nucleic acid amplification to facilitate preparation of RNA for reverse transcription. An exemplary kit is Rneasy® Plus Micro Kit (Qiagen). The process typically includes spinning cell or tissue lysates through spin columns to remove genomic DNA. Next, total RNA is purified using a second spin column. In some embodiments, an RNA carrier, such synthetic poly(A) RNA, can added to the lysis buffer before homogenizing the cells. Mild lysis buffer can include one or more detergents such as TRITON®-X100, IGEPAL CA-630, NP40, TWEEN® 20 at a concentration of about 0.01 to about 2%. See, e.g., U.S. Pat. No. 10,017,761.

B. Oligonucleotides

The compositions can contain one or more oligonucleotides including reverse transcription (RT) primers, blocker oligonucleotides, detection probes, quencher oligonucleotides, molecular beacons, first PCR primer, common forward primers, and common reverse primers.

Any disclosed oligonucleotide can be designed to have a desired melting temperature. Suitable programs for designing and predicting parameters such as Tm for oligonucleotides are known in the art and include Oligo Analyzer Tool (Integrated DNA Technologies) and various tools available at dna-utah.org.

RT Primer

Typically, the RT primer is a single-stranded oligonucleotide (e.g., containing DNA) that can act as a point of initiation for nucleic acid synthesis under suitable conditions. Typically, the RT primer is able to hybridize to a target RNA (e.g., miRNA, mRNA) to facilitate cDNA synthesis by a reverse transcriptase. Thus, in some embodiments, the melting point for the duplex formed by the RT primer and target RNA has to be suitable for a first strand synthesis using a reverse transcriptase.

In preferred embodiments, the RT primer includes in the 5' to 3' direction, (i) a tag collectively containing a universal reverse primer sequence and a binding site for the blocker oligonucleotide, and (ii) a sequence complementary to the 3'-end of the target RNA (e.g., miRNA). For example, an RT primer can include a 3' sequence (e.g., 4-8 bps) that is complementary to a mature miRNA of interest immediately followed by a 10-14 bp sequence that is complementary to a blocker oligonucleotide, and a 25-30 bps complementary to a universal reverse primer sequence used in amplification (e.g., qPCR).

In some embodiments, the RT primer does not include a binding site for the blocker oligonucleotide. Thus, for example, the RT primer can include a 3' sequence (e.g., 4-8 bps) that is complementary to a target RNA (e.g., mRNA) of interest and a sequence (e.g., 25-30 bps) complementary to a universal reverse primer sequence used in amplification (e.g., qPCR).

In some embodiments, the RT primer contains about 30-50 (e.g., about 30, 35, 40, 45, or 50) nucleotides, preferably about 45 nucleotides. In some embodiments, the sequence in the RT primer complementary to the 3'-end of the target RNA can include about 4-8 nucleotides.

Generally, the melting temperature ($T_m$) of the RT primer is designed to be between about 12-20° C. (e.g., when used to reverse transcribe miRNA).

Generally, the annealing temperature ($T_a$) of the RT primer is designed to be between about 14-18° C. (e.g., when used to reverse transcribe miRNA).

Blocker Oligonucleotide

In some embodiments, a blocker oligonucleotide may be used to enhance preferential reverse transcription of mature miRNAs e.g., as compared to the pri-miRNA or pre-miRNA. It is contemplated that the blocker oligonucleotide allows transcription of only (or preferentially) mature miRNA. The blocker oligonucleotide can prevent precursor miRNA from being used as template during the reverse transcription process. Thus, the blocker oligonucleotide can enhance preferential reverse transcription of mature miRNA over precursor miRNA. The blocker oligonucleotide can compete/block the precursor microRNA by creating structural interference.

In some embodiments, the 3' end of the blocker oligonucleotide is blocked from being extendable by a polymerase. For example, the 3' end of the blocker oligonucleotide can be phosphorylated.

In some embodiments, the blocker oligonucleotide hybridizes to the RT primer at the blocker oligonucleotide binding site. In some embodiments, the blocker oligonucleotide hybridizes to the RT primer adjacent to the 3'-end of the target RNA (e.g., miRNA), when the target RNA (e.g., miRNA) is hybridized to the RT primer.

In some embodiments, the blocker oligonucleotide contains about 12-16 (e.g., 12, 13, 14, 15, 16) nucleotides.

Generally, the melting temperature ($T_m$) of the blocker is designed to be about 42 to 52° C. inclusive, e.g., 48-52° C.

Generally, the annealing temperature ($T_a$) of the blocker is designed to be between about 43-53° C., inclusive (e.g., 48+/−5 degrees).

First PCR Primer

In some embodiments, a first PCR (forward) primer is used in a pre-qPCR (or dPCR or isothermal) amplification step. The first PCR (and generally the pre-qPCR (or dPCR or isothermal) amplification step) can be used to incorporate one or more tags into the target nucleic acid. This can also facilitate enrichment of the tagged target nucleic acid for subsequent amplification (e.g., qPCR or dPCR or isothermal).

In some embodiments, the first PCR primer contains in the 5' to 3' direction, a tag collectively containing a universal forward primer sequence and a sequence complementary to an oligonucleotide quencher sequence, and a sequence corresponding to the 5'-end of the target miRNA. Preferably, the sequence corresponding to the 5'-end of the target miRNA can include about 1-12 nucleotides. In some embodiments, the first PCR primer contains about 10-16 nucleotides.

Generally, the melting temperature ($T_m$) of the first PCR primer is designed to be about 42-46° C., inclusive.

Generally, the annealing temperature ($T_a$) of the first PCR primer is designed to be about 37-51° C., inclusive.

Universal Forward and Reverse Primers

The compositions can also contain one or more primers. These primers (e.g., forward and reverse primers) can be used in amplifying nucleic acid molecules in accordance with the disclosed methods. In preferred embodiments, the forward and reverse primers can be universal or common primers (e.g., the same forward and reverse primers can be used for the amplification of two or more distinct targets). In other embodiments, the forward and reverse primers are target-specific.

In some embodiments, the universal forward primer contains the universal forward primer sequence of the first PCR primer. In some embodiments, the universal reverse primer contains the universal reverse primer sequence of the RT primer.

Primers are typically at least 10, 15, 18, 20, 25, 30, 40, 50, or 60 nucleotides in length. In some embodiments, primers are preferably between about 15 to about 30 nucleotides in length, and more preferably between about 20 to about 25 nucleotides in length (e.g., 20 or 24 nucleotides). However, there is no standard primer length for optimal hybridization or amplification. An optimal length for a particular primer application may be readily determined by those of skill in the art.

In some embodiments, the forward primer and reverse primers are designed to have a Tm of about 58-62° C., inclusive. Generally, the annealing temperature for PCR forward and reverse primers should be low enough to allow both forward and reverse primers to bind to the single-stranded DNA template, but not so low as to permit the formation of undesired, non-specific duplexes or intramolecular hairpins. Thus, in some embodiments, the annealing temperature is set a few degrees (e.g., 3-6, such as 5) lower than the lowest Tm of the forward and reverse primers.

Generally, the melting temperature ($T_m$) of the universal PCR primers is designed to be about 58-62° C., inclusive.

Generally, the annealing temperature ($T_a$) of the universal PCR primers is designed to be about 53-63° C., inclusive.

Detection Probes and Quencher Oligonucleotides

The disclosed amplification (e.g., qPCR or dPCR or isothermal) step(s) typically include detection of the amplification products(s). As discussed elsewhere herein, in some embodiments, detection employs use of standard qPCR detection technology such as DNA-binding dyes and fluorescently labeled sequence-specific primers or probes including, but not limited to, hybridization probes, hydrolysis probes, molecular beacons, scorpions, sunrise primers, LUX primers, etc. However, in some embodiments, particularly where a single fluorescent channel is used to detect multiple amplicons, the detection strategy may include detection probe(s) or molecular beacons designed to bind to different amplicons at different annealing and/or melting temperatures. For example, in some embodiments, detection includes use of linked or unlinked detection probes and quencher oligonucleotides. Linkage can be, e.g., via an internucleotide linkage such as a phosphodiester bond, phosphorothioate linkage, etc. Thus, in some embodiments, the detection probe and quencher oligonucleotide are part of the same continuous single oligonucleotide, while in other embodiments, they are two separate unlinked molecules. In some embodiments, detection includes use of a modified molecular beacon strategy, which is described in more detail below.

In preferred embodiments, real-time qPCR (or dPCR or isothermal) is performed using a detection probe and a quencher oligonucleotide. Detection probe refers to a labelled oligonucleotide which can be used to inform the presence of a specific target nucleic acid. Typically, a detection probe can form a duplex structure with a sequence within the amplified target nucleic acid, due to complementarity of the probe with a sequence in the target region. In preferred embodiments, the detection probe includes a fluorophore, a first region containing the tag sequence (or a portion thereof) of the first PCR primer, and a second region containing a (target-specific) sequence that is complementary to the amplified target nucleic acid product. In preferred embodiments, the detection probe includes a fluorophore, and a second region containing a (target-specific) sequence that is complementary to the amplified target nucleic acid product. In some embodiments, the first region includes about 7-12 nucleotides and/or the second region includes about 15-25 nucleotides.

Generally, the melting temperature ($T_m$) of the detection probes is designed to be about 70-78° C., inclusive.

Generally, the annealing temperature ($T_a$) of the detection probes is designed to be between about 65-83° C., inclusive.

In preferred embodiments, the detection probe can be designed to hybridize/anneal to the target at a higher temperature (e.g., 5-10° C. higher) than which the forward and/or reverse primers anneal, in order to ensure detection before primers are extended. If the detection probe binds to the target at the same time or after the forward/reverse primers bind, the polymerase may begin replication of target that does not contain bound detection probe. As a result, new DNA will be synthesized without detecting fluorescence from a previous round. Such a situation can lead to inaccurate data.

In some embodiments, the detection probe is designed to bind/hybridize to the target of interest at 70° C. or more. In some embodiments, the detection probe is designed such that any detection probe not bound to target will be quenched at 58-62° C., inclusive (e.g., due to binding to the quencher oligonucleotide).

The quencher oligonucleotide is an oligonucleotide that can hybridize with the detection probe. In preferred embodiments, the quencher oligonucleotide includes a fluorescence quencher and a sequence that is fully or partially complementary to the first region of the detection probe. In preferred embodiments, the quencher oligonucleotide includes a fluorescence quencher and a sequence that is fully complementary to the detection probe. Typically, the quencher oligonucleotide contains about 10-12 nucleotides and/or the detection probe contains about 30 nucleotides or more (e.g., 30, 31, 32, 33, 34, 35, 36, 37, 38, 39, 40 nucleotides or more).

Generally, the melting temperature ($T_m$) of the quencher is designed to be about 24-62° C., inclusive.

Generally, the annealing temperature ($T_a$) of the quencher is designed to be about 19-65° C., inclusive.

Typically, the quencher oligonucleotide and the detection probe are capable of hybridizing to each other, and the hybridization can result in quenching of fluorescence from the fluorophore by the fluorescence quencher. The detection probe/quencher oligonucleotide can have different structures under different conditions, and this can be reflected by the fluorescence change. When the detection probe and quencher oligonucleotide hybridize to each other in a stable double-stranded structure, the fluorophore and the quencher are in close proximity. The fluorophore can be quenched by the quencher and the detection probe becomes non-fluorescent at the emission wavelength of the fluorophore. When under denaturing conditions, such as under high temperature, the detection probe and quencher oligonucleotide are separated, and the fluorophore become fluorescent. In the presence of the target amplification product under suitable conditions, the detection probe can spontaneously bind to a strand of the amplification product, in lieu of the quencher oligonucleotide, and the fluorophore becomes fluorescent. In some embodiments, the detection probe forms a thermodynamically more stable duplex with the target amplification product as compared to the quencher oligonucleotide.

In some embodiments, the 3' end of the quencher oligonucleotide and/or the detection probe is blocked from being extendable by a polymerase. Suitable blockers include a phosphate group, quencher moiety, or biotin. In some embodiments, the 3' end of the quencher oligonucleotide is blocked from being extendable by a polymerase with a quencher moiety (e.g., Black Hole Quencher® (BHQ®)). In some embodiments, the 3' end of the detection probe is phosphorylated.

Both the fluorophore and the fluorescence quencher can be on the terminal or internal bases of the detection probe or quencher oligonucleotide. In preferred embodiments, they are on opposed terminal complementary bases of the two strands. Thus, in some embodiments, the fluorophore can be attached to the 5' or 3' end of the detection probe, and/or the fluorescence quencher can be attached to the 5' or 3' end of the quencher oligonucleotide. In some preferred embodiments, the fluorophore is attached to the 5' end of the detection probe. In some preferred embodiments, the fluorescence quencher is attached to the 3' end of the quencher oligonucleotide.

In some embodiments, the detection probe and quencher oligonucleotide are unlinked, and thus two separate oligonucleotides.

Molecular Beacons

Figure 4:
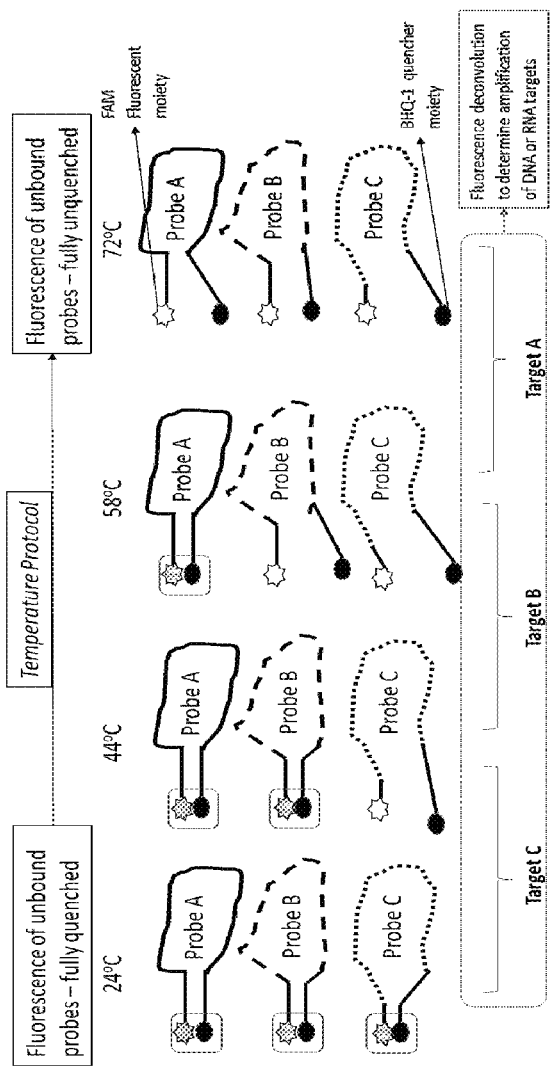
FIG. 4 is a schematic depiction of a single-color multiplex detection of three targets using three molecular beacons (e.g., linked detection probe quencher oligonucleotide pairs). After 95° C. denaturation, the reaction is cooled down to 24° C. During this step, fluorescent molecular beacons bind to respective targets and any molecular beacon not bound to target is quenched by formation of a hairpin loop. At 44° C., unbound molecular beacon C becomes unhybridized whereas unbound molecular beacons A and B are still quenched. At 58° C., unbound molecular beacon B and C are unhybridized, whereas unbound molecular beacon A is still quenched. At 72° C., hairpin loops of unbound molecular beacons A, B and C are all destabilized and thus, unhybridized. Amount of unbound molecular beacons probes designed to bind to different DNA or RNA targets in the same fluorescent color, is identified by the extent of self complementarity at 5' and 3' end of the probes. The difference in fluorescence intensity at these temperatures is used to differentiate targets amplified in the same color.
Figure 5A:
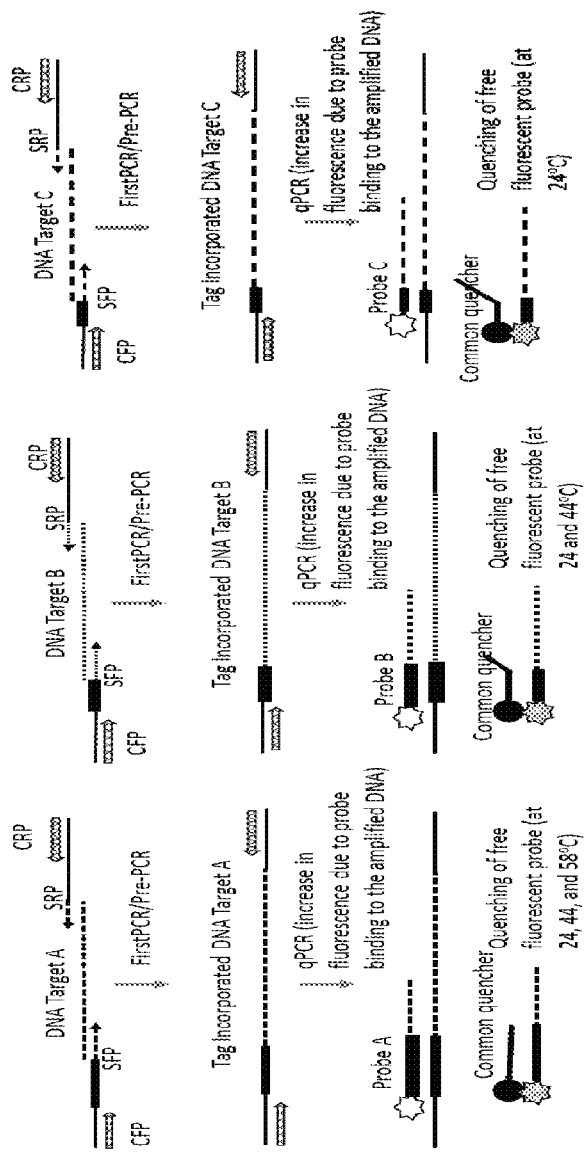
FIG. 5A is an exemplary schematic depiction of a single-color multiplex, common quencher oligo approach for amplification and detection of DNA Targets. Targets A, B, and C are pre-amplified with tag containing primers. The tag of Specific Forward Primer (SFP) has sequence complementary to the quencher oligonucleotide and Common Forward Primer (CFP) binding site whereas, the tag of Specific Reverse Primer (SRP) has Common Reverse Primer (CRP) binding site. Targets A, B, and C are pre-amplified (2-10 cycles) to incorporate the tags using SFP and SRP primers. After pre-amplification, all three targets (in one color) or 18 targets (in six colors) are amplified by Common Forward and Common Reverse Primers. Single color-based detection is performed as described herein, e.g., as illustrated in FIG. 2A.
Figure 5B:
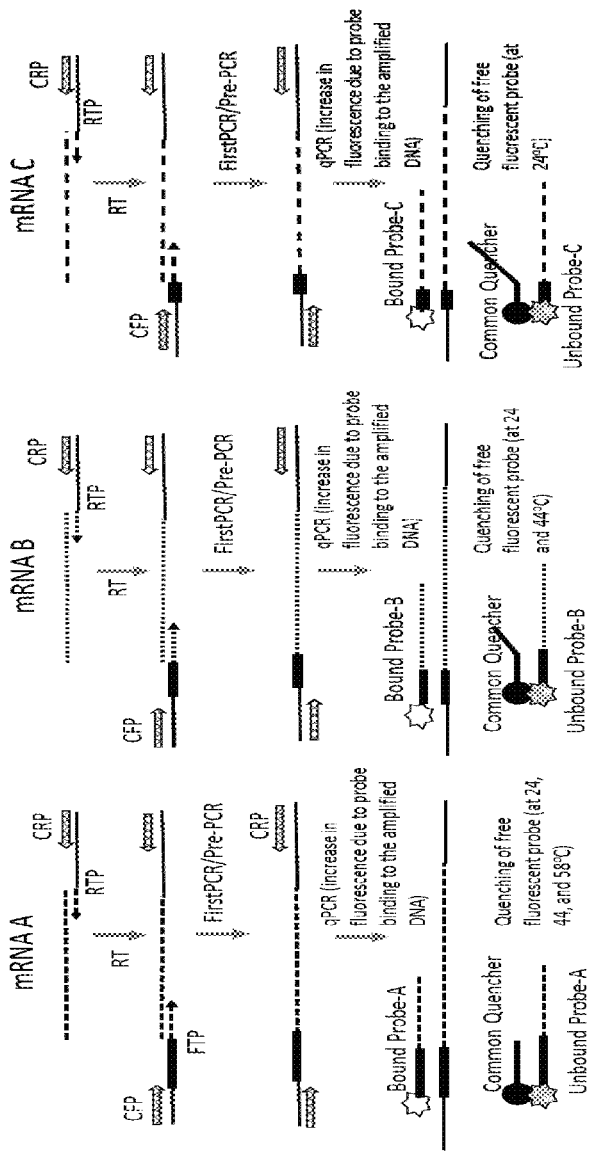
FIG. 5B is an exemplary schematic depiction of a single-color multiplex, common quencher oligo approach for amplification and detection of three mRNA targets. mRNA targets are reverse transcribed by mRNA specific reverse transcription primer (RTP) that contains the tag sequence to allow binding of Common Reverse Primer (CRP) during qPCR step. After reverse transcription step, the specific First Primer (FTP) is used to create double stranded DNA and amplify the template in the pre-PCR/First PCR reaction (2-10 cycles). The FTP has a tag sequence that allows binding of the Common Forward Primer and the detection probe. qPCR and detection is performed as described herein, e.g., as illustrated in in FIGS. 5A and 2A.
Figure 5C:
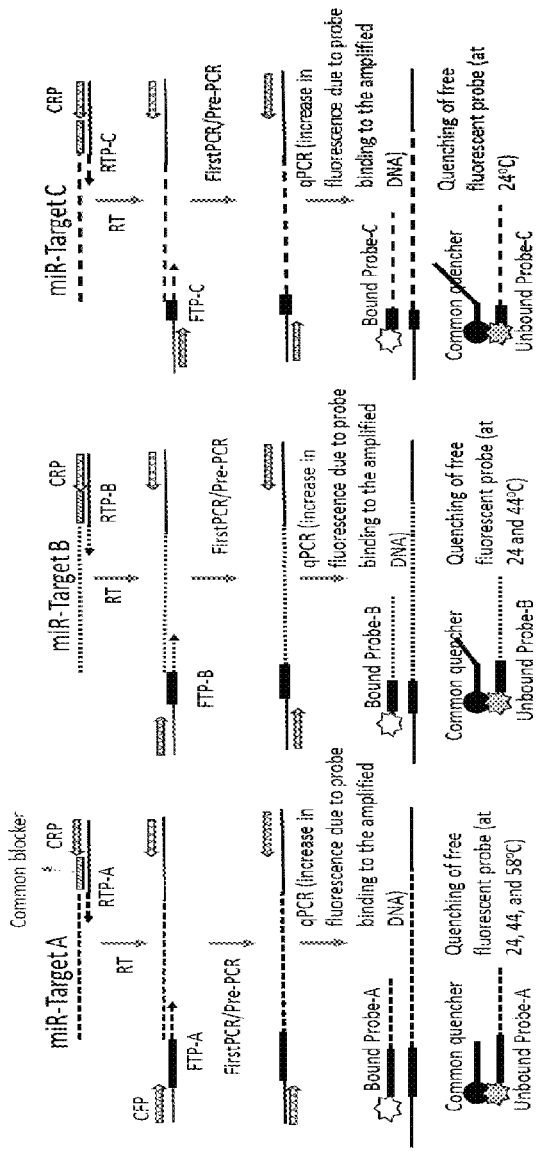
FIG. 5C is an exemplary schematic depiction of a single-color multiplex, common quencher oligo approach for amplification and detection of three miRNA targets. miRNA targets are reverse transcribed by mRNA specific reverse transcription primer (RTP) that contain tag sequence to allow binding of Common Reverse Primer (CRP) during qPCR step. RTP also contain sequence to bind a common blocker. Use of common blocker required to reverse transcribe mature miRNAs. After reverse transcription step, specific First Primer (FTP) is used to create double strand DNA and increase the template in qPCR by pre-PCR/FirstPCR reaction (2-10 PCR cycles). FTP has tag sequence that allow binding of Common Forward Primer and part of probe binding. After pre-amplification, all three targets (in one color) or 18 targets (in six colors) are amplified by Common Forward and Common Reverse Primers. The qPCR amplification and single color multiplexing can be performed as outlined herein, e.g., as illustrated in FIGS. 5A and 2A.
Figure 5D:
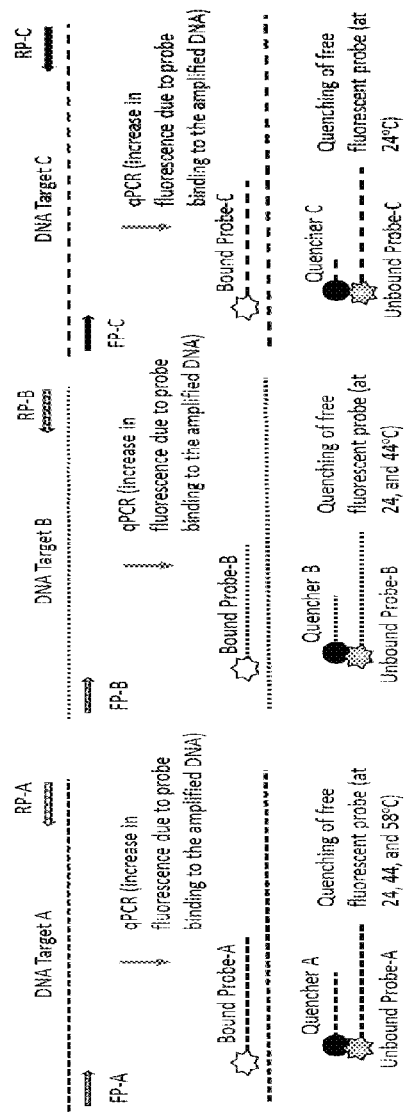
FIG. 5D is an exemplary schematic depiction of a single-color multiplex, specific quencher oligos approach for amplification and detection of DNA targets. Target A, B, and C are amplified using specific forward and reverse primers. Fluorescence of each specific unbound probe is quenched by specific quencher oligo that are pre-designed to dissociate at specific temperatures. Fluorescence data collection and deconvolution is used to generate amplification curve specific each target of interest. qPCR is performed as described herein, e.g., as illustrated in FIG. 5A and detection is performed as in FIG. 3A.
Figure 5E:
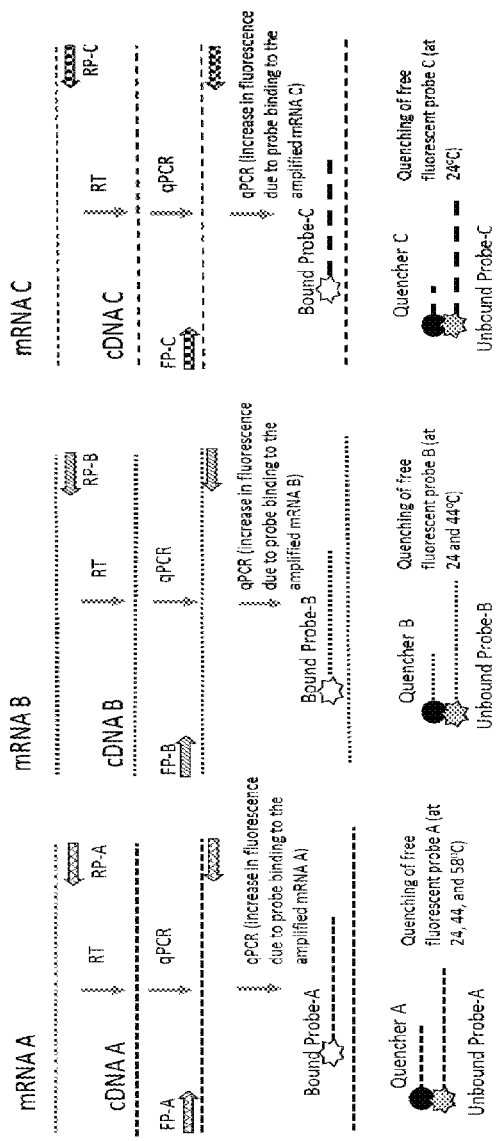
FIG. 5E is an exemplary schematic depiction of a single-color multiplex, specific quencher approach for amplification and detection of mRNA targets. mRNA targets are reverse transcribed by mRNA specific reverse primer (RP). After reverse transcription step, specific forward primer is used in qPCR. qPCR is performed as described herein, e.g., as illustrated in FIG. 5A and detection is performed as in FIG. 3A.
Figure 5F:
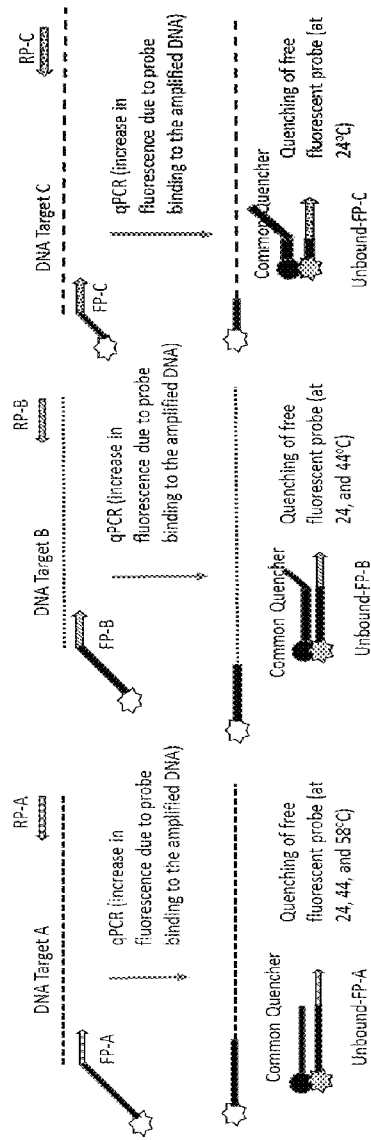
FIG. 5F is an exemplary schematic depiction of a single-color multiplex, primer (no probe), common quencher oligo approach for amplification and detection of mRNA targets. Target A, B, and C are amplified using specific forward and reverse primers. One of the primer, in this case Forward primer, is tagged and labelled with fluorescein (FAM™) dye (at 5' end). Fluorescence of each specific unbound primer is quenched by a common quencher oligo that are pre-designed to dissociate at specific temperatures. Fluorescence data collection and deconvolution are used to generate amplification curve specific for each target of interest.

In some embodiments, the detection probe and quencher oligonucleotide are linked, or form a single oligonucleotide, preferably one that can self-hybridize to form a hairpin, referred to as a molecular beacon (see, e.g., Tyagi S, Kramer F R., F1000 Med Rep., 4:10 (2012); Tyagi S. and Kramer F R., Nat Biotechnol., 14(3):303-8 (1996)). Thus, in some embodiments, real-time qPCR (or dPCR or isothermal) is performed using molecular beacons to detect one or more target polynucleotides. A molecular beacon is a single-stranded dual-labeled oligonucleotide that can form a hairpin or stem-loop conformation. The typical organization of a molecular beacon includes i) a loop portion, ii) a stem portion, and iii) a label (e.g., a fluorophore-quencher pair). Formation of the hairpin structure is facilitated by the stem sequences at both ends of the oligonucleotide which are complementary to each other and permit self-hybridization of the molecular beacon when it is not bound to its target. In some embodiments, when the molecular beacons are used in single color multiplexing, the length and/or composition of the stem sequences (which self-anneal) are varied to facilitate destabilization of the hairpin loops at different melting temperatures. See FIGS. 4A-4C which illustrate aspects of molecular beacon design and use thereof for detection of a target. Typically, the loop portion is a single-stranded sequence fully or partially complementary to the target polynucleotide.

In some embodiments, the molecular beacon includes about 36-50 nucleotides (in total). The loop portion is generally constructed by about 18-28 nucleotides, some or all of which can be specific to the target of interest. Typically, the stem portion includes about 7-12 base pairs. In some embodiments, a molecular beacon with a stem of about 7 bp melts at about 24° C. In some embodiments, a molecular beacon with a stem of about 12 bp melts at about 58° C.

In some preferred embodiments, the 5' and 3' ends of the molecular beacon contain a fluorophore and a quencher moiety, respectively. In some embodiments, the 5' and 3' ends of the molecular beacon contain a quencher moiety and a fluorophore, respectively. When the molecular beacon is self-hybridized to form a hairpin, the proximity of the fluorophore and quencher moiety causes the quenching of the fluorescence signal of the fluorophore. When molecular beacons hybridize to their specific target polynucleotide, this causes the hairpin structure to dissociate thus separating the fluorophore and quencher. As the quencher is no longer in proximity to the reporter, fluorescence emission takes place.

In some embodiments, the measured fluorescence signal is directly proportional to the amount of target polynucleotide. Preferably, the molecular beacons are not degraded during the amplification process, but rather remain intact and bind to the target polynucleotide in every cycle in order to produce measurable fluorescence.

In some embodiments, the molecular beacon is designed to bind/hybridize to the target of interest at 70° C. or more. In some embodiments, the molecular beacon is designed such that any molecular beacon not bound to target will be quenched at 24-58° C., inclusive.

Generally, the melting temperature ($T_m$) of the molecular beacon is designed to be about 76-84° C., inclusive.

Generally, the annealing temperature ($T_a$) of the molecular beacon is designed to be about 70-84° C., inclusive.

Fluorescently Labeled Primer-Probes

In some embodiments, a primer is also a probe. By fluorescently labeling one or more primers, the strategies disclosed herein of indirectly measuring amplification of the target by measuring unbound or unused probe can be carried out using primers only that also serve a probe, and without an additional probe. Thus, the compositions can also contain one or more fluorescently-labelled primers (e.g., forward and/or reverse primers). This/these primer(s) (e.g., forward or reverse primers) can be used in amplifying nucleic acid molecules in accordance with the disclosed methods. In preferred embodiments, the fluorescently labelled forward or reverse primers can be universal or common primers (e.g., the same forward and reverse primers can be used for the amplification of two or more distinct targets). In other embodiments, the forward and reverse primers are target-specific.

In some embodiments, fluorescently labelled forward or reverse primers contains the tag sequence at 5' end and target specific binding sequence at the 3' end.

Primers are typically at least 10, 15, 18, 20, 25, 30, 40, 50, or 60 nucleotides in length. In some embodiments, fluorescently-labeled primers are preferably between about 25 to about 45 nucleotides in length, and more preferably between about 30 to about 40 nucleotides in length (e.g., 31 or 39 nucleotides). However, there is no standard primer length for optimal hybridization or amplification. An optimal length for a particular primer application may be readily determined by those of skill in the art.

In some embodiments, the fluorescently-labelled forward primer or reverse primers are designed to have a Tm of about 66-74° C., inclusive.

In some embodiments, the fluorescently-labelled forward primer can be used to prime the qPCR (or dPCR or isothermal) reaction as well as used to measure amount of unused primer at each qPCR (or dPCR or isothermal) cycle.

Modifications to Oligonucleotides

The disclosed oligonucleotides can be modified at the base moiety, sugar moiety, or phosphate backbone, and may include other appending groups or labels, so long as the intended function is not compromised.

For example, the oligonucleotides may include one or more modified base moieties such as 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, and 2-methylguanine.

Suitable modified sugar moieties include arabinose, 2-fluoroarabinose, xylulose, and hexose. Suitable phosphate backbone modifications include phosphorothioate, phosphorodithioate, phosphoramidothioate, phosphoramidate, phosphordiamidate, methylphosphonate, alkyl phosphotriester, and a formacetal or analog thereof.

C. Fluorophores and Quenchers

In some embodiments, the disclosed oligonucleotides and methods related thereto utilize the principle of molecular energy transfer (MET) and, preferably, fluorescence resonance energy transfer (FRET). In some embodiments, the disclosed oligonucleotides and methods related thereto utilize the principle of static or contact quenching, molecular energy transfer, and FRET. When an acceptor fluorophore is brought closer to a donor fluorophore (e.g., 20-100 Å), the intensity of fluorescence of the acceptor fluorophore increases, whereas the intensity of the fluorescence of donor fluorophore decreases due to an increased efficiency of fluorescence resonance energy transfer (FRET) from donor to acceptor fluorophore. When these two moieties are brought even closer, the intensity of both donor and acceptor fluorophores is reduced, which is called static or contact quenching. At these intimate distances, most of the absorbed energy is dissipated as heat and only a small amount of energy is emitted as light. For example, adjacent probes and TaqMan probes use the FRET mechanism, wherein the distance between donor and acceptor moieties causes FRET quenching. On the other hand, in competitive hybridization probes and molecular beacons, when the probe is not hybridized to the target, the two fluorescent moieties are very close to each other causing contact or static quenching (see, e.g., Marras S A, et al., Nucleic Acids Res., 30(21):e122 (2002)). One of the useful features of contact quenching is that all fluorophores are quenched equally well, irrespective of whether the emission spectrum of the fluorophore overlaps the absorption spectrum of the quencher, one of the key conditions that determines the efficiency of FRET.

In some preferred embodiments, the methods rely on contact quenching since the detection probes and corresponding quencher oligonucleotides are designed to hybridize to each other, such that the fluorophore and fluorescence quencher are in close proximity.

The oligonucleotides can be labeled with a donor and/or an acceptor moiety. In some embodiments, the acceptor moiety may simply quench the emission of the donor moiety, or it may itself emit energy upon excitation by emission from the donor moiety. In a preferred embodiment, the donor moiety is a fluorophore, and the acceptor moiety may or may not be a fluorophore, such that fluorescent energy emitted by the donor moiety is absorbed by the acceptor moiety. In a preferred embodiment, the acceptor moiety is a fluorescence quencher.

A fluorescence quencher can quench a signal from the fluorophore to various degrees. For example, in some embodiments, the fluorescence signal detected in the presence of the fluorescence quencher can be 90% or less, 80% or less, 70% or less, 60% or less, 50% or less, 40% or less, 30% or less, 20% or less, 15% or less, 10% or less, or 5% or less of the signal detected in the absence of the fluorescence moiety. In some embodiments, no signal (e.g., above background) is detected in the presence of the fluorescence quencher.

In some embodiments, a suitable fluorophore is selected from: an Alexa Fluor® dye, an ATTO™ dye (e.g., ATTO™ 390, ATTO™ 425, ATTO™ 465, ATTO™ 488, ATTO™ 495, ATTO™ 514, ATTO™ 520, ATTO™ 532, ATTO™ Rho6G, ATTO™ 542, ATTO™ 550, ATTO™ 565, ATTO™ Rho3B, ATTO™ Rho11, ATTO™ Rho12, ATTO™ Thio12, ATTO™ Rho101, ATTO™ 590, ATTO 594, ATTO™ Rho13, ATTO™ 610, ATTO™ 620, ATTO™ Rho14, ATTO™ 633, ATTO™ 647, ATTO™ 647N, ATTO™ 655, ATTO™ Oxa12, ATTO™ 665, ATTO™ 680, ATTO™ 700, ATTO™ 725, ATTO™ 740), a DyLight® dye, a cyanine dye (e.g., Cy™2 Cy3™ Cy™3.5, Cy™3b, Cy5™ Cy™5.5, Cy™7, Cy™7.5), a FluoProbes dye, a Sulfo Cy™ dye, a Seta™ dye, an IRIS™ Dye, a SeTau™ dye, an Srfluor dye, a Square dye, fluorescein (FITC), tetramethylrhodamine (TRITC). Examples of Alexa Fluor® dyes include, but are not limited to: Alexa Fluor® 350, Alexa Fluor® 405, Alexa Fluor® 430, Alexa Fluor® 488, Alexa Fluor® 500, Alexa Fluor® 514, Alexa Fluor® 532, Alexa Fluor® 546, Alexa Fluor® 555, Alexa Fluor® 568, Alexa Fluor® 594, Alexa Fluor® 610, Alexa Fluor® 633, Alexa Fluor® 635, Alexa Fluor® 647, Alexa Fluor® 660, Alexa Fluor® 680, Alexa Fluor® 700, Alexa Fluor® 750, Alexa Fluor® 790, and the like.

In preferred embodiments, the fluorophore is selected from fluorescein (FAM™), hexachloro-fluorescein (HEX™), 2-chloro-7'-phenyl-1,4-dichloro-6-carboxy-fluorescein (VIC®), 5'-Dichloro-Dimethoxy-Fluorescein (JOE™), tetrachlorofluorescein (TET™), SUN™ tetramethylrhodamine (TAMRA™), QUASAR0670, CAL Fluor® Orange (CF560), CAL Fluor® Red 610 (CF610), and Texas Red® (Sulforhodamine 101 acid chloride).

Examples of fluorescence quenchers include, but are not limited to: a dark quencher, a Black Hole Quencher® (BHQ®) (e.g., BHQ®-0, BHQ®-1, BHQ®-2, BHQ®-3), a Qx1 quencher, an ATTO™ quencher (e.g., ATTO™ 540Q, ATTO™ 580Q, and ATTO™ 612Q), dimethylaminoazobenzenesulfonic acid (Dabsyl), Iowa Black® RQ, Iowa Black® FQ, IRDye® QC-1, a QSY® dye (e.g., QSY® 7, QSY® 9, QSY® 21), AbsoluteQuencher™, and Eclipse™. In some embodiments, a fluorescence quencher is a dark quencher. A dark quencher can absorb excitation energy and dissipate the energy in a different way (e.g., as heat). Thus, a dark quencher has minimal to no fluorescence of its own (does not emit fluorescence). Examples of dark quenchers are further described in U.S. Pat. Nos. 8,822,673 and 8,586,718; U.S. patent publications 20140378330, 20140349295, and 20140194611; and international patent applications: WO200142505 and WO200186001, all if which are hereby incorporated by reference in their entirety.

Other suitable fluorescence quenchers are known in the art and include, without limitation, 1,4-bis-(3-hydroxy-propylamino)-anthraquinone, 1-(3-(4,4'-dimethoxy-trityloxy) propylamino)-4-(3-hydroxypropylamino)-anthraquinone, 1-(3-(2-cyanoethoxy(diisopropylamino)phosphinoxy)propylamino)-4-(3-(4,4'-dimethoxy-trityloxy)propylamino)-anthraquinone (#Q1), 1,5-bis-(3-hydroxy-propylamino)-anthraquinone, 1-(3-hydroxypropylamino)-5-(3-(4,4'-dimethoxy-trityloxy)propylamino)-anthraquinone, 1-(3-(cyanoethoxy(diisopropylamino)phosphinoxy) propylamino)-5-(3-(4,4'-dimethoxy-trityloxy) propylamino)-anthraquinone (#Q2), 1,4-bis-(4-(2-hydroxyethyl)phenylamino)-anthraquinone, 1-(4-(2-(4,4'-dimethoxy-trityloxy)ethyl)phenylamino)-4-(4-(2-hydroethyl)phenylamino)-anthraquinone, 1-(4-(2-(2-cyanoethoxy(diisopropylamino)phosphinoxy)ethyl) phenylamino)-4-(4-(2-(4,4'-dimethoxy-trityloxy)ethyl) phenylamino)-anthraquinone, 1,8-bis-(3-hydroxy-propylamino)-anthraquinon, and 4-((4-(dimethylamino) phenyl)azo)benzoic Acid (Dabcyl).

In some embodiments, it can be advantageous to use different quenchers attached to the same quencher oligonucleotide (e.g., for the detection of two or more targets in multicolor multiplexing). For example, BHQ®-1, BHQ®-2, and BHQ®-3 can quench different fluorophores. For example, FAM™ can be quenched by BHQ®-1 whereas Quasar670 can be quenched by either BHQ®-2 or BHQ®-3.

In preferred embodiments, the fluorophore quencher is selected from BHQ®-1, BHQ®-2, and BHQ®-3.

D. Enzymes and Buffers

The compositions preferably include buffers and/or enzymes for performing the disclosed methods.

Typically, the buffers provide appropriate pH and ionic conditions for the one or more enzymes. For example, a buffer can be an aqueous solution that provides optimal pH, ionic strength, cofactors, and the like for optimal enzyme activity. In some embodiments, the buffers are suitable for storage of the enzymes. In preferred embodiments, the buffers are suitable for RT and PCR.

Suitable buffer components include, without limitation, one or more salts, reducing agents (e.g., Dithiothreitol), buffering agents, deoxynucleoside triphosphates (dNTPs), or combinations thereof. The one or more salts provide monovalent or divalent cations, such as, Mg2+, Mn2+, K+, NH4+, and Na+. Exemplary salts that can be included in the buffers are KCl, $MgCl_2$, NaCl, $MnCl_2$, $NH_4Cl$, MgSO4, $(NH_4)_2SO_4$, and magnesium acetate. The concentration of the one or more salts can be in the range of from about 1 mM to about 500 mM, about 5 mM to about 250 mM, about 10 mM to about 200 mM, about 25 mM to about 150 mM, or about 50 mM to about 100 mM.

Suitable buffering agents are known in the art and include, without limitation, tris (e.g., Tris-HCl), tricine, bicine, and HEPES. The buffering agent can have a pH in the range of about 6 to 10 (e.g., a pH of 6.8 to 9, such as about pH 8.5). The concentration of the one or buffering agents can be in the range of from about 10 mM to about 100 mM.

The compositions can further include one or more nucleotides (e.g., deoxynucleoside triphosphates (dNTPs)). The nucleotide components of the compositions serve as the "building blocks" for newly synthesized nucleic acids, being incorporated therein by the action of the reverse transcriptases or DNA polymerases. Examples of nucleotides suitable for use in the compositions include, but are not limited to, dUTP, dATP, dTTP, dCTP, dGTP, dITP, 7-deaza-dGTP, α-thio-dATP, α-thio-dTTP, α-thio-dGTP, α-thio-dCTP or derivatives thereof, all of which are available commercially from sources including Life Technologies, Inc. (Rockville, Md.), New England BioLabs (Beverly, Mass.) and Sigma Chemical Company (Saint Louis, Mo.). In preferred embodiments, the following dNTPs are included in the compositions: dATP, dTTP, dGTP, and dCTP.

Suitable reverse transcriptases are known in the art and are commercially available. In some embodiments, the reverse transcriptase is a Moloney Murine Leukemia Virus Reverse Transcriptase (MMLV-RT). Suitable commercial reverse transcriptases include MMLV High Performance Reverse Transcriptase and EpiScript™ Rnase H-Reverse Transcriptase (Lucigen), NEB ProtoScript II reverse transcriptase (NEB Cat. No M0368) and Invitrogen SuperScript II, III, and IV reverse transcriptase (Thermo Fisher Scientific Cat. No 18090010).

Suitable DNA polymerases are known in the art and are commercially available. In some embodiments, the DNA polymerase is a *Thermus aquaticus* DNA polymerase (Taq Pol). Suitable commercially available DNA polymerases include EconoTaq Polymerase, Phi29 DNA polymerase, Bsu DNA polymerase, OmniAmp™ DNA polymerase (Lucigen), Bst DNA polymerase, Bst 2.0 DNA polymerase, and Bst 2.0 WarmStart™ DNA polymerase (New England Biolabs), Platinum II Taq Polymerase (ThermoFisher Scientific), and KlenTaq1 from DNA Polymerase Technologies, Inc.

III. Methods of Use

Methods for detection and/or quantification of target polynucleotides, such as DNA and RNA molecules are disclosed. The methods are especially advantageous for multiplex detection of a plurality of targets (e.g., 2, 3, 4, 5, 6 or more) simultaneously (e.g., in the same reaction). The methods can be used in qualitative and/or quantitative detection of targets/analytes in applications such as infectious disease testing (e.g., pathogen detection and quantification), cancer detection (e.g., detection of SNPs, gene expression, copy number variation, gene fusions), and genetic testing. The compositions and methods provide improved assays for amplification based target detection and/or quantification. Although discussed primarily with respect to qPCR, the compositions and methods are also suitable to use with other forms of amplification such as digital PCR, isothermal amplification, etc. Thus, in each instance where the compositions and methods are discussed with respect PCR generally or qPCR specifically, nucleic acid amplification generally and digital PCR and isothermal amplification specifically are also expressly discussed in substitution thereof.

For example, the compositions and methods can improve the capacity of digital PCR (dPCR) that use fluorescence-based detection system. In dPCR, the PCR is of RNA or DNA is carried out in numerous small volume compartments. Each compartment can contain zero to one RNA or DNA molecules (Mao, et al., "Principles of digital PCR and its applications in current obstetrical and gynecological diseases," *Am J Transl Res.* 2019 Dec. 15; 11(12):7209-7222. PMID: 31934273; PMCID: PMC6943456, Whale, et al., "Fundamentals of multiplexing with digital PCR," *Biomol Detect Quantif.* 2016 May 27; 10:15-23. Doi: 10.1016/j.bdq.2016.05.002. PMID: 27990345; PMCID: PMC5154634). At the end of amplification reaction, the fluorescence from each compartment is counted and absolute copies are calculated based on the Poisson statistics and PCR-positive reactions. Like qPCR systems, dPCR systems are also limited by the number of fluorescent channels, requires primers for amplification of DNA or RNA and a fluorescent probe for detection.

The compositions and methods can also be used to improve the capacity of isothermal amplification systems that use fluorescence-based detection system. Unlike PCR, the isothermal amplification system does not require thermal cycling and amplification is carried out at an optimal temperature by a strand displacement DNA polymerase (Zhao, et al., *Isothermal Amplification of Nucleic Acids.* Chem Rev. 2015 Nov. 25; 115(22):12491-545. Doi: 10.1021/acs.chemrev.5b00428. Epub 2015 Nov. 9. PMID: 26551336, Obande, et al., "Current and Future Perspectives on Isothermal Nucleic Acid Amplification Technologies for Diagnosing Infections," *Infect Drug Resist.* 2020 Feb. 12; 13:455-483. Doi: 10.2147/IDR.S217571. PMID: 32104017; PMCID: PMC7024801.). Like PCR, isothermal amplification requires primers for amplification DNA or RNA of interest and fluorescent probe for detection.

Typically, the methods involve the amplification and detection of the target nucleic acid via qPCR using fluorescence-based detection. In some embodiments, the method involves detection of targets nucleic acid via digital PCR or isothermal amplification. In some embodiments, when the target nucleic acid is RNA, the methods can also involve reverse transcription of the target.

Reverse Transcription

For example, disclosed is a method for quantitative detection of target nucleic acids (e.g., miRNA) that includes (a) contacting a sample containing RNA with an (RT) primer and optionally a blocker oligonucleotide under conditions suitable for the RT primer to hybridize to the target nucleic acid (e.g., miRNA) and (b) performing reverse transcription to obtain cDNA. Typically, the RT primer includes (i) a tag composed of a universal reverse primer sequence and a binding site for the blocker oligonucleotide and (ii) a sequence complementary to the 3'-end of the target nucleic acid (e.g., miRNA).

Conditions and parameters for performing reverse transcription are known in the art. In some embodiments, reverse transcription is performed by incubating the reaction at 50° C. for 1 min, 16° C. for 10 mins, 25° C. for 10 mins, 37° C. for 10 mins, and 85° C. for 5 mins.

Pre-qPCR (First PCR or $1^{st}$ PCR or Pre-Amplification)

In some embodiments, the cDNA generated by the RT reaction is subjected to a pre-qPCR (also referred to herein as a first PCT, $1^{st}$ PCT, or preamplification, and can be, e.g., dPCR or isothermal) amplification procedure using primers specific to the target. This step can allow for incorporation of universal tag sequences (that can serve as common primer binding sites for subsequent qPCR) into the target molecule and/or enrichment of the cDNA. Thus, in some embodiments, the method can further involve (c) amplifying the cDNA by PCR using a first PCR primer to generate double-stranded DNA template, wherein the first PCR primer contains a universal forward primer sequence, a tag, and a sequence corresponding to the 5'-end of the target miRNA. The RT primer can be used in combination with the first PCR primer in this pre-qPCR step. In some embodiments, this pre-qPCR amplification step involves about 1-10 PCR cycles (e.g., 1, 2, 3, 4, 5, 6, 7, 8, 9, 10 cycles). In a preferred embodiment, the pre-qPCR amplification step involves about 4 cycles.

In some embodiments, the pre-qPCR amplification is performed by incubating the reaction at 95° C. for 2 mins, followed by 1-10 (e.g., 4) cycles of 95° C. for 5 sec, 54° C. for 5 sec, and 72° C. for 5 sec.

qPCR

The method can include (d) performing real-time quantitative PCR (qPCR) on a DNA template to generate an amplified product corresponding to the target nucleic acid (e.g., miRNA) and detecting and/or quantifying the amplified product.

It is contemplated that in some embodiments (e.g., when the target nucleic acid is a DNA molecule), the reverse transcription and/or the pre-qPCR amplification procedure is not performed. Thus, disclosed are methods for the quantitative detection of two or more distinct target polynucleotides in a sample involving performing real-time qPCR on the sample (e.g., using universal or target-specific forward and reverse primers) to generate amplified products corresponding to the target polynucleotides, and detecting and/or quantifying each amplified product using fluorescence-based detection.

In any of the foregoing methods, real-time qPCR can be performed using a universal forward primer and a universal reverse primer. Since all targets are amplified using the same universal forward and reverse PCR primers, this can reduce or eliminate quantification bias. Thus, this approach reduces amplification bias that is present in current technologies. In some embodiments, the universal forward primer can contain the universal forward primer sequence of the first PCR primer and the universal reverse primer can contain the universal reverse primer sequence of the RT primer.

Conditions and parameters for performing qPCR are known in the art. In some embodiments, qPCR is performed by incubating the reaction at 95° C. for 2 mins (initial denaturation), followed by a desired number (e.g., 30) cycles of 95° C. for 5 sec (denaturation), 58° C. for 12 sec (annealing), and 72° C. for 5 sec (elongation).

In some embodiments, qPCR is performed by incubating the reaction at 95° C. for 2 mins (initial denaturation), followed by a desired number (e.g., 36) cycles of 95° C. for 5 sec, 24° C. for 12 sec, 44° C. for 12 sec, 58° C. for 12 sec, and 72° C. for 12 sec. Fluorescent data can be captured at each step of 24, 44, 58, and 72° C. incubation.

Like other qPCR methods, the disclosed methods can be quantitative, semi-quantitative, or qualitative. In some embodiments, for absolute quantification, a standard curve is used for each target. In absolute quantification using the standard curve method, one can quantitate unknowns based on a known quantity. First a standard curve is created; and then unknowns are compared to the standard curve to extrapolate a value.

dPCR

The method can include (e) performing digital PCR (dPCR) on a DNA template to generate an amplified product corresponding to the target nucleic acid (e.g., DNA or RNA or miRNA) and detecting and/or quantifying the amplified product.

It is contemplated that in some embodiments (e.g., when the target nucleic acid is a DNA molecule), the reverse transcription and/or the pre-qPCR amplification procedure is not performed. Thus, disclosed are methods for the quantitative detection of two or more distinct target polynucleotides in a sample involving performing digital PCR on the sample (e.g., using universal or target-specific forward and reverse primers) to generate amplified products corresponding to the target polynucleotides, and detecting and/or quantifying each amplified product using fluorescence-based detection.

In any of the foregoing methods, dPCR can be performed using a universal forward primer and a universal reverse primer or target specific forward and reverse primers.

Conditions and parameters for performing dPCR are known in the art. dPCR can be performed by incubating the reaction at 95° C. for 2 mins (initial denaturation), followed by a desired number (e.g., 30) cycles of 95° C. for 5 sec (denaturation), 58° C. for 12 sec (annealing), and 72° C. for 5 sec (elongation). During or at the end of dPCR cycle, fluorescence data can be captured by collecting fluorescence data at 24° C. for 12 sec, 44° C. for 12 sec, 58° C. for 12 sec, and 72° C. for 12 sec.

Isothermal Amplification

The method can include (I) performing isothermal amplification on a DNA template to generate an amplified product corresponding to the target nucleic acid (e.g., DNA or RNA or miRNA) and detecting and/or quantifying the amplified product.

It is contemplated that in some embodiments (e.g., when the target nucleic acid is a DNA molecule), the reverse transcription and/or the pre-qPCR amplification procedure is not performed. Thus, disclosed are methods for the quantitative detection of two or more distinct target polynucleotides in a sample involving performing isothermal amplification on the sample (e.g., using universal or target-specific forward and reverse primers) to generate amplified products corresponding to the target polynucleotides, and detecting and/or quantifying each amplified product using fluorescence-based detection.

In any of the foregoing methods, isothermal amplification can be performed using set of primers recommended for isothermal amplification procedure.

Conditions and parameters for performing isothermal amplification are known in the art. Isothermal amplification can be performed by incubating the reaction at a constant temperature (30 to 65° C.). During or at the end of isothermal amplification cycle, fluorescence data is captured by collecting fluorescence data at 24° C. for 12 sec, 44° C. for 12 sec, 58° C. for 12 sec, and 72° C. for 12 sec.

Detection of Target Nucleic Acids

In some embodiments, the nucleic acid targets, such as amplicons e.g., of miRNA targets, that are subject to the disclosed methods are detected using traditional RT-PCR detection technology. Traditionally, there are generally two types of measurements to acquire the fluorescent signal from the PCR product. The first type relies on DNA binding dyes, such as SYBR Green I, which binds nonspecifically to double-stranded DNA (dsDNA) and emits an enhanced fluorescence. The other type is a probe-based approach. These probes are sequence specific, and most of them use fluorescence resonance energy transfer (FRET) as the reporting mechanism and use the 5'-exonuclease activity of the DNA polymerase to detect PCR amplification in real time and some of them use fluorescence from probe bound to the amplified PCR products by competitive hybridization and contact quenching. Examples include, but are not limited to, TaqMan probes, FRET hybridization probes, molecular beacons, competitive hybridization probes, and scorpion probes. See, e.g., Yang and Tan, "Application of Molecular Beacons in Real-Time PCR," *Molecular Beacons*, 45-59 (2013), doi: 10.1007/978-3-642-39109-5_3; Li Q, et al., Nucleic Acids Res., 30(2):E5 (2002); and U.S. Pat. Nos. 7,799,522, and 8,192,937.

In some embodiments, the nucleic acid targets, including, but not limited to amplicons of miRNA targets, can be detected using an improved multiplexing detection strategy provided herein. In some embodiments, detection of the desired target nucleic acids can rely on the use of detection probes (e.g., that fluoresce when bound to the specific target) and quencher oligonucleotides that quench (e.g., reduce or eliminate) the signal (e.g., fluorescence) of detection probes that are unbound to the specific target. In some embodiments, detection of the desired target nucleic acids can rely on the use of molecular beacons (see, for example, FIGS. 4A-4C which illustrate molecular beacon design and use thereof for detection of a target) or fluorescently labeled primers.

In standard or conventional color multiplexing, one target is typically detected in each fluorescent channel. The disclosed methods are unique in employing thermodynamic properties of detection probe and quencher oligonucleotide complexes and/or thermodynamic properties of molecular beacons to facilitate single color multiplexing and multi-color multi-multiplexing.

During a typical PCR cycle including high-temperature denaturation (e.g., 95° C.), lower-temperature annealing (e.g., 58° C.), and intermediate temperature elongation (e.g., 72° C.), detection probe-quencher oligonucleotide complexes are denatured during the denaturation (or melting) step, resulting in the detection probe becoming fluorescent. During the annealing step, in the absence of the target, the detection probe and quencher oligonucleotide will remain hybridized, and thus, the detection probe will be non-fluorescent (i.e., the fluorescence quencher will quench signal from the fluorophore). In the presence of the target, however, the detection probe is preferably hybridized with the target. Fluorescence will be produced as a result. During the extension step, the detection probe is displaced off the targets. When fluorescent readings are acquired at the annealing temperature in a series of PCR cycles, the signal strength increases in proportion to amplicon accumulation. Thus, by measuring the fluorescence during each annealing step of a PCR reaction, amplification can be tracked in a real-time format.

Disclosed detection approaches allow for detection of a single target molecule or multiple (e.g., 2, 3, 4, 5, 6 or more) distinct target molecules at the same time. In some embodiments, multiple (e.g., 2, 3, 4, 5, 6 or more) distinct target molecules can be detected using a plurality of distinct probes (e.g., 2, 3, 4, 5, 6 or more) having different fluorophores for each distinct target molecule.

In some embodiments, multiple (e.g., 2, 3, 4, 5, 6 or more) distinct target molecules can be detected using two or more groups of detection probes (e.g., 2, 3, 4, 5, 6 or more). Preferably, each group of detection probes includes an identical fluorophore across all the probes in the group. In some embodiments, the distinct detection probes within each group contain a tag different in sequence and/or size from that of other probes in the group, or the quencher oligo are fully complementary to probe oligo that is fully complementary to target sequence without the need for a tag. The probes are each able to hybridize (detect) a distinct target amplified product. Thus, in some embodiments, the multiplexing approach allows use of multiple colors (fluorophores) for detection of multiple targets for each color (fluorophore). For example, each group of detection probes can include 3-4 distinct detection probes having the ability to detect 3-4 distinct target polynucleotides such as miRNAs within the same color. Thus, for example, a method using six different fluorophores with 3-4 distinct detection probes per fluorophore, can be used to detect 18-24 different targets simultaneously.

In some embodiments, multiple (e.g., 2, 3, 4, 5, 6 or more) distinct target molecules can be detected using a plurality of probes (e.g., 2, 3, 4, 5, 6 or more) having identical fluorophores regardless of the target molecule that the detection probe binds. In some embodiments, 3 distinct targets are detected per fluorophore. In some embodiments, 4 distinct targets are detected per fluorophore. In some embodiments, 5 distinct targets are detected per fluorophore. In some embodiments, 6 distinct targets are detected per fluorophore.

The multiple amplicons within the same color can be differentiated based on the differential thermodynamic stability of different detection probe-quencher oligonucleotide complexes or molecular beacons. Fluorescence can be quantified at specific temperatures corresponding to the melting temperatures of the different detection probe-quencher oligonucleotide complexes, followed by deconvolution of the fluorescent data. At low temperatures, the detection probe and corresponding quencher oligonucleotide are fully bound, thereby quenching fluorescence from detection probes not bound to a target. As the temperature is increased (e.g., beyond the Tm of the detection probe-quencher oligonucleotide complex), the detection probe-quencher oligonucleotide complex dissociates, resulting in increased fluorescence. Thus, for multiplexing within each individual fluorescent channel/color, the increase in fluorescence at every measured interval reflects the amount of a specific detection probe not bound to its target as measured by pre-designed Tm of the unbound detection probe-quencher oligonucleotide complexes, which in turn indirectly corresponds to the amount of multiple templates at that cycle. Thus generally, for a particular detection probe, as the available template increases with each cycle, the increase in fluorescence at the temperature interval specific for that detection probe will be less with increasing cycle number (because there will be less detection probe not bound to its target).

Figure 2A:
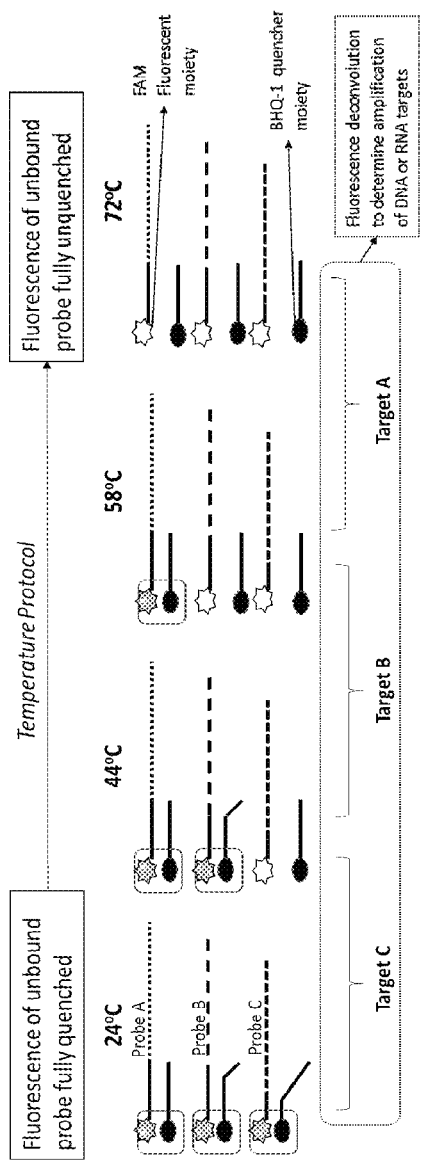
FIG. 2A is a schematic depiction of a single-color multiplex detection of three targets using a common quencher oligo. After 95° C. denaturation, the reaction is cooled down to 24° C. During this step, fluorescent detection probes bind to respective targets and any detection probe not bound to target is quenched by the quencher oligonucleotide. At a temperature of 44° C., unbound probe C fully dissociates from quencher whereas unbound probe A and B are still quenched. At 58° C., unbound probes B and C fully dissociate from the quencher, whereas unbound probe A is still quenched. At 72° C., unbound probes A, B and C fully dissociate from the quencher. The difference in fluorescence intensity at these temperatures is used to differentiate targets amplified in the same color. A tag sequence fully or partly complementary to common quencher oligo can be incorporated to the amplified DNA through primer design as further illustrated in figures below. The probe can contain a sequence that binds specifically to the target nucleic acid (e.g., target DNA or RNA or miRNA of interest). The tag sequence can be common or specific to each probe.
Figure 2B:
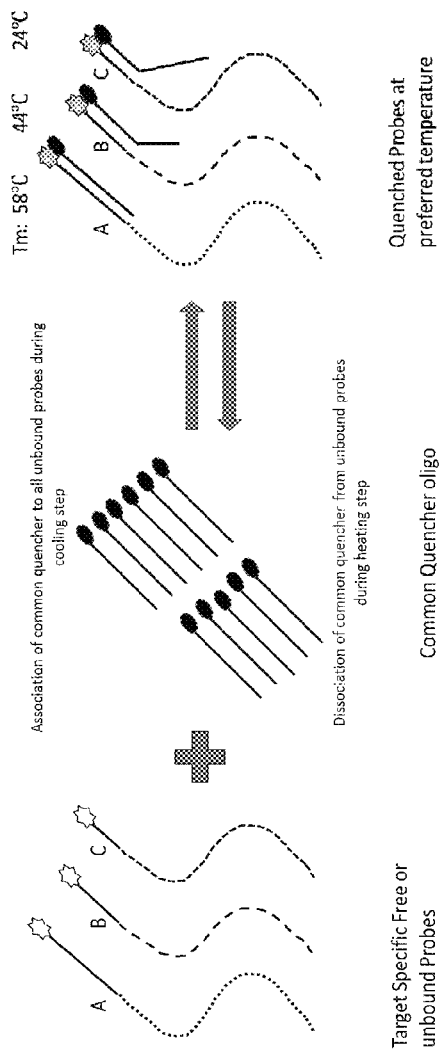
FIG. 2B illustrates the common quencher principles as applied to detection of different DNA or RNA or miRNAs using three different detection probes (Probes A, B and C) having tag sequences of distinct sizes. A common quencher oligonucleotide is used to quench signal from all the detection probes, but at different temperatures for each detection probe depending on the degree of hybridization.
Figure 3A:
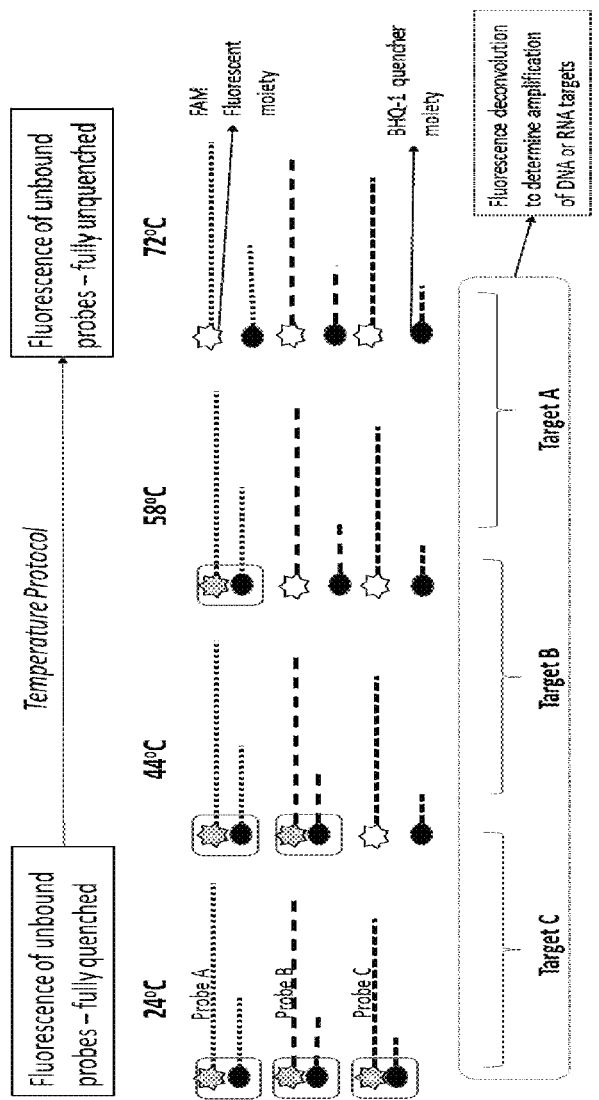
FIG. 3A is a schematic depiction of a single-color multiplex detection of three targets using specific quencher oligos to measure unbound probes. The overall principles and methodology are similar to that of FIG. 2A, however, rather than a common quencher, different, specific quencher oligos are used to measure the amount of each set of unbound probes, e.g., Probes A, B, and C. Each specific quencher oligo and unbound probe complex is designed to bind and dissociate at specific temperatures. The probe oligo contains sequence fully specific to the target DNA or RNA of interest whereas each quencher oligo is designed to bind specifically to each of the free probe set.
Figure 3B:
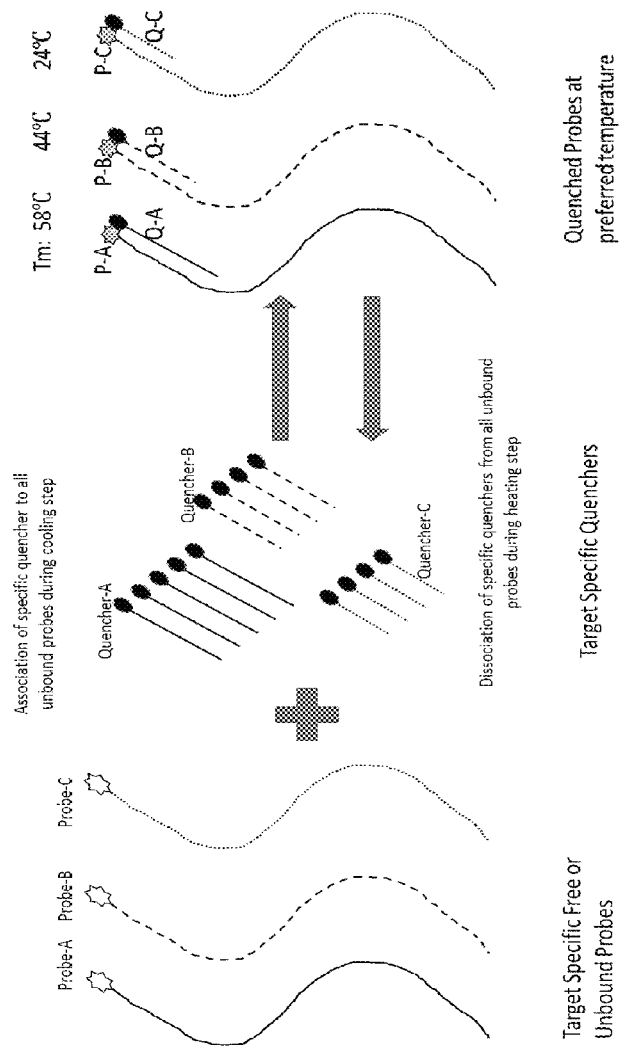
FIG. 3B illustrates the specific quencher principles as applied to detection of different e.g., DNA or RNA or miRNAs using three different detection probes (Probes A, B and C) having distinct sequences. A specific quencher oligonucleotide is used for each detection probe to quench signal therefrom. The temperatures at which each detection probe is quenched can depend on the degree of hybridization between the detection probe and corresponding sequence in the quencher oligonucleotide.

This single-color multiplexing method can use either a common quencher oligonucleotide (see e.g., FIGS. 2A-2B) or target specific quencher oligonucleotide that binds to the detection probe (see e.g., FIGS. 3A-3B). The extent of binding between the detection probe and quencher oligonucleotide is dependent on the length of complementarity between quencher oligonucleotide and detection probe sequences in relation to the temperature, based on the principle of complementary binding at lower temperatures to fully dissociation as the temperature increases. In some embodiments, extent of complementary can be used instead or in addition to length. For examples, detection probes having 80, 90 or 100% complementarity across the same length of binding region to quencher oligonucleotide can result in complexes with different melting temperatures.

Typically, the detection probe(s) and quencher oligonucleotide(s) can associate by hybridization and are separate nucleic acid molecules. Thus, in some embodiments, the detection probes and quencher oligonucleotide(s) are not a single molecule that forms as a hairpin or a stem-loop.

By way of example, the fluorescence signal detected at each designated temperature for a single-color multiplex quantitative detection of three distinct target miRNAs is illustrated in Table 1. For the purposes of this illustration, the melting temperatures correspond to the melting temperatures for the detection probe-quencher oligonucleotide complexes depicted in FIG. 2A.

TABLE 1

Fluorescence detected at various temperatures.

| Tm (° C.) | Target-specific fluorescence signal | | | Unquenched probe signal | | |
|---|---|---|---|---|---|---|
| | miRNA A | miRNA B | miRNA C | Probe A | Probe B | Probe C |
| 72 | ✓ | ✓ | ✓ | ✓ | ✓ | ✓ |
| 58 | ✓ | ✓ | ✓ | | ✓ | ✓ |
| 44 | ✓ | ✓ | ✓ | | | ✓ |
| 24 | ✓ | ✓ | ✓ | | | |

*Target-specific fluorescence signal corresponds to the fluorescence emitted by detection probe when bound to its target miRNA.
*Unquenched probe signal corresponds to the fluorescence emitted by a detection probe when it is not bound to the target miRNA nor its corresponding quencher oligonucleotide (detection probe-quencher oligonucleotide complex is denatured).

In the above example, after the denaturation (e.g., at 95° C.), all nucleic acid molecules are denatured/single stranded. Fluorescence is captured at pre-determined temperatures depending on the predicted melting temperatures of the complexes that will be formed during the PCR reaction. In the example illustrated in Table 1, the fluorescence is measured at 24° C., 44° C., 58° C., and 72° C. The forward primer and reverse primer annealing occur at or below 58° C. and primer extension occurs at 72° C. When the PCR reaction is cooled down to 24° C., this allows binding of detection probe to specific amplified target and binding of unbound detection probe to quencher oligonucleotide during cooling step from 95 to 24° C. When the temperature is raised to 44° C., probe C is fully fluorescent because it is fully separated from the quencher oligonucleotide and/or bound to its target. Probes B and C not bound to target are fully quenched. At 58° C., probes B and C are fully fluorescent because they are fully separated from the quencher oligonucleotide(s) and/or bound to their respective targets. Any probe A not bound to its target is fully quenched. At 72° C., probes A, B, and C are fully fluorescent.

Since the detection probes are designed to bind to the target at temperatures higher (e.g., 72° C. or more) than the annealing temperature, as the temperature cools down (after denaturation), each detection probe is specifically bound to its target amplification product. Thus, there is target-specific fluorescence signal for each detection probe at 58° C., 44° C., 24° C., and 72° C. measured by amount of free fluorescent probe quenched as the PCR cycle progresses. At 24° C., detection probes A, B, and C (not bound to target) can form a sufficiently stable complex with their corresponding quencher oligonucleotides, resulting in quenching of probes their fluorescence. At 44° C., detection probes A and B (not bound to target) can form a sufficiently stable complex with their corresponding quencher oligonucleotide, resulting in quenching of their fluorescence. At 58° C., detection probe A (not bound to target) can form a sufficiently stable complex with its corresponding quencher oligonucleotide, resulting in quenching of probe A's fluorescence. At 72° C., all detection probe-oligonucleotide quencher complexes are destabilized.

Thus, at each temperature, the increase in fluorescence compared to the preceding lower temperature corresponds to the amount of a free detection probe (not bound to its target) that becomes fluorescent due to dissociation of quencher oligonucleotide-detection probe complex. As the amount of target template (or amplification product) increases with increasing cycle number, there will be less free detection probe (not bound to its target) that becomes fluorescent at every cycle. Thus, the fluorescence data can serve as a real-time, quantitative indicator of the amount of each amplified product.

Similarly, at the beginning and end of isothermal amplification, the method can be applied to determine co-amplification of multiple targets. This is same as in qualitative PCR with a first and last cycle performing temperature incubation step to determine co-amplified targets using fluorescence deconvolution. Because isothermal amplification does not require the same thermocyclying as in PCR, the fluorescence measurement need not be taken at every cycle but rather only at beginning and the end of the amplification reaction. A similar deconvolution process can be used to determine co-amplified targets.

As introduced above, these strategies can be expanded across multiple fluorophores to expand the reach of the multiplexing.

Single color multiplexing can also be performed using molecular beacons to detect multiple targets. In some embodiments, multiple (e.g., 2, 3, 4, 5, 6 or more) distinct target molecules can be detected at the same time. In some embodiments, multiple (e.g., 2, 3, 4, 5, 6 or more) distinct target molecules can be detected using a plurality of molecular beacons (e.g., 2, 3, 4, 5, 6 or more) having the identical fluorophore, but differing in the thermodynamic stability of the hairpin structures which the molecular beacons form.

Generally, in the absence of (or when not bound to) a target polynucleotide, each molecular beacon self-hybridizes to form a hairpin structure. For single color multiplexing, each hairpin structure preferably exhibits a unique melting temperature. The molecular beacons can be designed to have a desired melting temperature by adjusting the length/extent of complementarity of stem region in the hairpin. While formation of the hairpin structure can result in quenching of fluorescence, fluorescence can be unquenched at a temperature above the unique melting temperature for each molecular beacon. In some embodiments, fluorescence is measured at each unique melting temperature for each amplification (e.g., qPCR or dPCR or isothermal) cycle.

Thus, similar to the detection probe-quencher oligonucleotide approach, for multiplexing within a single fluorescent channel/color using the molecular beacon approach, the increase in fluorescence at every measured interval reflects the amount of a specific molecular beacon not bound to its target, which in turn indirectly corresponds to the amount of template at that cycle. Thus generally, for a particular molecular beacon, as the available template increases with each cycle, the increase in fluorescence at the temperature interval specific for that molecular beacon will be less with increasing cycle number (because there would be less molecular beacon not bound to its target). The molecular beacon approach can also be expanded across multiple fluorophores to expand the reach of the multiplexing.

Deconvolution of Fluorescence Data

In an exemplary embodiment, the deconvolution of fluorescence data can be performed as follows:
I. Introduction to the workflow:
  The system:
    The system (machine) readings are in fluorescence units (data).
    Followed by an analytical evaluation on the system, the captured fluorescent data is exported to an excel tab.
    The system has built-in capability to export the data to an excel tab.
    In some embodiments, the system can measure fluorescence in six colors (also referred as six channels) each with distinct fluorescence signal. The system measures and exports the data on all six colors:
      The fluorescent colors can be represented as T1, T2, T3, T4, T5, and T6.
  An analytical evaluation includes 36 cycles of fluorescence measurements, which encompasses one full run. The fluorescence is measured at all 36 cycles for each fluorescence colors.
    Cycles are C1 to C36 for all measured colors T1, T2, T3, T4, T5, and T6.
  Each cycle includes four steps collecting four fluorescent readings. Raw fluorescence readings are measured at each step (pre-determined temperatures) at each cycle for each color.
    Steps at each cycle for each color are S1, S2, S3, and S4.
  The fluorescent measurement data measured at the four steps at each cycle for each color will be deconvoluted to 18 targets (Target A to Target R)

Targets can be the biological analytes of interest to a particular human disease or disorder.

II. Data collection step:

The system collects the data for each color (T1 to T6), at each cycle (C1 to C36), and at every step (S1 to S4).

For example, colors 1 to 6 will have fluorescent readings at cycles C1 to C36 and at every step, S1 to S4; color-cycle-steps.

This is as shown below:
T1-C1-S1, S2, S3, S4 to T1-C36-S1, S2, S3, S4
T2-C1-S1, S2, S3, S4 to T2-C36-S1, S2, S3, S4
T3-C1-S1, S2, S3, S4 to T3-C36-S1, S2, S3, S4
T4-C1-S1, S2, S3, S4 to T4-C36-S1, S2, S3, S4
T5-C1-S1, S2, S3, S4 to T5-C36-S1, S2, S3, S4
T6-C1-S1, S2, S3, S4 to T6-C36-S1, S2, S3, S4

When the data is exported to an excel sheet, there will be S1 to S4 columns for each fluorescent color. For six fluorescent colors each with six steps, there will be total of 36 columns. The first column is cycle number C1 to C36. All 36 columns will have readings in rows starting from 2 to 37.

Abbreviated schematics of excel layout is shown as in Table 2 below:

TABLE 2

Representative layout of fluorescent data output.

| Cycles | Color T1 | | | | Color T2 | | | |
|---|---|---|---|---|---|---|---|---|
| | S1 | S2 | S3 | S4 | S1 | S2 | S3 | S4 |
| C1 | | | | | | | | |
| C2 | | | | | | | | |
| C3 | | | | | | | | |
| C4 | | | | | | | | |
| C5 | | | | | | | | |
| C6 | | | | | | | | |
| C7 | | | | | | | | |

Data deconvolution step:

After the collection of fluorescence readings, the data can be analyzed for each fluorescent color, at each cycle by using the following algorithm:

Subtract fluorescent readings between S2 and S1 (S2-51), S3 and S2 (S3-S2), and S4 and S3 (S4-S3) for each color and at each cycle Calculations are to be done for all Types (T1 to T6) and at each cycle (C1 to C36).

This data deconvolution step leads to fluorescent values for Targets A to R as indicated in the example below:

For example,
for T1 at cycle C1, Target A=(S2−S1), Target B=(S3−S2), and Target C=(S4−S3)
For T2 at cycle C1 Target C=(S2−S1), Target D=(S3−S2), and Target F=(S4−S3)
For T3 at cycle C1 Target E=(S2−S1), Target F=(S3−S2), and Target I=(S4−S3)
For T4 at cycle C1 Target J=(S2−S1), Target K=(S3−S2), and Target L=(S4−S3)
For T5 at cycle C1 Target M=(S2−S1), Target N=(S3−S2), and Target O=(S4−S3)
For T6 at cycle C1 Target P=(S2−S1), Target Q=(S3−S2), and Target R=(S4−S3)

S1 is 26° C., S2 is 44° C., S3 is 58° C., and S4 is 72° C.

Schematics of the analysis is shown in Table 3 below:

TABLE 3

Representative abbreviated layout of fluorescent data after deconvolution.

| Cycles | Color T1 | | | Color T2 | | | Color T3 | | |
|---|---|---|---|---|---|---|---|---|---|
| | Target A | Target B | Target C | Target D | Target E | Target F | Target G | Target H | Target I |
| C1 | S2 − S1 | S3 − S2 | S4 − S3 | S2 − S1 | S3 − S2 | S4 − S3 | S2 − S1 | S3 − S2 | S4 − S3 |
| C2 | S2 − S1 | S3 − S2 | S4 − S3 | S2 − S1 | S3 − S2 | S4 − S3 | S2 − S1 | S3 − S2 | S4 − S3 |
| C3 | S2 − S1 | S3 − S2 | S4 − S3 | S2 − S1 | S3 − S2 | S4 − S3 | S2 − S1 | S3 − S2 | S4 − S3 |
| C4 | S2 − S1 | S3 − S2 | S4 − S3 | S2 − S1 | S3 − S2 | S4 − S3 | S2 − S1 | S3 − S2 | S4 − S3 |
| C5 | S2 − S1 | S3 − S2 | S4 − S3 | S2 − S1 | S3 − S2 | S4 − S3 | S2 − S1 | S3 − S2 | S4 − S3 |
| C6 | S2 − S1 | S3 − S2 | S4 − S3 | S2 − S1 | S3 − S2 | S4 − S3 | S2 − S1 | S3 − S2 | S4 − S3 |

Data transformation and plotting step:
  The values are going to be in decreasing (negative) fluorescent values with increase in cycles. The data can be transformed into increasing (positive) scale. For example, subtract each fluorescent value for Target A with a number so that the values can be transformed into an increasing order.
  For example, if the values for C1, C2, C3, to C36 is 980, 950, 900, to 18, respectively, then subtracting all the values with 1000, will transform this data into a positive scale.
  Plot the subtracted fluorescence readings for each Targets A to R collected at each cycle (C1 to C36).
The curve will transform from the graph depicted in FIG. 1A, left side (before data transformation) to FIG. 1A, right side (after data transformation):
  Take average of first three to 12 subtracted fluorescence values, determine 3SD and set this as a baseline (red line in the right graph)
    Plot the baseline from previous step to be on this fluorescence signal curve.
The graph can also be normalized to the base; for example, to start at level "0" or slightly below "0"
The X-axis value at which curve crosses the X-axis to be reported. In this case, green arrow, value of 12. This value is called as cycle threshold.
All eighteen Targets (A to R) will have a curve similar to above and all eighteen Targets (A to R) will have values, cycle threshold, that are reported out.

Applications of the Methods

The disclosed methods can be used in any application where detection of nucleic acids, such as miRNAs, is useful. For example, dysregulation of miRNAs is implicated in many diseases, and various miRNAs have been proposed as disease biomarkers (e.g., diagnostic and/or prognostic biomarkers).

Thus, in some embodiments, the disclosed methods are used to detect and/or quantify disease associated nucleic acids (mRNAs, miRNAs, etc.). In some embodiments, the methods are used to detect and/or quantify circulating miRNAs (e.g., miRNAs in exosomes or other extracellular vesicles). Since the target nucleic acids can be isolated from a sample (e.g., biological fluid), the disclosed methods can further include isolation of a nucleic acid. For example, in some embodiments, the methods include isolation of or obtaining a sample containing nucleic acids and detecting one or more target polynucleotides in the sample.

In some embodiments, the methods are used to detect and/or quantify miRNAs that can be used to diagnose a disease in a subject (e.g., cancer, cardiovascular diseases, liver diseases, sepsis, causative agents of infectious diseases, genetic disorders, metabolic disorders, or neurodegenerative diseases). In some embodiments, the methods are used to detect and/or quantify miRNAs that can be used to prognose a disease in a subject (e.g., cancer, liver diseases, sepsis, causative agents of infectious diseases, genetic disorders, metabolic disorders, cardiovascular diseases, or neurodegenerative diseases). In some embodiments, the methods are used to detect and/or quantify miRNAs that can be used to predict therapeutic outcome of a disease (e.g., cancer, liver diseases, sepsis, causative agents of infectious diseases, genetic disorders, metabolic disorders, cardiovascular diseases, or neurodegenerative diseases). In some embodiments, the methods are used to detect and/or quantify miRNAs that can be used to predict drug resistant or refractory disease (e.g., cancer, liver diseases, sepsis, causative agents of infectious diseases, genetic disorders, metabolic disorders, cardiovascular diseases, or neurodegenerative diseases).

For example, in some embodiments, a disease or disorder can be diagnosed by the presence of dysregulated miRNA, e.g., either up or down regulated relative to wildtype. In some embodiments, a series of measurements are made on different samples from the same subject over time to, for example, monitor disease progression and/or treatment effectiveness.

It is to be understood that an increase, decrease or lack thereof (unchanged), in a target polynucleotide can be relative to a control, which need not be stated. Thus, in some embodiments, measurements are compared to a control. One of ordinary skill in the art can determine the appropriate control. For example, in some embodiments, measurement of a target polynucleotide is relative to a state prior to administration a therapeutic, or relative to levels in a subject who is not administered a therapeutic. In some embodiments, measurement of a target polynucleotide is relative to an endogenous or exogenous (e.g., spike-in) control. The endogenous or exogenous control can be a single reference polynucleotide or a pool of two or more reference polynucleotides.

IV. Kits

Also disclosed are kits for carrying out the disclosed methods. Compositions, reagents, and other materials can be packaged together in any suitable combination as a kit useful for performing, or aiding in the performance of, the disclosed methods. It is useful if the kit components in a given kit are designed and adapted for use together in the disclosed methods. For example, disclosed are kits with one or more oligonucleotides (e.g., RT primer, blocker oligonucleotides, PCR primers, detection probes, quencher oligonucleotides), buffers, and/or enzymes. The kits may include a sterile needle, swab, syringe, ampule, tube, container, or other suitable vessels for isolating samples and extracting nucleic acids therefrom, holding assay components and/or performing the assay. The kits may include instructions for use.

The kit can include a sufficient quantity of reverse transcriptase, a DNA polymerase, oligonucleotides, and/or reaction buffer, or any combination thereof, for the performing the detection assays described above. A kit may further include instructions pertinent for the particular embodiment of the kit, such as providing conditions and steps for operation of the method.

The kits may contain oligonucleotides (e.g., primers) suspended in an aqueous solution or as a freeze-dried or lyophilized powder, for instance. The container(s) in which the primers are supplied can be any conventional container that is capable of holding the supplied form, for instance, microfuge tubes, multi-well plates, ampoules, or bottles. One or more control probes, primers, and or nucleic acids also may be supplied in the kit. For example, the kit may include one or more positive control samples (such as a sample including a particular nucleic acid) and/or one or more negative control samples (such as a sample known to be negative for a particular nucleic acid).

In some embodiments, the kit can contain instructions for detecting a target nucleic acid. This can include for example, instructions and/or software for data analysis.

The present invention will be further understood by reference to the following non-limiting examples.

EXAMPLES

The following example is put forth so as to provide those of ordinary skill in the art with a complete disclosure and description of how the compounds, compositions, articles, devices and/or methods claimed herein are made and evaluated, and are intended to be purely exemplary and are not intended to limit the disclosure.

Example 1: Reverse Transcription and Quantitative Detection of Multiple miRNAs, miR-223, miR-16 and Cel-miR-39 in FAM™ Channel Using Common Quencher Oligo Materials and Methods
Synthetic miRNA
miRNAs, miR-223 (UGUCAGUUUGU-CAAAUACCCCA (SEQ ID NO:1)), miR-16 (UAGCAGCACGUAAAUAUUGGCG (SEQ ID NO:2)), and miR-39 (UCACCGGGUGUAAAUCAGCUUG (SEQ ID NO:3)) were synthesized commercially using the service provided by Integrated DNA Technologies. Synthesized miR-223, miR-16 and Cel-miR-39 were dissolved in TE to obtain 100 nM stock concentration. Using the nmol yield information, copy number was determined.

Figure 6A:
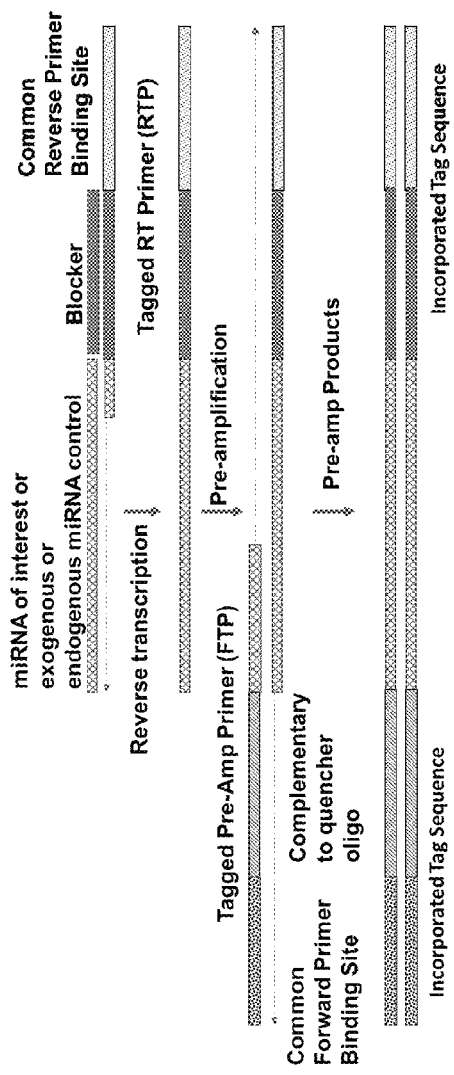
FIG. 6A is a schematic depicting the reverse transcription and First PCR (1$^{st}$ PCR) steps for miRNA detection. The tagged RT primer includes a portion complementary to the target miRNA, and a tag collectively containing a blocker binding site and reverse primer binding site. The tagged 1$^{st}$ PCR primer includes a portion complementary to the target miRNA, and a tag collectively containing a forward primer binding site and a sequence that is complementary to the quencher oligonucleotide. The reverse transcription and 1$^{st}$ PCR steps produce double stranded DNA templates incorporating the tagged sequences.
Figure 6B:
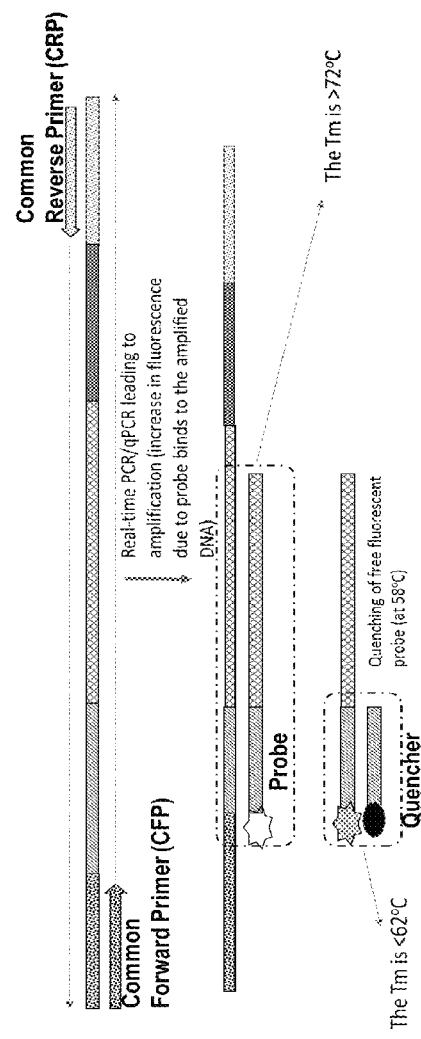
FIG. 6B is a schematic depicting the universal PCR amplification and detection approach using universal forward and reverse primers and tag/miRNA specific probe.
Figure 6C:
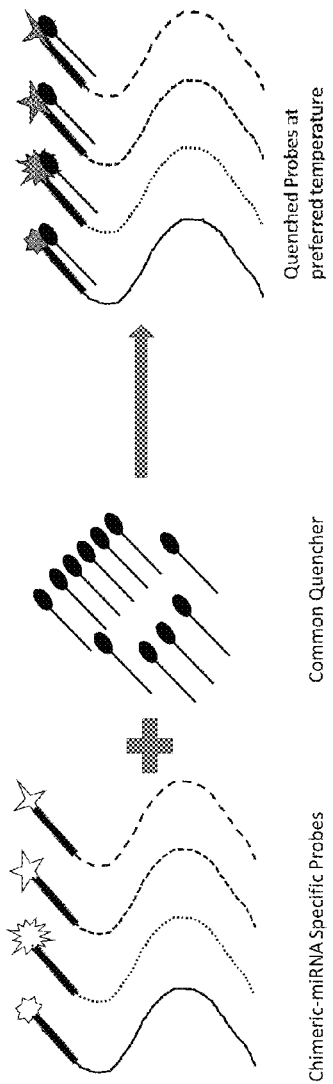
FIG. 6C is a schematic depicting multiplex miRNA detection using a contact quenching with universal quenching sequence which allows for multiple miRNA detection in the same PCR reaction. Each probe is specific to a target miRNA and includes a distinct fluorophore, a common tag sequence (fully complementary to the quencher oligonucleotide sequence), and a region complementary to its target miRNA. Any unbound fluorescent probe is quenched by a common quencher oligonucleotide at a specified temperature that allows complementary binding of quencher oligonucleotide to the fluorescent probe based on the tag sequence. The quencher oligonucleotide sequence is common for all the probes. The quencher oligonucleotide contains distinct fluorescence quenchers corresponding to the distinct fluorophores on the detection probes.
Figure 6D:
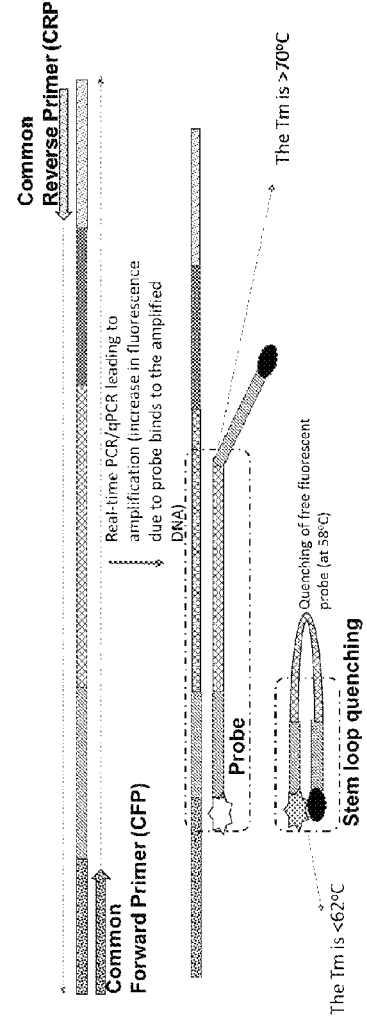
FIGS. 6D and 6E are schematics depicting PCR based detection using molecular beacons.
Figure 6E:
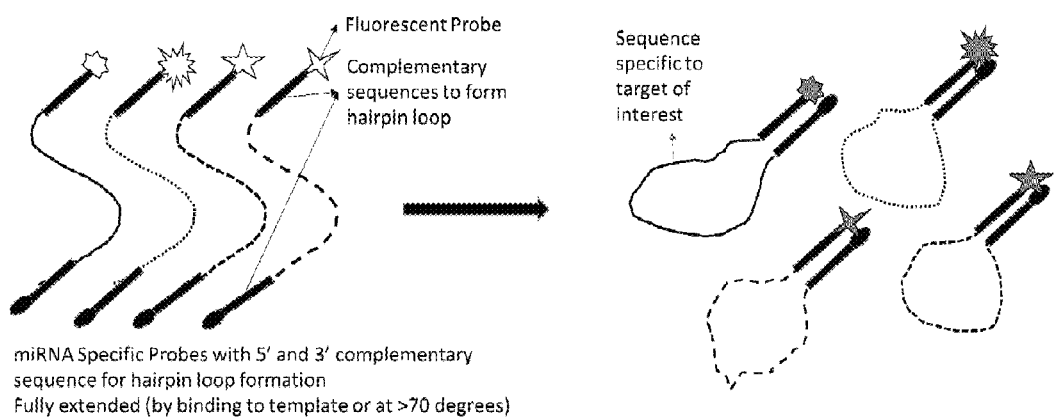

RT and PCR Primer and Probe Designs
RT primer, 1$^{st}$ PCR primers, common primers, and probes for miRNAs detection were designed using the approach as shown in FIGS. 6A-6B. All primers and probes were carefully designed while considering the reaction temperatures. The melting temperatures (Tm) of the tagged RT primer (that binds to miRNA) and 1$^{st}$ PCR primer (that is complementary to miRNA) were kept in the range of 12-18° C. and 42-46° C., respectively. The Tm of common primers, PCR forward primer and PCR reverse primer was kept between 58-62° C., designed using Oligo Analyzer Tool (Integrated DNA Technologies). Probe specific to the miRNA of interest and tags will bind to the template at >72° C. and unbound probes will be quenched at 58-62° C. by a common quencher.

```
miR-223 RT Primer:
                                        (SEQ ID NO: 4)
5'-TGCAATAAATCCCGCATGCTCGACGCAGTCCCTCACATGGGGT-3' miR-16 RT Primer:
                                        (SEQ ID NO: 5)
5'-TGCAATAAATCCCGCATGCTCGACGCAGTCCCTCACACGCCAA-3'

Cel-miR-39 RT Primer:
                                        (SEQ ID NO: 6)
5'-TGCAATAAATCCCGCATGCTCGACGCAGTCCCTCACACAAGCT-3'

Common-RT-Blocker:
                                        (SEQ ID NO: 7)
5'-TGTGAGGGACTG-Pho-3' miR-223 Probe:
                                        (SEQ ID NO: 8)
5'-FAM™-AGGCACGCAGGCTGTCAGTTTGTCAAA-Pho-3'
(58° C. melting)

miR-16 Probe:
                                        (SEQ ID NO: 9)
5'-FAM™-AGGCACGCATAGCAGCACGTAAATA-Pho-3'
(44° C. melting)

Cel-miR-39 Probe:
                                        (SEQ ID NO: 10)
5'-FAM™-AGGCACGTCACCGGGTGTAAAT-Pho-3'
(24° C. melting)

Common quencher:
                                        (SEQ ID NO: 11)
5'-GCCTGCGTGCCT-BHQ®1-3'

PCR Forward Primer:
                                        (SEQ ID NO: 12)
5'- GCGCTATCCGACAATTTCCA-3'

PCR Reverse Primer:
                                        (SEQ ID NO: 13)
5'- TAAATCCCGCATGCTCGACG-3' miR-223 First Primer:
                                        (SEQ ID NO: 14)
5'-AGTCGCGCTATCCGACAATTTCCAATATCAGGCACGCAGGCTGT
CAGTTTGT-3' miR-16 First Primer:
                                        (SEQ ID NO: 15)
5'-AGTCGCGCTATCCGACAATTTCCAATATCAGGCACGCATAGCAG
CACG-3'

Cel-miR-39 First Primer:
                                        (SEQ ID NO: 16)
5'-AGTCGCGCTATCCGACAATTTCCAATATCAGGCACGTCACCGGG
T-3'.
```

For RT Primer, the bolded sequences represent the Common Reverse primer binding site, italicized represent the tag to which common-RT-blocker will bind, bolded and italicized represent the sequence complementary to specific miRNAs to prime reverse transcription reaction.

For First Primer, bolded nucleotides—Common PCR Forward Primer/binding site; italicized nucleotides—sequence complementary to common quencher; and bolded and italicized nucleotides—first Primer sequence to bind/prime cDNAs.

All the above oligos were designed and synthesized using the services provided by IDT or LGC-Biosearch Technologies.

Reverse Transcription and First PCR
Reverse transcription (RT) was performed using MMLV High Performance Reverse Transcriptase (Lucigen) using a miRNAs-223, 16 and 39 specific RT primer containing the tag sequences. RT conditions included incubation at 50° C. for 1 min, 16° C. for 10 mins, 25° C. for 10 min, 37° C. for 10 mins, and 85° C. for 5 minutes. RT reaction included 0.1 µM RT primer, 0.5 µM dNTP mix, 2 µl of 10×RT buffer, 2 µl of 100 mM DTT, and 0.5111 (100 U) of RT enzyme in a total reaction volume of 20111.

First PCR (1$^{st}$ PCR) cycle was carried out using Klentaq1 (DNA Polymerase Technology) in a reaction volume of 20 µl containing 2 µl of 10× Klentaq1 PCR buffer, 0.25 µM dNTP mix, 2.5 mM MgCl$_2$, 0.02 µM miR-122 First Primer, 0.1 µl Klentaq1 enzyme and 5 µl of RT product. First PCR conditions included 95° C. for 2 mins initial denaturation step followed by 4 cycles at 95° C. for 5 sec, 56° C. for 5 sec and 72° C. for 5 sec. At this step, miRNAs are reverse transcribed, tagged sequences are incorporated, and fully incorporated tag sequences are enriched. This serves as template for qPCR. The concentration of First PCR primer was at 0.02 µM.

qPCR
Product from the RT and 1$^{st}$ PCR was used to setup the PCR using EconoTaq Polymerase (Lucigen). PCR reactions were carried out at 58° C. annealing and 72° C. extension. At this annealing temperature, PCR forward and reverse primers bind and amplify fully incorporated sequences. The probe then binds to the miRNA-of-interest specifically in real-time. Any unbound probe is quenched by the common quencher.

PCR was performed on iCycler iQ qPCR system (Bio-Rad) using the following PCR run conditions for amplification of miRNAs (223, 16, and 39) cDNAs:

Step 1: 1 Cycle 95° C. for 2 minutes

Step 2: 28 Cycles

Step 2A: 95° C. for 5 sec (denaturation step)

Step 2B: 24° C. for 12 sec (data capture step)

Step 2C: 44° C. for 12 sec (data capture step)

Step 2D: 58° C. for 12 sec (annealing and data capture step)

Step 2E: 72° C. for 12 sec (primer extension and data capture step)

Fluorescence was measured at 24° C., 44° C., 58° C. and 72° C. in FAM™ channel Amplification of miR-223, miR-16, and Cel-miR-39 cDNAs were detected in post PCR using the deconvolution algorithm.

The qPCR reaction contained 2 µl of 10× EconoTaq PCR Buffer, 2.5 mM MgCl$_2$, 0.25 µM dNTP mix, 1 µM each of common forward and reverse primers, 0.2 µM of miR-122 probe, 2 µM of quencher, 1 U of EconoTaq Polymerase, 5 µl of First PCR product. Total qPCR reaction volume was 20 µl.

Results

Figure 7A:
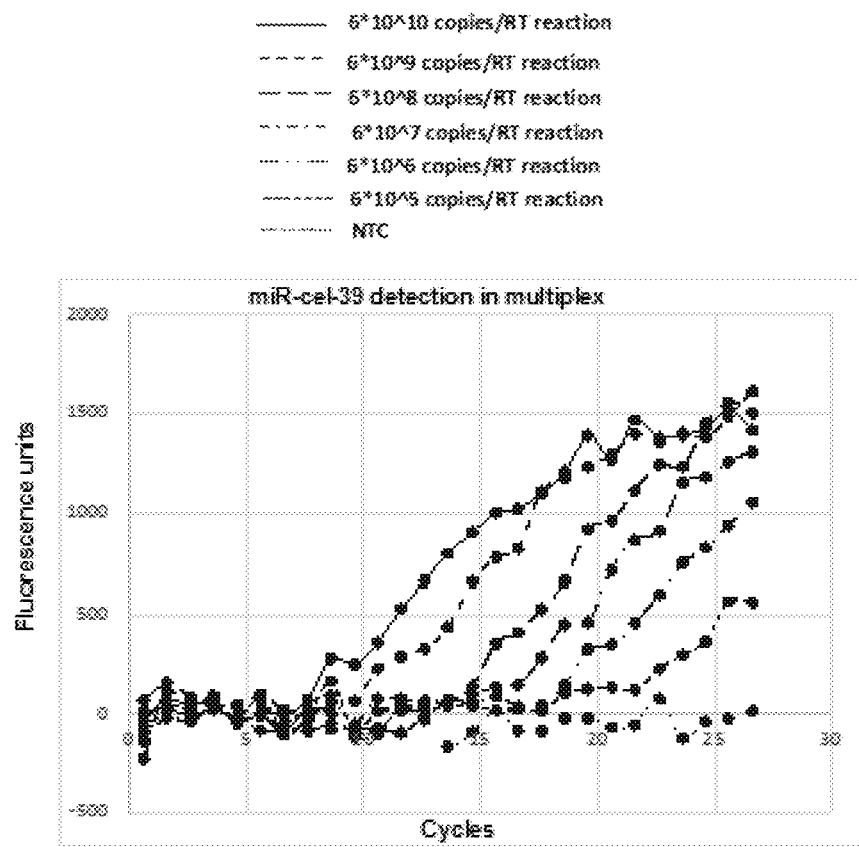
FIGS. 7A-7F are graphs illustrating the results of reverse transcription (RT), pre-amplification, and detection of three miRNA targets using a common quencher detection approach. Synthetic miRNAs (miR-223, miR-16 and Cel-miR-39) were used as template in RT as described in the text and, pre-amplified and detected in fluorescein (FAM™) channel using single color multiplex detection with a common quencher oligo. RT-NTC=no template control.
Figure 7B:
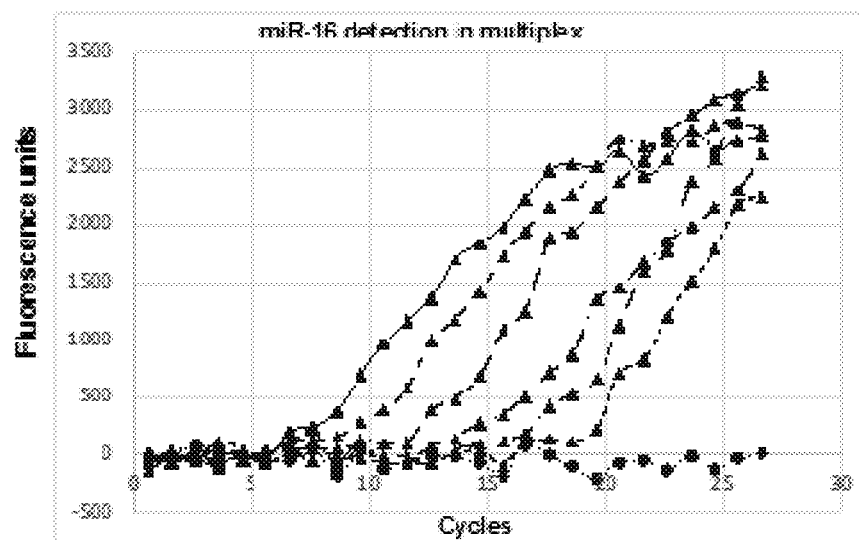
Figure 7C:
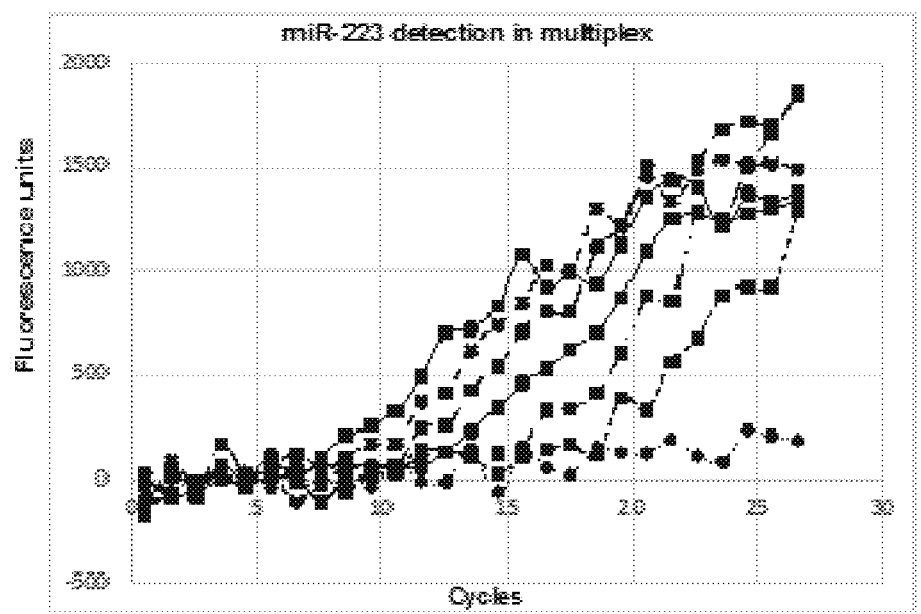
Figure 7D:
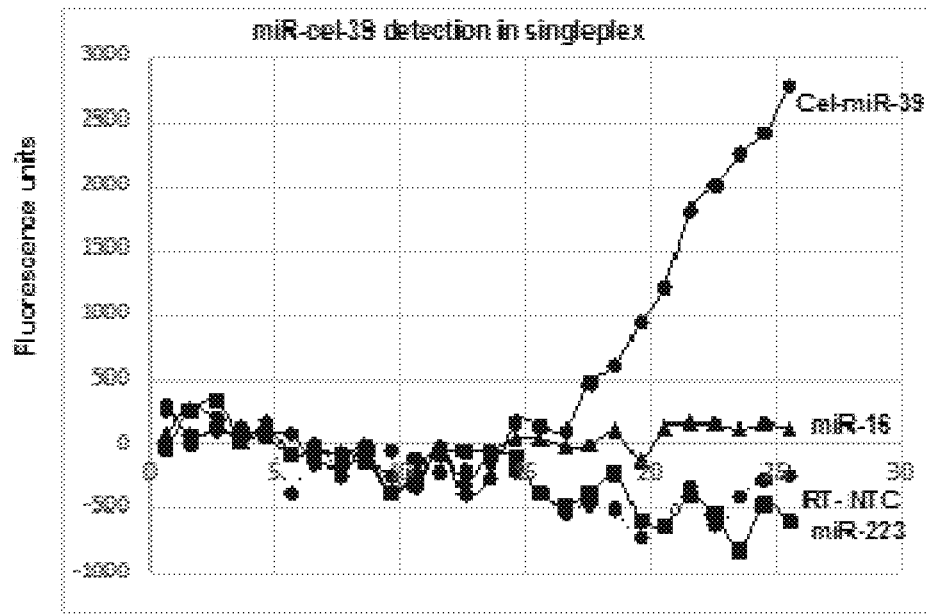
Figure 7E:
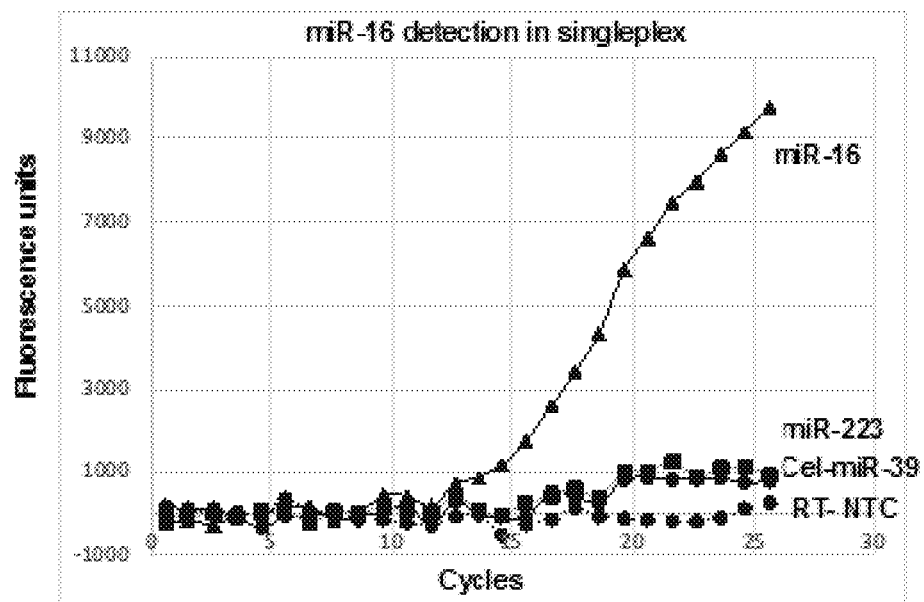
Figure 7F:
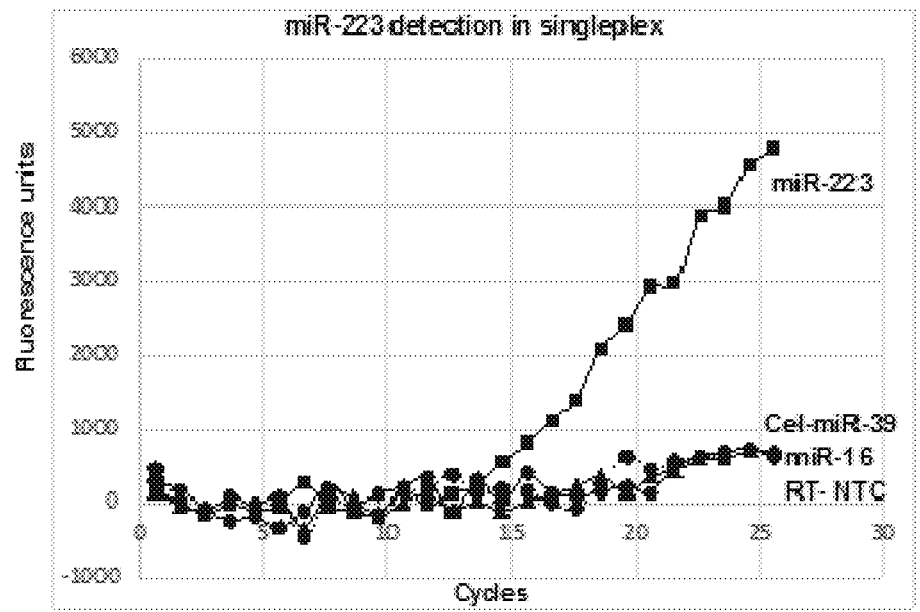

To demonstrate the proof-of-concept, miR-cel-39, miR-16 and miR-223 synthetic miRNAs were pooled (multiplex) each at 6*10^10, 6*10^9, 6*10^8, 6*10^7, 6*10^6, 6*10^5 copies, reverse transcribed followed by pre-amplification/qPCR and fluorescent data analyses. As shown, the method was able to detect and differentiate miR-cel-39, miR-16 and miR-223 in FAM™ channel (FIG. 7A, 7B, 7C) using common quenching approach. To confirm, there is no cross-reactivity of fluorescent signals, miR-cel-39, or miR-16 or miR-223 miRNA templates at 6*10^7 copies was reverse transcribed individually (singleplex) followed by pre-amplification/qPCR and fluorescent data analyses (FIG. 7A, 7B, 7C). Appropriate negative controls were included. It was observed that the RT negative control amplification was below the threshold (FIG. 7A-7F). It is contemplated that in some embodiments, the method as described in this Example can be used to detect 12-18 miRNA targets in 4-6 different fluorescent channels.

Example 2: Single-Color Multiplexed Detection of DNA Targets Using Common Quencher Oligo Approach Materials and Methods Primers, Probes and Quencher Oligonucleotides The following oligonucleotides were designed and synthesized.

```
Quencher Sequence:
                                              (SEQ ID NO: 11)
5'-GCCTGCGTGCCT-BHQ®1-3'

Probe A Sequence:
                                              (SEQ ID NO: 17)
5'-FAM™--AGGCACGTCACCGGGTGTAAATCAGCTTG-pho-3'
(24 degree melting)

Probe B Sequence:
                                              (SEQ ID NO: 18)
5'-FAM™--AGGCACGCATAGCAGCACGTAAATATTGGCG-pho-3'
(44 degree melting)

Probe C Sequence:
                                              (SEQ ID NO: 19)
5'-FAM™--AGGCACGCAGGCTGTCAGTTTGTCAAATA
CCCCA-pho-3'
(58 degree melting)
```

For detection Probes A, B and C above, the bolded sequences represent the tag to which the quencher oligonucleotide binds to unbound probe during the qPCR reaction.

```
Common Forward Primer:
                                              (SEQ ID NO: 12)
5'-GCGCTATCCGACAATTTCCA-3'

Common Reverse Primer:
                                              (SEQ ID NO: 13)
5'-TAAATCCCGCATGCTCGACG-3'

Template A:
                                              (SEQ ID NO: 20)
TAGTCGCGCTATCCGACAATTTCCAAATTATCAGGCACGTC

ACCGGGTGTAAATCAGCTTGGTAGCGTCGAGCATGCGGGA

TTTATTGCAT

Template B:
                                              (SEQ ID NO: 21)
TAGTCGCGCTATCCGACAATTTCCAAATTATCAGGCACGCA

TAGCAGCACGTAAATATTGGCGGTAGCGTCGAGCATGCGG

GATTTATTGCAT

Template C:
                                              (SEQ ID NO: 22)
TAGTCGCGCTATCCGACAATTTCCAAATTATCAGGCACGCA

GGCTGTCAGTTTGTCAAATACCCCAGTAGCGTCGAGCATGC

GGGATTTATTGCAT
```

For templates A, B and C above, the bolded sequences represent the tag sequences to which detection probe binds in the template.

qPCR

Target A, B, and C (pooled or alone) were used as template in a single qPCR reaction set up as follows:

10× EconoTaq Buffer: 2 µl dNTP mix: 0.5 µl

10 µM Common Forward Primer: 1 µl

10 µM Common Reverse Primer: 1 µl 25 mM MgCl2: 2 µl

10 µM Common Quencher: 2 µl

Enzyme: 0.5 µl (2.5 U)

10 µM Probe (Target A, B, and C): 0.25 µl each

Water: 3.25 µl

Template (each at 6.02×10^5 copies/reaction): 7.5 µl qPCR qPCR was performed by incubating the reaction at 95° C. for 2 mins (initial denaturation), followed by 40 cycles of 95° C. for 5 sec, 24° C. for 12 sec, 44° C. for 12 sec, 58° C. for 12 sec, and 72° C. for 12 sec. For each cycle, fluorescent data was captured at each 24° C., 44° C., 58° C., and 72° C. incubation step.

Results

Figure 8A:
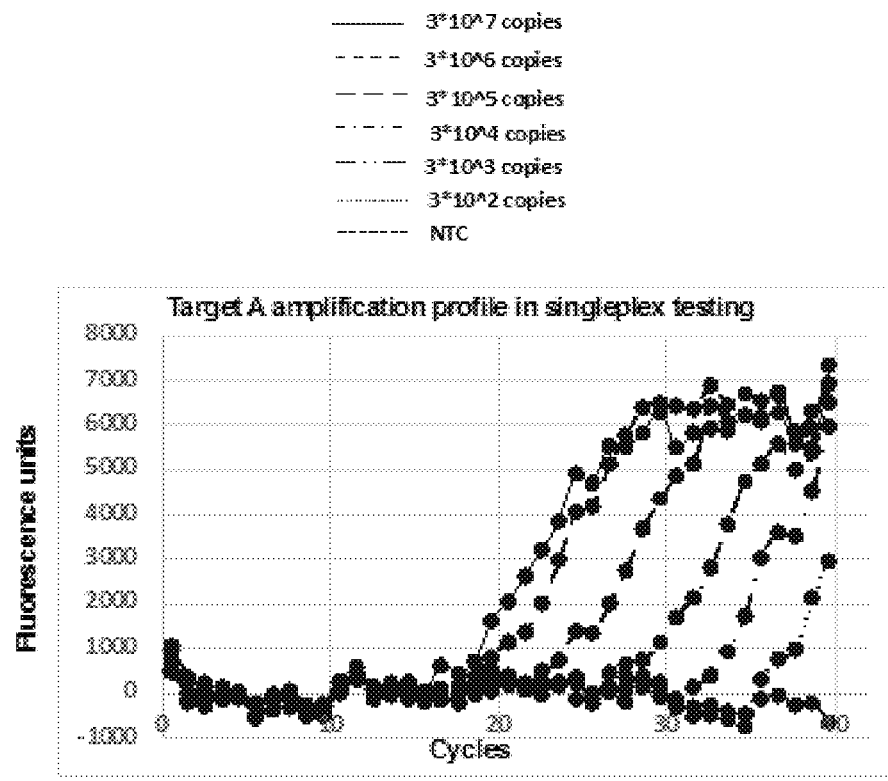
FIGS. 8A-8L are graphs illustrating the results of assay illustrating three-target, single color multiplexing using a common quencher detection approach. Synthetic DNA templates of Targets A, B, and C were tested as described in the Examples and detected in fluorescein (FAM™) channel using qPCR methodology disclosed herein. NTC—no template control.
Figure 8B:
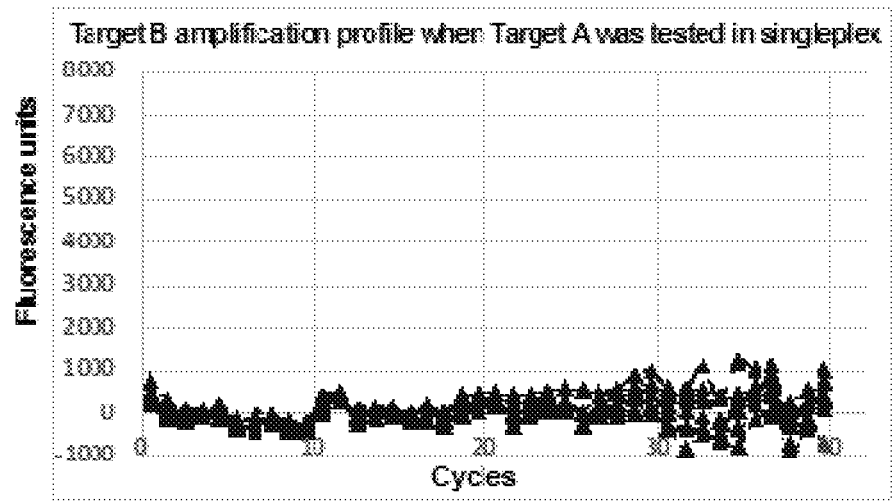
Figure 8C:
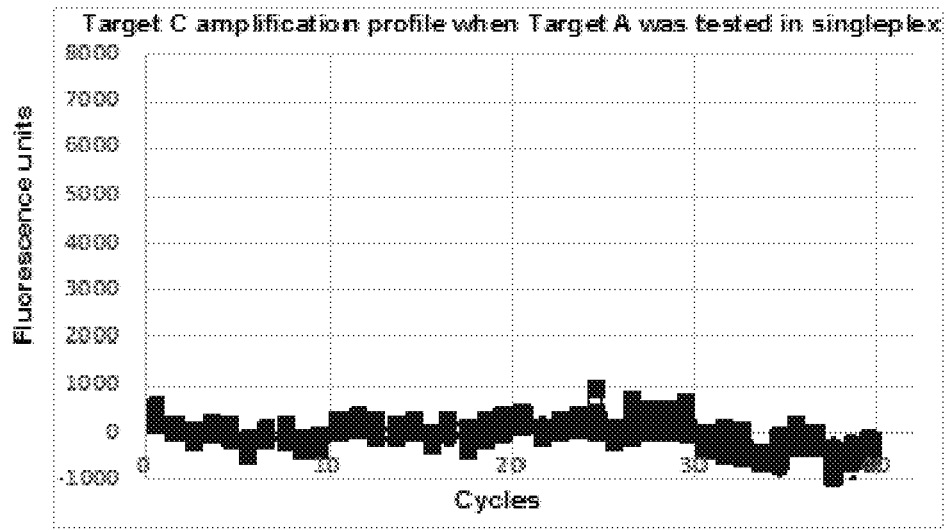
Figure 8D:
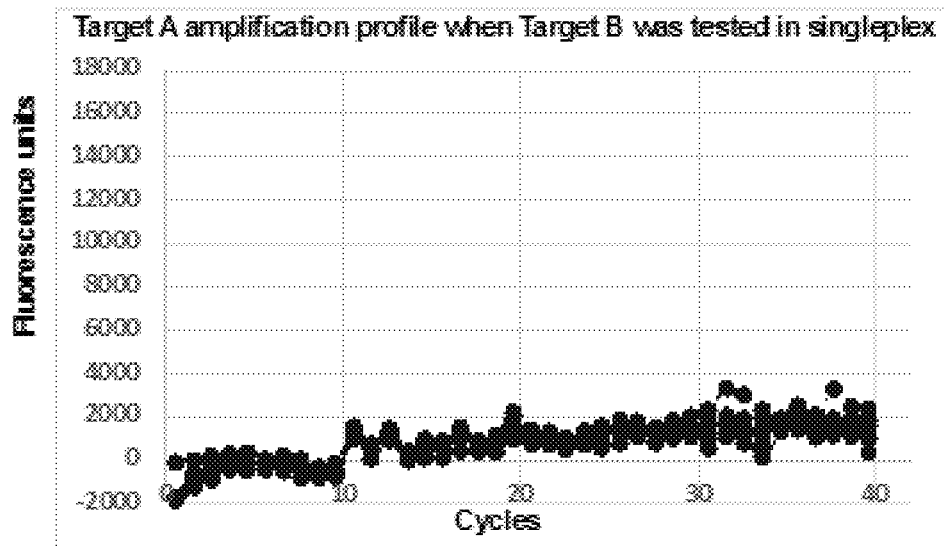
Figure 8E:
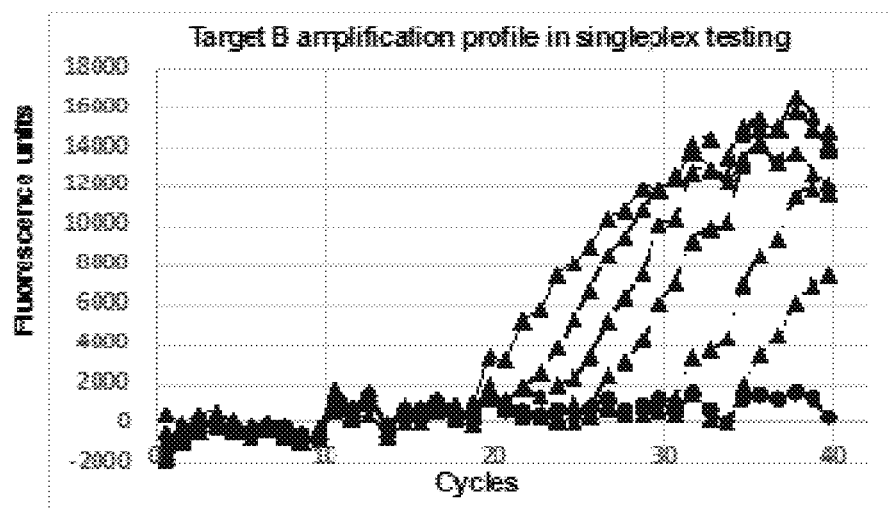
Figure 8F:
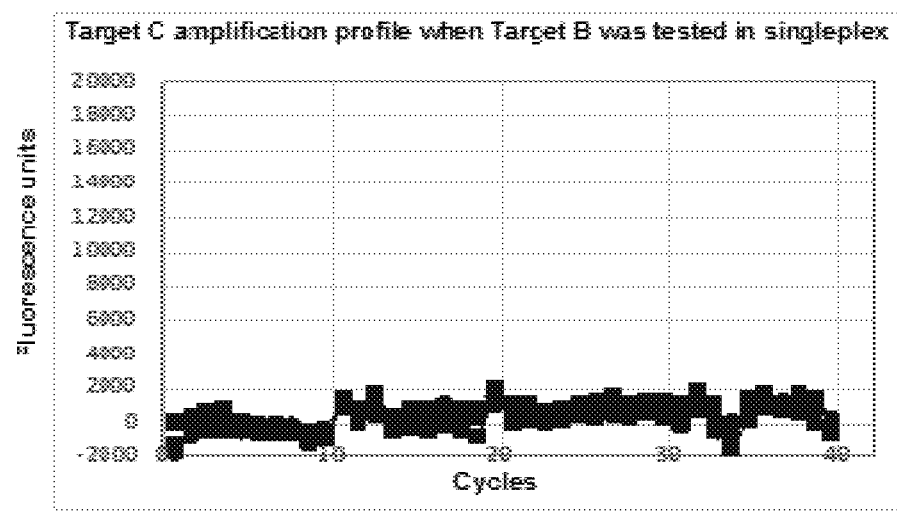
Figure 8G:
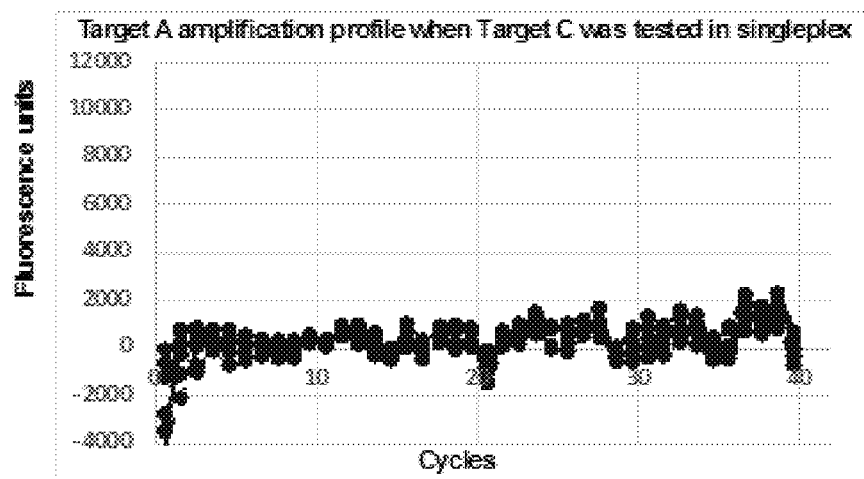
Figure 8H:
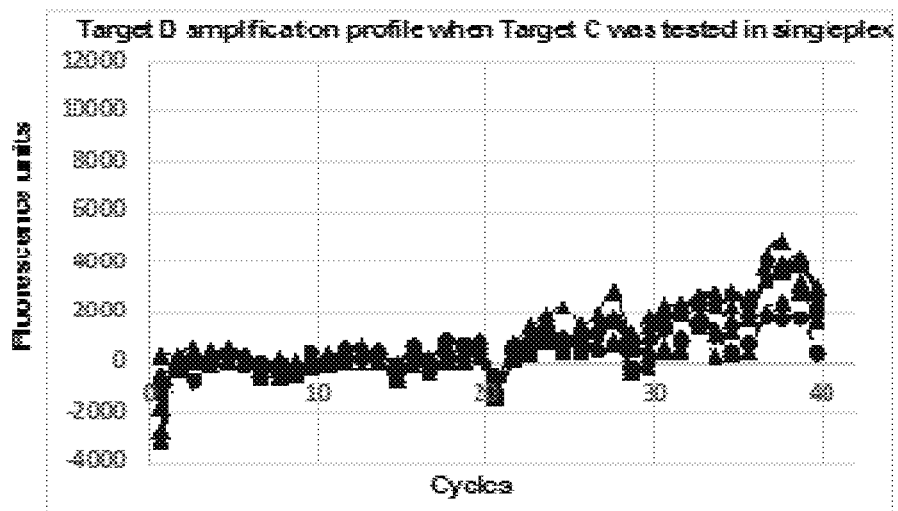
Figures 8I, 8J:
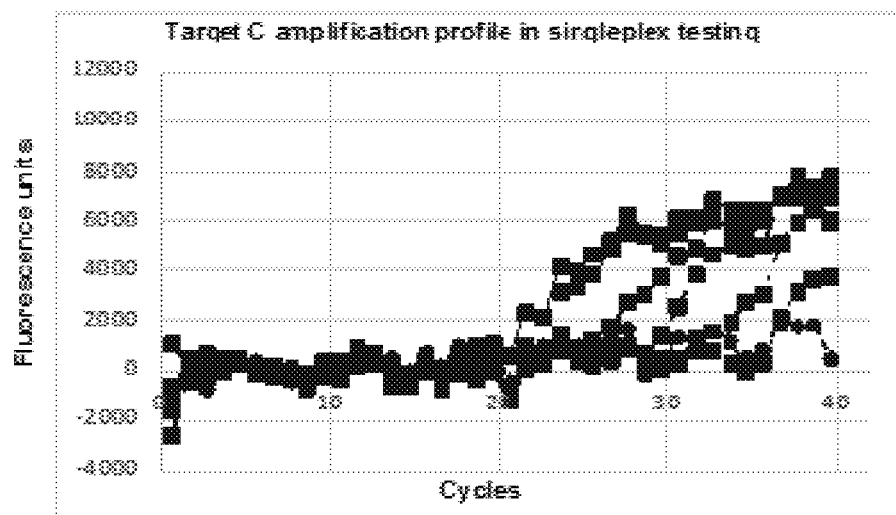
Figure 8K:
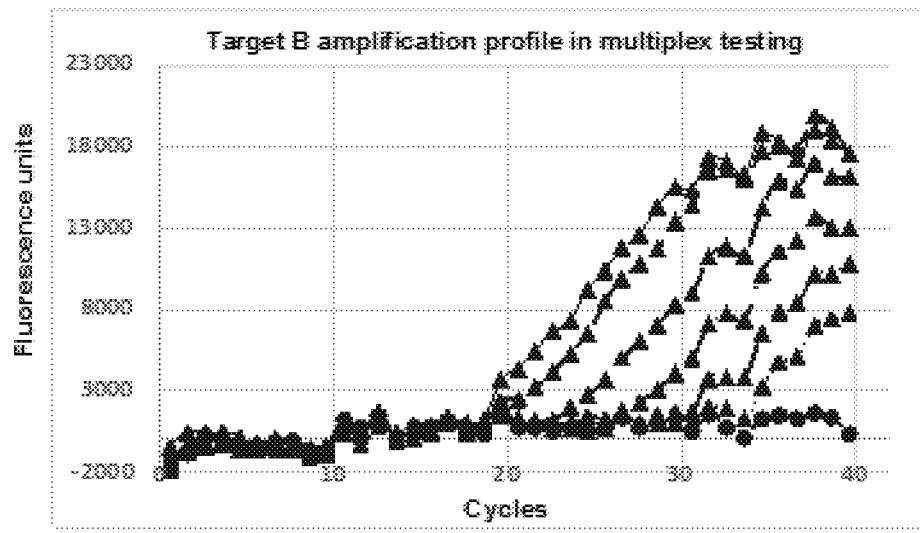
Figure 8L:
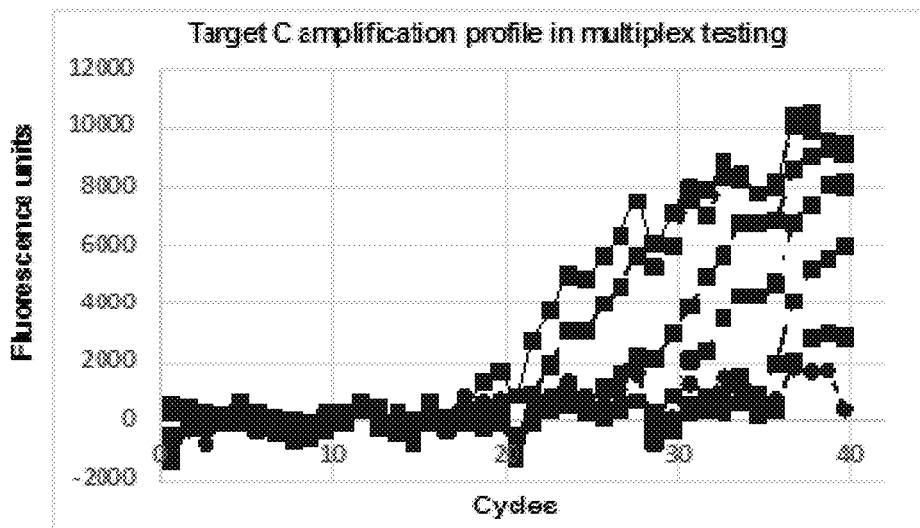

Three targets, synthetic DNA for target A, B, and C were tested either as a pool (multiplex) or alone (singleplex) (3*10^7, 3*10^6, 3*10^5, 3*10^4, 3*10^3, 3*10^2 copies/target) and used as template per qPCR reaction. qPCR protocol included incubation at 95° C. for 2 mins, followed by 40 cycles using proprietary qPCR protocol. Each qPCR reaction contained primers, CFP, and CRP, three specific FAM™ probes and a common quencher. Fluorescence data was collected at 24° C., 44° C., 58° C., and 72° C. The predicted melting temperature of the detection probe-quencher oligonucleotide complex was 24° C. for Probe A, 44° C. for Probe B, and 58° C. for Probe C. The fluorescence data was deconvoluted as described herein. Target A amplification was determined using fluorescence data collected at 44° C. and 24° C.; Target B amplification was determined using fluorescent data collected at 58° C. and 44° C.; and Target C amplification was determined using fluorescence data collected at 72° C. and 58° C. After the qPCR reaction, fluorescent data was analyzed. As shown, a specific amplification of either Target A (FIG. 8A), or Target B (FIG. 8E), or Target C (FIG. 8I) was found when tested in a singleplex condition. When Target A was tested alone, there was no signal for Target B (FIG. 8B) or C (FIG. 8C); when Target B was tested there was no signal for Target A (FIG. 8D) or Target C (FIG. 8F); when Target C was tested there was no signal for Target A (FIG. 8G) or Target B (FIG. 8H). When Targets A, B, and C were pooled and amplified (multiplex), there was specific amplification of Target A, B, and C (FIG. 8J-8L). As shown, this method can detect, discriminate, and quantify up to three targets in a single FAM™ channel (FIG. 8A-8L).

Example 3: Quencher and Experimental Design for Single-Color Multiplexed Detection of DNA Targets Using Specific Quencher Oligo Approach In another example, the method of Example 2 can be utilized in single-color multiplexed detection of DNA targets using a specific quencher oligo approach, by replacing the above-utilized primers, probes, and quenchers with the following primers, probes, and quenchers.

Primers, Probes and Quencher Oligonucleotides

The following quencher and probe oligonucleotides are exemplary to show how the common quencher approach of Example 2 could be modified utilize a specific quencher oligos detection approach.

```
Quencher Sequence-1:
                                       (SEQ ID NO: 11)
5'-GCCTGCGTGCCT-BHQ®1-3'

Quencher Sequence-2:
5'-TGGCTCGCT-BHQ®1-3'

Quencher Sequence-3:
5'-CTGCCGT-BHQ®1-3'

Probe A Sequence:
                                       (SEQ ID NO: 17)
5'-FAM™--ACGGCAGTCACCGGGTGTAAATCAGCTT
G-pho-3'
(24 degree melting)

Probe B Sequence:
                                       (SEQ ID NO: 18)
5'-FAM™--AGCGAGCCATAGCAGCACGTAAATATTGGC
G-pho-3'
(44 degree melting)

Probe C Sequence:
                                       (SEQ ID NO: 19)
5'-FAM™--AGGCACGCAGGCTGTCAGTTTGTCAAATAC
CCCA-pho-3'
(58 degree melting)
```

For detection Probes A, B and C above, the bolded sequences to which the quencher oligonucleotide binds to unbound probe during the qPCR reaction.

```
Common Forward Primer:
                                       (SEQ ID NO: 12)
5'-GCGCTATCCGACAATTTCCA-3'

Common Reverse Primer:
                                       (SEQ ID NO: 13)
5'-TAAATCCCGCATGCTCGACG-3'

Template A:
                                       (SEQ ID NO: 23)
TAGTCGCGCTATCCGACAATTTCCAAATTATCACGGCAGTC
ACCGGGTGTAAATCAGCTTGGTAGCGTCGAGCATGCGGGA
TTTATTGCAT Template B:
                                       (SEQ ID NO: 24)
TAGTCGCGCTATCCGACAATTTCCAAATTATCAGCGAGCCA
TAGCAGCACGTAAATATTGGCGGTAGCGTCGAGCATGCGG
GATTTATTGCAT Template C:
                                       (SEQ ID NO: 22)
TAGTCGCGCTATCCGACAATTTCCAAATTATCAGGCACGCA
GGCTGTCAGTTTGTCAAATACCCCAGTAGCGTCGAGCATGC
GGGATTTATTGCAT
```

For templates A, B and C above, the bolded sequences represent the sequences to which detection probe binds in the template.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method for detection of two or more distinct target polynucleotides in a sample the method comprising
performing one or more amplification cycles on the sample using a polymerase and universal or target-specific forward and reverse primers to generate amplified products corresponding to the target polynucleotides, and
detecting and/or quantifying each amplified product using a plurality of distinct unbound detection probes and a plurality of corresponding quencher oligonucleotides that can hybridize thereto,
wherein the detecting and/or quantifying comprises measuring unbound or free detection probes.

2. The method of claim 1, wherein the quencher oligonucleotide and probe are not linked.

3. The method of claim 1, wherein the primers comprise or consist of labeled, target-specific forward and/or reverse primers and wherein the probes are the labelled primers, and, optionally wherein the labelled primers and quencher oligonucleotides are not linked.

4. The method of claim 1, wherein the probes and corresponding quencher oligonucleotides are linked.

5. The method of claim 1, wherein each detection probe in the plurality of detection probes comprises an identical fluorophore, and a target-specific sequence that is complementary to and hybridizes to a target amplified product.

6. The method of claim 5, wherein each detection probe in the plurality of detection probes comprises a tag different in sequence and/or size from that of other distinct probes in the plurality of detection probes.

7. The method of claim 6, wherein the plurality of quencher oligonucleotides comprises an identical fluorescence quencher and an identical tag-binding sequence that is partially or fully complementary to the tags of the detection probes.

8. The method of claim 6, wherein for each distinct detection probe, the plurality of quencher oligonucleotides comprises a quencher oligonucleotide comprising a sequence that is fully complementary to part or all of the sequence of the distinct detection probe, wherein each quencher oligonucleotide in the plurality of quencher oligonucleotides comprises an identical fluorescence quencher and differs from other quencher oligonucleotides in sequence.

9. The method of claim 7, wherein the quencher oligonucleotides are capable of hybridizing to each distinct detection probe to form a plurality of unique detection probe-quencher oligonucleotide complexes, wherein each detection probe-quencher oligonucleotide complex exhibits a unique melting temperature.

10. The method of claim 9, wherein formation of the detection probe-quencher oligonucleotide complex results in quenching of fluorescence from the fluorophore by the fluorescence quencher, wherein fluorescence is unquenched at a temperature above the unique melting temperature for each detection probe-quencher oligonucleotide complex.

11. The method of claim 10, wherein fluorescence is measured at or below each unique melting temperature after one or more amplification cycles, optionally after each amplification cycle, and/or at the beginning and the end of the amplification reaction.

12. The method of claim 11, wherein the amplified products corresponding to the two or more target polynucleotides are distinguished and/or quantified by the amount of fluorescence arising from unbound probe and quencher oligonucleotide complex dissociation measured at each unique melting temperature.

13. The method of claim 1, wherein the plurality of detection probes comprises two or more groups of detection probes, wherein each group of detection probes comprises an identical fluorophore, wherein each distinct detection probe in a group comprises a tag different in sequence and/or size from that of other probes in the group, and a target-specific sequence that is complementary to and hybridizes to a distinct target amplified product.

14. The method of claim 13, wherein each group of detection probes comprises 3 or 4 distinct detection probes.

15. The method of claim 13, wherein for each group of detection probes the plurality of quencher oligonucleotides comprises an identical fluorescence quencher and an identical tag-binding sequence that is partially or fully complementary to the tags of the detection probes in the group or the plurality of quencher oligonucleotides comprises specific sequences that is fully complementary to the detection probes in the group.

16. The method of claim 13, wherein for each distinct detection probe, the plurality of quencher oligonucleotides comprises a quencher oligonucleotide comprising a sequence that is fully complementary to part or all of the sequence of the distinct detection probe, and wherein for each group of detection probes, each quencher oligonucleotide in the plurality of quencher oligonucleotides comprises an identical fluorescence quencher.

17. The method of claim 15, wherein the quencher oligonucleotides are capable of hybridizing to each distinct detection probe to form a plurality of unique detection probe-quencher oligonucleotide complexes, wherein each detection probe-quencher oligonucleotide complex exhibits a unique melting temperature.

18. The method of claim 17, wherein formation of the detection probe-quencher oligonucleotide complex results in quenching of fluorescence from the fluorophore by the fluorescence quencher, wherein fluorescence is unquenched at a temperature above the unique melting temperature for each detection probe-quencher oligonucleotide complex.

19. The method of claim 18, wherein fluorescence is measured at each unique melting temperature after one or more amplification cycles, optionally after each amplification cycle, and/or at the beginning and the end of the amplification reaction.

20. The method of claim 19, wherein the amplified products corresponding to the two or more target polynucleotides are distinguished and/or quantified by the amount of fluorescence measured at each temperature.

21. The method of claim 1, wherein the amplification comprises isothermal amplification, or PCR, optionally wherein the PCR is quantitative PCR (qPCR) or digital PCR (dPCR).

22. The method of claim 1, wherein the target polynucleotide comprises DNA or RNA.

23. The method of claim 22, wherein the target polynucleotide comprises RNA and the amplification is preceded by reverse transcription of the RNA.

24. The method of claim 23, wherein the RNA is selected from small nucleolar RNA, messenger RNA (mRNA), small interfering RNA (siRNA), microRNA (miRNA), or antisense RNA.

25. The method of claim 24, wherein the RNA is miRNA, wherein reverse transcription of the miRNA comprises (a) bringing a sample comprising the miRNA into contact with a single-stranded RT primer and optionally a blocker oligonucleotide under conditions suitable for the RT primer to hybridize to the target miRNA,
    wherein the RT primer comprises in the 5' to 3' direction,
        (i) a tag collectively comprising a universal reverse primer sequence and a binding site for the blocker oligonucleotide, and (ii) a sequence complementary to the 3'-end of the target miRNA; and (b) performing reverse transcription to obtain cDNA.

26. The method of claim 1, wherein the one or more amplification cycles each comprise a plurality of temperatures, and the detecting and/or quantifying comprises detection of unbound or free detection probes at different temperatures.

27. The method of claim 1 comprising two or more amplification cycles,
    wherein the detecting and/or quantifying comprises detection of unbound or free detection probes at different cycles.

28. The method of claim 1, comprising two or more amplification cycles,
- wherein each amplification cycle comprises a plurality of temperatures, and
- wherein the detecting and/or quantifying comprises detection of unbound or free detection probes at different temperatures during each cycle.

29. The method of claim 28, wherein the unbound or free detection probes are measured according to quenching and unquenching at different cycles and temperatures.

30. The method of claim 20, wherein the distinguishing and/or quantification comprises deconvolution of the measured fluorescence.

* * * * *